United States Patent
Szabados et al.

(10) Patent No.: US 11,083,371 B1
(45) Date of Patent: Aug. 10, 2021

(54) METHODS AND SYSTEMS FOR PROCESSING DATA VIA AN EXECUTABLE FILE ON A MONITOR TO REDUCE THE DIMENSIONALITY OF THE DATA AND ENCRYPTING THE DATA BEING TRANSMITTED OVER THE WIRELESS NETWORK

(71) Applicant: iRhythm Technologies, Inc., San Francisco, CA (US)

(72) Inventors: Steven Szabados, Sausalito, CA (US); Yuriko Tamura, San Mateo, CA (US); Xixi Wang, South San Francisco, CA (US); George Mathew, Berkeley, CA (US)

(73) Assignee: iRhythm Technologies, Inc., San Francisco, CA (US)

( * ) Notice: Subject to any disclaimer, the term of this patent is extended or adjusted under 35 U.S.C. 154(b) by 0 days.

(21) Appl. No.: 17/174,145

(22) Filed: Feb. 11, 2021

Related U.S. Application Data

(60) Provisional application No. 62/975,626, filed on Feb. 12, 2020, provisional application No. 63/090,951, filed on Oct. 13, 2020.

(51) Int. Cl.
*A61B 5/00* (2006.01)
*A61B 5/28* (2021.01)
(Continued)

(52) U.S. Cl.
CPC .............. *A61B 5/0006* (2013.01); *A61B 5/11* (2013.01); *A61B 5/257* (2021.01); *A61B 5/28* (2021.01); *A61B 5/361* (2021.01); *A61B 5/363* (2021.01); *A61B 5/6801* (2013.01); *A61B 5/7267* (2013.01); *G06F 21/6245* (2013.01); *A61B 2562/0219* (2013.01); *A61B 2562/166* (2013.01); *A61B 2562/168* (2013.01)

(58) Field of Classification Search
None
See application file for complete search history.

(56) References Cited

U.S. PATENT DOCUMENTS

| 1,497,079 A | 6/1924 | Gullborg |
| 2,179,922 A | 11/1939 | Dana |

(Continued)

FOREIGN PATENT DOCUMENTS

| AU | 2011252998 | 8/2015 |
| AU | 2014209376 | 6/2017 |

(Continued)

OTHER PUBLICATIONS

US 8,750,980 B2, 06/2014, Katra et al. (withdrawn)
(Continued)

*Primary Examiner* — Ankit D Tejani
(74) *Attorney, Agent, or Firm* — Knobbe, Martens, Olson & Bear, LLP

(57) ABSTRACT

Some embodiments include processing data via an executable file on a monitor to reduce the dimensionality of the data being transmitted over the wireless network. The output of the executable file also encrypts the data before being transmitted wireless to a remote server. The remote server receives the transmitted data and makes likelihood inferences based on the recorded data.

19 Claims, 41 Drawing Sheets

(51) Int. Cl.
*A61B 5/11* (2006.01)
*A61B 5/257* (2021.01)
*A61B 5/363* (2021.01)
*G06F 21/62* (2013.01)
*A61B 5/361* (2021.01)

(56) References Cited

U.S. PATENT DOCUMENTS

| | | |
|---|---|---|
| 2,201,645 A | 5/1940 | Epner |
| 2,311,060 A | 2/1943 | Lurrain |
| 2,444,552 A | 7/1948 | Brantingson |
| 2,500,840 A | 3/1950 | Lyons |
| 3,215,136 A | 11/1965 | Holter et al. |
| 3,547,107 A | 12/1970 | Chapman et al. |
| 3,697,706 A | 10/1972 | Huggard |
| 3,870,034 A | 3/1975 | James |
| 3,882,853 A | 5/1975 | Gofman |
| 3,911,906 A | 10/1975 | Reinhold |
| 4,023,312 A | 5/1977 | Stickney |
| 4,027,664 A | 6/1977 | Heavner, Jr. et al. |
| 4,082,087 A | 4/1978 | Howson |
| 4,121,573 A | 10/1978 | Crovella et al. |
| 4,123,785 A | 10/1978 | Cherry et al. |
| 4,126,126 A | 11/1978 | Bare |
| 4,202,139 A | 5/1980 | Hong et al. |
| 4,274,419 A | 6/1981 | Tam et al. |
| 4,274,420 A | 6/1981 | Hymes |
| 4,286,610 A | 9/1981 | Jones |
| 4,333,475 A | 6/1982 | Moreno et al. |
| 4,361,990 A | 12/1982 | Link |
| 4,381,792 A | 5/1983 | Busch |
| 4,438,767 A | 3/1984 | Nelson |
| 4,459,987 A | 7/1984 | Pangburn |
| 4,535,783 A | 8/1985 | Marangoni |
| 4,537,207 A | 8/1985 | Gilhaus |
| 4,572,187 A | 2/1986 | Schetrumpf |
| 4,621,465 A | 11/1986 | Pangburn |
| 4,622,979 A | 11/1986 | Katchis et al. |
| 4,658,826 A | 4/1987 | Weaver |
| 4,712,552 A | 12/1987 | Pangburn |
| 4,736,752 A | 4/1988 | Munck et al. |
| 4,925,453 A | 5/1990 | Kannankeril |
| 4,938,228 A | 7/1990 | Righter et al. |
| 4,981,141 A | 1/1991 | Segalowitz |
| 5,003,987 A | 4/1991 | Grinwald |
| 5,027,824 A | 7/1991 | Dougherty et al. |
| 5,082,851 A | 1/1992 | Appelbaum et al. |
| 5,086,778 A | 2/1992 | Mueller et al. |
| 5,191,891 A | 3/1993 | Righter |
| 5,205,295 A | 4/1993 | Del Mar et al. |
| 5,226,425 A | 7/1993 | Righter |
| 5,228,450 A | 7/1993 | Sellers |
| 5,230,119 A | 7/1993 | Woods et al. |
| 5,289,824 A | 3/1994 | Mills et al. |
| 5,305,746 A | 4/1994 | Fendrock |
| 5,309,909 A | 5/1994 | Gadsby |
| 5,365,935 A | 11/1994 | Righter et al. |
| 5,458,141 A | 10/1995 | Neil |
| 5,483,967 A | 1/1996 | Ohtake |
| 5,489,624 A | 2/1996 | Kantner et al. |
| 5,511,553 A | 4/1996 | Segalowitz |
| 5,515,858 A | 5/1996 | Myllymaki |
| 5,536,768 A | 7/1996 | Kantner et al. |
| 5,581,369 A | 12/1996 | Righter et al. |
| 5,626,140 A | 5/1997 | Feldman et al. |
| 5,634,468 A | 6/1997 | Platt et al. |
| 5,645,063 A | 7/1997 | Straka |
| 5,645,068 A | 7/1997 | Mezack et al. |
| 5,730,143 A | 3/1998 | Schwarzberg |
| 5,749,365 A | 5/1998 | Magill |
| 5,749,367 A | 5/1998 | Gamlyn et al. |
| 5,771,524 A | 6/1998 | Woods et al. |
| 5,772,604 A | 6/1998 | Langberg et al. |
| 5,776,072 A | 7/1998 | Hsu et al. |
| 5,881,743 A | 3/1999 | Nadel |
| D408,541 S | 4/1999 | Dunshee et al. |
| 5,916,239 A | 6/1999 | Geddes et al. |
| 5,931,791 A | 8/1999 | Saltzstein et al. |
| 5,941,829 A | 8/1999 | Saltzstein et al. |
| 5,957,854 A | 9/1999 | Besson et al. |
| 5,959,529 A | 9/1999 | Kail |
| 6,013,007 A | 1/2000 | Root et al. |
| 6,032,060 A | 2/2000 | Carim |
| 6,038,464 A | 3/2000 | Axelgaard et al. |
| 6,038,469 A | 3/2000 | Karlsson et al. |
| 6,044,515 A | 4/2000 | Zygmont |
| 6,093,146 A | 7/2000 | Filangeri |
| D429,336 S | 8/2000 | Francis et al. |
| 6,102,856 A | 8/2000 | Groff et al. |
| 6,117,077 A | 9/2000 | Del Mar et al. |
| 6,132,371 A | 10/2000 | Dempsey et al. |
| 6,134,480 A | 10/2000 | Minogue |
| 6,136,008 A | 10/2000 | Becker et al. |
| 6,161,036 A | 12/2000 | Matsumura et al. |
| 6,169,915 B1 | 1/2001 | Krumbiegel et al. |
| 6,178,357 B1 | 1/2001 | Gliner et al. |
| 6,200,265 B1 | 3/2001 | Walsh et al. |
| 6,225,901 B1 | 5/2001 | Kail |
| 6,232,366 B1 | 5/2001 | Wang et al. |
| 6,238,338 B1 | 5/2001 | DeLuca et al. |
| 6,248,115 B1 | 6/2001 | Halk |
| 6,287,252 B1 | 9/2001 | Lugo |
| 6,290,707 B1 | 9/2001 | Street |
| 6,315,719 B1 | 11/2001 | Rode et al. |
| 6,379,237 B1 | 4/2002 | Gordon |
| 6,385,473 B1 | 5/2002 | Haines et al. |
| 6,389,308 B1 | 5/2002 | Shusterman |
| 6,416,471 B1 | 7/2002 | Kumar et al. |
| 6,434,410 B1 | 8/2002 | Cordero et al. |
| 6,441,747 B1 | 8/2002 | Khair et al. |
| 6,454,708 B1 | 9/2002 | Ferguson et al. |
| 6,456,871 B1 | 9/2002 | Hsu et al. |
| 6,456,872 B1 | 9/2002 | Faisandier |
| 6,464,815 B1 | 10/2002 | Beaudry |
| 6,493,898 B1 | 12/2002 | Woods et al. |
| 6,496,705 B1 | 12/2002 | Ng et al. |
| 6,510,339 B2 | 1/2003 | Kovtun et al. |
| 6,546,285 B1 | 4/2003 | Owen et al. |
| 6,564,090 B2 | 5/2003 | Taha et al. |
| 6,569,095 B2 | 5/2003 | Eggers |
| 6,577,893 B1 | 6/2003 | Besson et al. |
| 6,580,942 B1 | 6/2003 | Willshire |
| 6,585,707 B2 | 7/2003 | Cabiri et al. |
| 6,589,170 B1 | 7/2003 | Flach et al. |
| 6,589,187 B1 | 7/2003 | Dimberger et al. |
| 6,605,046 B1 | 8/2003 | Del Mar et al. |
| 6,615,083 B2 | 9/2003 | Kupper |
| 6,622,035 B1 | 9/2003 | Merilainen |
| 6,626,865 B1 | 9/2003 | Prisell |
| 6,656,125 B2 | 12/2003 | Misczynski et al. |
| 6,664,893 B1 | 12/2003 | Eveland et al. |
| 6,665,385 B2 | 12/2003 | Rogers et al. |
| 6,690,959 B2 | 2/2004 | Thompson |
| 6,694,177 B2 | 2/2004 | Eggers et al. |
| 6,701,184 B2 | 3/2004 | Henkin |
| 6,711,427 B1 | 3/2004 | Ketelhohn |
| 6,730,028 B2 | 5/2004 | Eppstein |
| D492,607 S | 7/2004 | Curkovic et al. |
| 6,773,396 B2 | 8/2004 | Flach et al. |
| 6,775,566 B2 | 8/2004 | Nissila |
| 6,801,137 B2 | 10/2004 | Eggers |
| 6,801,802 B2 | 10/2004 | Sitzman et al. |
| 6,871,089 B2 | 3/2005 | Korzinov et al. |
| 6,871,211 B2 | 3/2005 | Labounty et al. |
| 6,875,174 B2 | 4/2005 | Braun et al. |
| 6,881,191 B2 | 4/2005 | Oakley et al. |
| 6,893,396 B2 | 5/2005 | Schulze et al. |
| 6,897,788 B2 | 5/2005 | Khair et al. |
| 6,904,312 B2 | 6/2005 | Bardy |
| 6,925,324 B2 | 8/2005 | Shusterman |
| 6,940,403 B2 | 9/2005 | Kail |
| 6,954,163 B2 | 10/2005 | Toumazou et al. |
| 6,957,107 B2 | 10/2005 | Rogers et al. |
| 6,987,965 B2 | 1/2006 | Ng et al. |

(56) References Cited

U.S. PATENT DOCUMENTS

| | | |
|---|---|---|
| 7,002,468 B2 | 2/2006 | Eveland et al. |
| 7,020,508 B2 | 3/2006 | Stivoric et al. |
| 7,024,248 B2 | 4/2006 | Penner et al. |
| 7,031,770 B2 | 4/2006 | Collins et al. |
| 7,072,708 B1 | 7/2006 | Andresen et al. |
| 7,072,709 B2 | 7/2006 | Xue |
| 7,076,283 B2 | 7/2006 | Cho et al. |
| 7,076,287 B2 | 7/2006 | Rowlandson |
| 7,076,288 B2 | 7/2006 | Skinner |
| 7,076,289 B2 | 7/2006 | Sarkar et al. |
| 7,079,977 B2 | 7/2006 | Osorio et al. |
| 7,082,327 B2 | 7/2006 | Houben |
| 7,089,048 B2 | 8/2006 | Matsumura et al. |
| 7,099,715 B2 | 8/2006 | Korzinov et al. |
| 7,117,031 B2 | 10/2006 | Lohman et al. |
| 7,120,485 B2 | 10/2006 | Glass et al. |
| 7,130,396 B2 | 10/2006 | Rogers et al. |
| 7,161,484 B2 | 1/2007 | Tsoukalis |
| 7,171,166 B2 | 1/2007 | Ng et al. |
| 7,179,152 B1 | 2/2007 | Rhoades |
| 7,186,264 B2 | 3/2007 | Liddicoat et al. |
| 7,193,264 B2 | 3/2007 | Lande |
| 7,194,300 B2 | 3/2007 | Korzinov |
| 7,206,630 B1 | 4/2007 | Tarler |
| 7,212,850 B2 | 5/2007 | Prystowsky et al. |
| 7,222,054 B2 | 5/2007 | Geva |
| 7,242,318 B2 | 7/2007 | Harris |
| 7,266,361 B2 | 9/2007 | Burdett |
| 7,316,671 B2 | 1/2008 | Lastovich et al. |
| 7,349,947 B1 | 3/2008 | Slage et al. |
| D567,949 S | 4/2008 | Lash et al. |
| 7,354,423 B2 | 4/2008 | Zelickson et al. |
| 7,387,607 B2 | 6/2008 | Holt et al. |
| 7,444,177 B2 | 10/2008 | Nazeri |
| D584,414 S | 1/2009 | Lash et al. |
| 7,477,933 B2 | 1/2009 | Ueyama |
| 7,478,108 B2 | 1/2009 | Townsend et al. |
| 7,481,772 B2 | 1/2009 | Banet |
| 7,482,314 B2 | 1/2009 | Grimes et al. |
| 7,502,643 B2 | 3/2009 | Farringdon et al. |
| 7,539,533 B2 | 5/2009 | Tran |
| 7,542,878 B2 | 6/2009 | Nanikashvili |
| 7,587,237 B2 | 9/2009 | Korzinov et al. |
| 7,630,756 B2 | 12/2009 | Linker |
| 7,632,174 B2 | 12/2009 | Gringer et al. |
| 7,672,714 B2 | 3/2010 | Kuo et al. |
| 7,715,905 B2 | 5/2010 | Kurzweil et al. |
| D618,357 S | 6/2010 | Navies |
| 7,729,753 B2 | 6/2010 | Kremliovsky et al. |
| 7,733,224 B2 | 6/2010 | Tran |
| D621,048 S | 8/2010 | Severe et al. |
| 7,815,494 B2 | 10/2010 | Gringer et al. |
| 7,841,039 B1 | 11/2010 | Squire |
| 7,889,070 B2 | 2/2011 | Reeves et al. |
| D634,431 S | 3/2011 | Severe et al. |
| 7,904,133 B2 | 3/2011 | Gehman et al. |
| 7,907,956 B2 | 3/2011 | Uhlik |
| 7,907,996 B2 | 3/2011 | Prystowsky et al. |
| 7,941,207 B2 | 5/2011 | Korzinov |
| D639,437 S | 6/2011 | Bishay et al. |
| 7,970,450 B2 | 6/2011 | Kroecker et al. |
| 7,979,111 B2 | 7/2011 | Acquista |
| 7,996,075 B2 | 8/2011 | Korzinov et al. |
| 7,996,187 B2 | 8/2011 | Nanikashvili et al. |
| 8,002,701 B2 | 8/2011 | John et al. |
| D645,968 S | 9/2011 | Kasabach et al. |
| 8,077,042 B2 | 12/2011 | Peeters |
| 8,103,333 B2 | 1/2012 | Tran |
| 8,108,036 B2 | 1/2012 | Tran |
| 8,170,639 B2 | 1/2012 | Hauge |
| 8,116,841 B2 | 2/2012 | Bly et al. |
| 8,150,502 B2 | 4/2012 | Kumar et al. |
| 8,156,945 B2 | 4/2012 | Hart |
| 8,160,682 B2 | 4/2012 | Kumar et al. |
| D659,836 S | 5/2012 | Bensch et al. |
| 8,200,319 B2 | 6/2012 | Pu et al. |
| D663,432 S | 7/2012 | Nichols |
| 8,214,007 B2 | 7/2012 | Baker et al. |
| 8,244,335 B2 | 8/2012 | Kumar et al. |
| 8,249,686 B2 | 8/2012 | Libbus et al. |
| 8,261,754 B2 | 9/2012 | Pitstick |
| 8,265,907 B2 | 9/2012 | Nanikashvili et al. |
| RE43,767 E | 10/2012 | Eggers et al. |
| 8,280,749 B2 | 10/2012 | Hsieh et al. |
| 8,285,356 B2 | 10/2012 | Bly et al. |
| 8,290,129 B2 | 10/2012 | Rogers et al. |
| 8,290,574 B2 | 10/2012 | Field et al. |
| 8,301,219 B2 | 10/2012 | Chen et al. |
| 8,301,236 B2 | 10/2012 | Baumann et al. |
| 8,311,604 B2 | 11/2012 | Rowlandson et al. |
| 8,315,687 B2 | 11/2012 | Cross et al. |
| 8,315,695 B2 | 11/2012 | Sebelius et al. |
| 8,323,188 B2 | 12/2012 | Tran |
| 8,326,394 B2 | 12/2012 | Rowlandson et al. |
| 8,326,407 B2 | 12/2012 | Linker |
| 8,328,718 B2 | 12/2012 | Tran |
| D674,009 S | 1/2013 | Nichols |
| 8,343,116 B2 | 1/2013 | Ignon |
| 8,369,936 B2 | 2/2013 | Farringdon et al. |
| 8,374,688 B2 | 2/2013 | Libbus et al. |
| 8,386,009 B2 | 2/2013 | Lindberg et al. |
| 8,388,543 B2 | 3/2013 | Chon et al. |
| 8,406,843 B2 | 3/2013 | Tiegs et al. |
| 8,412,317 B2 | 4/2013 | Mazar |
| 8,417,326 B2 | 4/2013 | Chon et al. |
| 8,425,414 B2 | 4/2013 | Eveland |
| 8,449,471 B2 | 5/2013 | Tran |
| 8,452,356 B2 | 5/2013 | Vestel et al. |
| 8,460,189 B2 | 6/2013 | Libbus et al. |
| 8,473,039 B2 | 6/2013 | Michelson et al. |
| 8,473,047 B2 | 6/2013 | Chakravarthy et al. |
| 8,478,418 B2 | 7/2013 | Fahey |
| 8,483,809 B2 | 7/2013 | Kim et al. |
| 8,500,636 B2 | 8/2013 | Tran |
| 8,515,529 B2 | 8/2013 | Pu et al. |
| 8,525,673 B2 | 9/2013 | Tran |
| 8,535,223 B2 | 9/2013 | Corroy et al. |
| 8,538,503 B2 | 9/2013 | Kumar et al. |
| 8,540,731 B2 | 9/2013 | Kay |
| 8,560,046 B2 | 10/2013 | Kumar et al. |
| 8,562,527 B2 | 10/2013 | Braun et al. |
| 8,571,645 B2 | 10/2013 | Wu et al. |
| 8,588,908 B2 | 11/2013 | Moorman et al. |
| 8,591,430 B2 | 11/2013 | Amurthur et al. |
| 8,594,763 B1 | 11/2013 | Bibian |
| 8,626,262 B2 | 1/2014 | McGusty et al. |
| 8,639,319 B2 | 1/2014 | Hugh et al. |
| 8,668,643 B2 | 3/2014 | Kinast |
| 8,684,900 B2 | 4/2014 | Tran |
| 8,684,925 B2 | 4/2014 | Amurthur et al. |
| 8,688,189 B2 | 4/2014 | Shennib |
| 8,688,190 B2 | 4/2014 | Libbus et al. |
| 8,688,202 B2 | 4/2014 | Brockway et al. |
| 8,718,742 B2 | 5/2014 | Beck et al. |
| 8,718,752 B2 | 5/2014 | Libbus et al. |
| 8,718,753 B2 | 5/2014 | Chon et al. |
| 8,731,632 B1 | 5/2014 | Sereboff et al. |
| 8,738,118 B2 | 5/2014 | Moon et al. |
| 8,744,561 B2 | 6/2014 | Fahey |
| 8,755,876 B2 | 6/2014 | Chon et al. |
| 8,782,308 B2 | 7/2014 | Vlach |
| 8,789,727 B2 | 7/2014 | Mortazavi |
| 8,790,257 B2 | 7/2014 | Libbus et al. |
| 8,795,174 B2 | 8/2014 | Manicka et al. |
| 8,818,481 B2 | 8/2014 | Bly et al. |
| 8,823,490 B2 | 9/2014 | Libbus et al. |
| 8,838,218 B2 | 9/2014 | Khair |
| 8,858,450 B2 | 10/2014 | Chon et al. |
| 8,874,185 B2 | 10/2014 | Sonnenborg |
| D719,267 S | 12/2014 | Vaccarella |
| 8,903,477 B2 | 12/2014 | Berkner |
| 8,903,484 B2 | 12/2014 | Mazar |
| 8,909,328 B2 | 12/2014 | Chon |
| 8,909,330 B2 | 12/2014 | McCombie et al. |

(56) References Cited

U.S. PATENT DOCUMENTS

| | | |
|---|---|---|
| 8,909,332 B2 | 12/2014 | Vitali et al. |
| 8,909,333 B2 | 12/2014 | Rossi |
| 8,909,832 B2 | 12/2014 | Vlach et al. |
| 8,926,509 B2 | 1/2015 | Magar et al. |
| 8,945,019 B2 | 2/2015 | Prystowsky et al. |
| 8,948,854 B2 | 2/2015 | Friedman et al. |
| 8,954,129 B1 | 2/2015 | Schlegel et al. |
| 8,956,293 B2 | 2/2015 | McCombie et al. |
| 8,968,195 B2 | 3/2015 | Tran |
| 8,972,000 B2 | 3/2015 | Manera |
| 8,979,755 B2 | 3/2015 | Szydlo-Moore et al. |
| 9,014,777 B2 | 4/2015 | Woo |
| 9,015,008 B2 | 4/2015 | Geva et al. |
| 9,017,255 B2 | 4/2015 | Raptis et al. |
| 9,017,256 B2 | 4/2015 | Gottesman |
| 9,021,161 B2 | 4/2015 | Vlach et al. |
| 9,021,165 B2 | 4/2015 | Vlach |
| 9,026,190 B2 | 5/2015 | Shenasa et al. |
| 9,037,223 B2 | 5/2015 | Oral et al. |
| 9,044,148 B2 | 6/2015 | Michelson et al. |
| 9,084,548 B2 | 7/2015 | Bouguerra |
| 9,095,274 B2 | 8/2015 | Fein et al. |
| 9,101,264 B2 | 8/2015 | Acquista |
| 9,138,144 B2 | 9/2015 | Geva |
| 9,149,228 B2 | 10/2015 | Kinast |
| 9,173,670 B2 | 11/2015 | Sepulveda et al. |
| 9,179,851 B2 | 11/2015 | Baumann et al. |
| D744,659 S | 12/2015 | Bishay et al. |
| 9,211,076 B2 | 12/2015 | Kim |
| 9,226,679 B2 | 1/2016 | Balda |
| 9,241,649 B2 | 1/2016 | Kumar et al. |
| 9,241,650 B2 | 1/2016 | Amirim |
| 9,277,864 B2 | 3/2016 | Yang et al. |
| 9,282,894 B2 | 3/2016 | Banet et al. |
| 9,307,921 B2 | 4/2016 | Friedman et al. |
| 9,345,414 B1 | 5/2016 | Bardy et al. |
| 9,355,215 B2 | 5/2016 | Vlach |
| D759,653 S | 6/2016 | Toth et al. |
| 9,357,939 B1 | 6/2016 | Nosrati |
| 9,364,150 B2 | 6/2016 | Sebelius et al. |
| 9,364,155 B2 | 6/2016 | Bardy et al. |
| 9,398,853 B2 | 7/2016 | Nanikashvili |
| 9,408,545 B2 | 8/2016 | Felix et al. |
| 9,408,551 B2 | 8/2016 | Bardy et al. |
| 9,408,576 B2 | 8/2016 | Chon et al. |
| 9,414,753 B2 | 8/2016 | Chon et al. |
| 9,414,786 B1 | 8/2016 | Brockway et al. |
| D766,447 S | 9/2016 | Bishay et al. |
| 9,433,367 B2 | 9/2016 | Felix et al. |
| 9,433,380 B1 | 9/2016 | Bishay et al. |
| 9,439,566 B2 | 9/2016 | Arne et al. |
| 9,439,599 B2 | 9/2016 | Thompson et al. |
| 9,445,719 B2 | 9/2016 | Libbus et al. |
| 9,451,890 B2 | 9/2016 | Gitlin et al. |
| 9,451,975 B2 | 9/2016 | Sepulveda et al. |
| 9,474,445 B2 | 10/2016 | Eveland |
| 9,474,461 B2 | 10/2016 | Fisher et al. |
| 9,478,998 B1 | 10/2016 | Lapetina et al. |
| D773,056 S | 11/2016 | Vlach |
| 9,492,084 B2 | 11/2016 | Behar et al. |
| 9,504,423 B1 | 11/2016 | Bardy et al. |
| D775,361 S | 12/2016 | Vosch et al. |
| 9,510,764 B2 | 12/2016 | Li et al. |
| 9,510,768 B2 | 12/2016 | Rossi |
| 9,526,433 B2 | 12/2016 | Lapetina et al. |
| 9,545,204 B2 | 1/2017 | Bishay et al. |
| 9,545,228 B2 | 1/2017 | Bardy et al. |
| 9,554,715 B2 | 1/2017 | Bardy et al. |
| 9,579,020 B2 | 2/2017 | Libbus et al. |
| D780,914 S | 3/2017 | Kyvik et al. |
| 9,585,584 B2 | 3/2017 | Marek et al. |
| 9,597,004 B2 | 3/2017 | Hughes et al. |
| 9,615,763 B2 | 4/2017 | Felix et al. |
| 9,615,793 B2 | 4/2017 | Solosko et al. |
| 9,619,660 B1 | 4/2017 | Felix et al. |
| 9,642,537 B2 | 5/2017 | Felix et al. |
| 9,655,518 B2 | 5/2017 | Lin |
| 9,655,537 B2 | 5/2017 | Bardy et al. |
| 9,655,538 B2 | 5/2017 | Felix |
| 9,662,030 B2 | 5/2017 | Thng et al. |
| 9,675,264 B2 | 6/2017 | Acquista et al. |
| 9,700,227 B2 | 6/2017 | Bishay et al. |
| 9,706,938 B2 | 7/2017 | Chakravarthy et al. |
| 9,706,956 B2 | 7/2017 | Brockway et al. |
| 9,713,428 B2 | 7/2017 | Chon et al. |
| D793,566 S | 8/2017 | Bishay et al. |
| 9,717,432 B2 | 8/2017 | Bardy et al. |
| 9,717,433 B2 | 8/2017 | Felix et al. |
| 9,730,593 B2 | 8/2017 | Bardy et al. |
| 9,730,604 B2 | 8/2017 | Li et al. |
| 9,730,641 B2 | 8/2017 | Felix et al. |
| 9,736,625 B1 | 8/2017 | Landgraf et al. |
| 9,737,211 B2 | 8/2017 | Bardy et al. |
| 9,737,224 B2 | 8/2017 | Bardy et al. |
| D797,301 S | 9/2017 | Chen |
| D797,943 S | 9/2017 | Long |
| D798,170 S | 9/2017 | Toth et al. |
| D798,294 S | 9/2017 | Toth et al. |
| 9,775,534 B2 | 10/2017 | Korzinov et al. |
| 9,775,536 B2 | 10/2017 | Felix et al. |
| 9,782,095 B2 | 10/2017 | Ylostalo et al. |
| 9,782,132 B2 | 10/2017 | Golda et al. |
| 9,788,722 B2 | 10/2017 | Bardy et al. |
| 9,820,665 B2 | 11/2017 | Felix et al. |
| 9,839,363 B2 | 12/2017 | Albert |
| D810,308 S | 2/2018 | Lind et al. |
| D811,610 S | 2/2018 | Abel et al. |
| D811,611 S | 2/2018 | Lind et al. |
| D811,615 S | 2/2018 | Lind et al. |
| 9,888,866 B2 | 2/2018 | Chon et al. |
| 9,901,274 B2 | 2/2018 | Bishay et al. |
| 9,907,478 B2 | 3/2018 | Friedman et al. |
| 9,936,875 B2 | 4/2018 | Bardy et al. |
| 9,955,885 B2 | 5/2018 | Felix et al. |
| 9,955,887 B2 | 5/2018 | Hughes et al. |
| 9,955,888 B2 | 5/2018 | Felix et al. |
| 9,955,911 B2 | 5/2018 | Bardy et al. |
| 9,968,274 B2 | 5/2018 | Korzinov et al. |
| 9,986,921 B2 | 6/2018 | Chon et al. |
| 10,004,415 B2 | 6/2018 | Bishay et al. |
| D823,466 S | 7/2018 | Marogil |
| D824,526 S | 7/2018 | Ramjit et al. |
| 10,045,709 B2 | 8/2018 | Bardy et al. |
| 10,052,022 B2 | 8/2018 | Bardy et al. |
| 10,095,841 B2 | 10/2018 | Dettinger et al. |
| 10,098,559 B2 | 10/2018 | Hughes et al. |
| 10,111,601 B2 | 10/2018 | Bishay et al. |
| 10,123,703 B2 | 11/2018 | Bardy et al. |
| 10,154,793 B2 | 12/2018 | Felix et al. |
| 10,165,946 B2 | 1/2019 | Bardy et al. |
| 10,172,534 B2 | 1/2019 | Felix et al. |
| 10,251,575 B2 | 4/2019 | Bardy et al. |
| 10,251,576 B2 | 4/2019 | Bardy et al. |
| 10,264,992 B2 | 4/2019 | Felix et al. |
| 10,265,015 B2 | 4/2019 | Bardy et al. |
| 10,271,754 B2 | 4/2019 | Bahney et al. |
| 10,271,755 B2 | 4/2019 | Felix et al. |
| 10,271,756 B2 | 4/2019 | Felix et al. |
| 10,278,603 B2 | 5/2019 | Felix et al. |
| 10,278,606 B2 | 5/2019 | Bishay et al. |
| 10,278,607 B2 | 5/2019 | Prystowsky et al. |
| 10,299,691 B2 | 5/2019 | Hughes et al. |
| 10,321,823 B2 | 6/2019 | Chakravarthy et al. |
| 10,327,657 B2 | 6/2019 | Spencer et al. |
| D852,965 S | 7/2019 | Bahney et al. |
| D854,167 S | 7/2019 | Bahney et al. |
| 10,362,467 B2 | 7/2019 | Landgraf et al. |
| 10,368,808 B2 | 8/2019 | Lee et al. |
| 10,376,172 B2 | 8/2019 | Kuppuraj et al. |
| 10,390,700 B2 | 8/2019 | Bardy et al. |
| 10,398,344 B2 | 9/2019 | Beckers et al. |
| 10,405,799 B2 | 9/2019 | Kumar et al. |
| 10,413,205 B2 | 9/2019 | Bardy et al. |
| 10,426,634 B1 | 10/2019 | Al-Jazaeri et al. |

(56) References Cited

U.S. PATENT DOCUMENTS

| | | |
|---|---|---|
| 10,433,743 B1 | 10/2019 | Felix et al. |
| 10,433,748 B2 | 10/2019 | Bishay et al. |
| 10,433,751 B2 | 10/2019 | Bardy et al. |
| 10,463,269 B2 | 11/2019 | Boleyn et al. |
| 10,478,083 B2 | 11/2019 | Felix et al. |
| 10,499,812 B2 | 12/2019 | Bardy et al. |
| 10,517,500 B2 | 12/2019 | Kumar et al. |
| 10,555,683 B2 | 2/2020 | Bahney et al. |
| 10,561,326 B2 | 2/2020 | Felix et al. |
| 10,561,328 B2 | 2/2020 | Bishay et al. |
| 10,588,527 B2 | 3/2020 | McNamara et al. |
| 10,602,977 B2 | 3/2020 | Bardy et al. |
| 10,624,551 B2 | 4/2020 | Bardy et al. |
| 10,667,712 B2 | 6/2020 | Park et al. |
| 10,758,139 B2 | 9/2020 | Rapin et al. |
| 10,779,744 B2 | 9/2020 | Rapin et al. |
| 10,813,565 B2 | 10/2020 | Park et al. |
| 10,827,938 B2 | 11/2020 | Fontanarava et al. |
| 2001/0056262 A1 | 12/2001 | Cabiri et al. |
| 2002/0007126 A1 | 1/2002 | Nissila |
| 2002/0026112 A1 | 2/2002 | Nissila et al. |
| 2002/0067256 A1 | 6/2002 | Kail |
| 2002/0082491 A1 | 6/2002 | Nissila |
| 2002/0087167 A1 | 7/2002 | Winitsky |
| 2002/0180605 A1 | 12/2002 | Ozguz et al. |
| 2003/0069510 A1 | 4/2003 | Semler |
| 2003/0083559 A1 | 5/2003 | Thompson |
| 2003/0149349 A1 | 8/2003 | Jensen |
| 2003/0176795 A1 | 9/2003 | Harris et al. |
| 2003/0195408 A1 | 10/2003 | Hastings |
| 2003/0199811 A1 | 10/2003 | Sage, Jr. et al. |
| 2003/0212319 A1 | 11/2003 | Magill |
| 2004/0032957 A1 | 2/2004 | Mansy et al. |
| 2004/0068195 A1 | 4/2004 | Massicotte et al. |
| 2004/0077954 A1 | 4/2004 | Oakley et al. |
| 2004/0082843 A1 | 4/2004 | Menon |
| 2004/0215091 A1 | 10/2004 | Lohman et al. |
| 2004/0236202 A1 | 11/2004 | Burton |
| 2004/0254587 A1 | 12/2004 | Park |
| 2004/0260189 A1 | 12/2004 | Eggers et al. |
| 2005/0096513 A1 | 5/2005 | Ozguz et al. |
| 2005/0101875 A1 | 5/2005 | Semler et al. |
| 2005/0118246 A1 | 6/2005 | Wong et al. |
| 2005/0119580 A1 | 6/2005 | Eveland |
| 2005/0165323 A1 | 7/2005 | Montgomery et al. |
| 2005/0204636 A1 | 9/2005 | Azar et al. |
| 2005/0277841 A1 | 12/2005 | Shennib |
| 2005/0280531 A1 | 12/2005 | Fadem et al. |
| 2006/0030781 A1 | 2/2006 | Shennib |
| 2006/0030782 A1 | 2/2006 | Shennib |
| 2006/0047215 A1 | 3/2006 | Newman et al. |
| 2006/0084883 A1 | 4/2006 | Linker |
| 2006/0142648 A1 | 6/2006 | Banet et al. |
| 2006/0142654 A1 | 6/2006 | Rytky |
| 2006/0149156 A1 | 7/2006 | Cochran et al. |
| 2006/0155173 A1 | 7/2006 | Anttila et al. |
| 2006/0155183 A1 | 7/2006 | Kroecker et al. |
| 2006/0155199 A1 | 7/2006 | Logier et al. |
| 2006/0155200 A1 | 7/2006 | Ng et al. |
| 2006/0161064 A1 | 7/2006 | Watrous et al. |
| 2006/0161065 A1 | 7/2006 | Elion |
| 2006/0161066 A1 | 7/2006 | Elion |
| 2006/0161067 A1 | 7/2006 | Elion |
| 2006/0161068 A1 | 7/2006 | Hastings et al. |
| 2006/0167353 A1 | 7/2006 | Nazeri |
| 2006/0224072 A1 | 10/2006 | Shennib |
| 2006/0264767 A1 | 11/2006 | Shennib |
| 2007/0003695 A1 | 1/2007 | Tregub et al. |
| 2007/0010729 A1 | 1/2007 | Virtanen |
| 2007/0027388 A1 | 2/2007 | Chou |
| 2007/0088419 A1 | 4/2007 | Florina et al. |
| 2007/0156054 A1 | 7/2007 | Korzinov et al. |
| 2007/0208266 A1 | 9/2007 | Hadley |
| 2007/0225611 A1 | 9/2007 | Kumar et al. |
| 2007/0249946 A1 | 10/2007 | Kumar et al. |
| 2007/0255153 A1 | 11/2007 | Kumar et al. |
| 2007/0270678 A1 | 11/2007 | Fadem et al. |
| 2007/0285868 A1 | 12/2007 | Lindberg et al. |
| 2007/0293776 A1 | 12/2007 | Korzinov et al. |
| 2008/0039730 A1 | 2/2008 | Pu et al. |
| 2008/0091089 A1 | 4/2008 | Guillory et al. |
| 2008/0108890 A1 | 5/2008 | Teng et al. |
| 2008/0114232 A1 | 5/2008 | Gazit |
| 2008/0139953 A1 | 6/2008 | Baker et al. |
| 2008/0214901 A1 | 9/2008 | Gehman et al. |
| 2008/0275327 A1 | 11/2008 | Faarbaek et al. |
| 2008/0288026 A1 | 11/2008 | Cross et al. |
| 2009/0048556 A1 | 2/2009 | Durand |
| 2009/0062670 A1 | 3/2009 | Sterling et al. |
| 2009/0062671 A1 | 3/2009 | Brockway |
| 2009/0073991 A1 | 3/2009 | Landrum et al. |
| 2009/0076336 A1 | 3/2009 | Mazar et al. |
| 2009/0076340 A1 | 3/2009 | Libbus et al. |
| 2009/0076341 A1 | 3/2009 | James et al. |
| 2009/0076342 A1 | 3/2009 | Amurthur et al. |
| 2009/0076343 A1 | 3/2009 | James et al. |
| 2009/0076344 A1 | 3/2009 | Libbus et al. |
| 2009/0076345 A1 | 3/2009 | Manicka et al. |
| 2009/0076346 A1 | 3/2009 | James et al. |
| 2009/0076349 A1 | 3/2009 | Libbus et al. |
| 2009/0076350 A1 | 3/2009 | Bly et al. |
| 2009/0076364 A1 | 3/2009 | Libbus et al. |
| 2009/0076397 A1 | 3/2009 | Libbus et al. |
| 2009/0076401 A1 | 3/2009 | Mazar et al. |
| 2009/0076559 A1 | 3/2009 | Libbus et al. |
| 2009/0182204 A1 | 7/2009 | Semler et al. |
| 2009/0253975 A1 | 10/2009 | Tiegs |
| 2009/0292193 A1 | 11/2009 | Wijesiriwardana |
| 2009/0292194 A1 | 11/2009 | Libbus et al. |
| 2009/0306485 A1 | 12/2009 | Bell |
| 2010/0022864 A1 | 1/2010 | Cordero |
| 2010/0042113 A1 | 2/2010 | Mah |
| 2010/0049006 A1 | 2/2010 | Magar et al. |
| 2010/0051039 A1 | 3/2010 | Ferrara |
| 2010/0056881 A1 | 3/2010 | Libbus et al. |
| 2010/0057056 A1 | 3/2010 | Gurtner |
| 2010/0076533 A1 | 3/2010 | Dar et al. |
| 2010/0081913 A1 | 4/2010 | Cross et al. |
| 2010/0145359 A1 | 6/2010 | Keller |
| 2010/0191310 A1 | 7/2010 | Bly |
| 2010/0234716 A1 | 9/2010 | Engel |
| 2010/0249625 A1 | 9/2010 | Lin |
| 2010/0268103 A1 | 10/2010 | McNamara et al. |
| 2010/0312131 A1 | 12/2010 | Naware et al. |
| 2010/0331711 A1 | 12/2010 | Krauss et al. |
| 2011/0021937 A1 | 1/2011 | Hugh et al. |
| 2011/0087083 A1 | 4/2011 | Poeze et al. |
| 2011/0098583 A1 | 4/2011 | Pandia et al. |
| 2011/0144470 A1 | 6/2011 | Mazer et al. |
| 2011/0160601 A1 | 6/2011 | Wang et al. |
| 2011/0166468 A1 | 7/2011 | Prystowsky et al. |
| 2011/0190650 A1 | 8/2011 | McNair |
| 2011/0218415 A1 | 9/2011 | Chen |
| 2011/0237922 A1 | 9/2011 | Parker, III et al. |
| 2011/0237924 A1 | 9/2011 | McGusty et al. |
| 2011/0251504 A1 | 10/2011 | Tereshchenko et al. |
| 2011/0279963 A1 | 11/2011 | Kumar et al. |
| 2011/0306862 A1 | 12/2011 | Hayes-Gill |
| 2012/0029307 A1 | 2/2012 | Paquet et al. |
| 2012/0071730 A1 | 3/2012 | Romero |
| 2012/0071731 A1 | 3/2012 | Gottesman |
| 2012/0071743 A1 | 3/2012 | Todorov et al. |
| 2012/0083670 A1 | 4/2012 | Rotondo et al. |
| 2012/0088999 A1 | 4/2012 | Bishay et al. |
| 2012/0101396 A1 | 4/2012 | Solosko et al. |
| 2012/0108917 A1 | 5/2012 | Libbus et al. |
| 2012/0108920 A1 | 5/2012 | Bly et al. |
| 2012/0110226 A1 | 5/2012 | Vlach et al. |
| 2012/0110228 A1 | 5/2012 | Vlach et al. |
| 2012/0172676 A1 | 7/2012 | Penders et al. |
| 2012/0197150 A1 | 8/2012 | Cao et al. |
| 2012/0209102 A1 | 8/2012 | Ylotalo et al. |
| 2012/0215123 A1 | 8/2012 | Kumar et al. |
| 2012/0220835 A1 | 8/2012 | Chung |

(56) References Cited

U.S. PATENT DOCUMENTS

| | | |
|---|---|---|
| 2012/0259233 A1 | 10/2012 | Chan et al. |
| 2012/0271141 A1 | 10/2012 | Davies |
| 2012/0310070 A1 | 12/2012 | Kumar et al. |
| 2012/0323257 A1 | 12/2012 | Sutton |
| 2012/0330126 A1 | 12/2012 | Hoppe et al. |
| 2013/0041273 A1 | 2/2013 | Houben et al. |
| 2013/0046151 A1 | 2/2013 | Bsoul et al. |
| 2013/0085347 A1 | 4/2013 | Manicka et al. |
| 2013/0096395 A1 | 4/2013 | Katra et al. |
| 2013/0116533 A1 | 5/2013 | Lian et al. |
| 2013/0116585 A1 | 5/2013 | Bouguerra |
| 2013/0144146 A1 | 6/2013 | Linker |
| 2013/0150698 A1 | 6/2013 | Hsu et al. |
| 2013/0191035 A1 | 7/2013 | Chon et al. |
| 2013/0225938 A1 | 8/2013 | Vlach |
| 2013/0225967 A1 | 8/2013 | Esposito |
| 2013/0226018 A1 | 8/2013 | Kumar et al. |
| 2013/0245415 A1 | 9/2013 | Kumar et al. |
| 2013/0245472 A1 | 9/2013 | Eveland |
| 2013/0253285 A1 | 9/2013 | Bly et al. |
| 2013/0274584 A1 | 10/2013 | Finlay et al. |
| 2013/0296680 A1 | 11/2013 | Linker |
| 2013/0300575 A1 | 11/2013 | Kurzweil et al. |
| 2013/0324868 A1 | 12/2013 | Kaib et al. |
| 2013/0331663 A1 | 12/2013 | Albert et al. |
| 2013/0331665 A1 | 12/2013 | Bly et al. |
| 2013/0338448 A1 | 12/2013 | Libbus et al. |
| 2014/0012154 A1 | 1/2014 | Mazar |
| 2014/0058280 A1 | 2/2014 | Chefles et al. |
| 2014/0094676 A1 | 4/2014 | Gani et al. |
| 2014/0094709 A1 | 4/2014 | Korzinov et al. |
| 2014/0100432 A1 | 4/2014 | Golda et al. |
| 2014/0171751 A1 | 6/2014 | Sankman et al. |
| 2014/0116825 A1 | 7/2014 | Kurzweil et al. |
| 2014/0206976 A1 | 7/2014 | Thompson et al. |
| 2014/0206977 A1 | 7/2014 | Bahney et al. |
| 2014/0275827 A1 | 9/2014 | Gill et al. |
| 2014/0275928 A1 | 9/2014 | Acquista et al. |
| 2014/0303647 A1 | 10/2014 | Sepulveda et al. |
| 2014/0330136 A1 | 11/2014 | Manicka et al. |
| 2015/0022372 A1 | 1/2015 | Vosch |
| 2015/0057512 A1 | 2/2015 | Kapoor |
| 2015/0073252 A1 | 3/2015 | Mazar |
| 2015/0081959 A1 | 3/2015 | Vlach et al. |
| 2015/0082623 A1 | 3/2015 | Felix et al. |
| 2015/0087921 A1 | 3/2015 | Felix et al. |
| 2015/0087922 A1 | 3/2015 | Bardy et al. |
| 2015/0087923 A1 | 3/2015 | Bardy et al. |
| 2015/0087933 A1 | 3/2015 | Gibson et al. |
| 2015/0087948 A1 | 3/2015 | Bishay et al. |
| 2015/0087949 A1 | 3/2015 | Felix et al. |
| 2015/0087950 A1 | 3/2015 | Felix et al. |
| 2015/0087951 A1 | 3/2015 | Felix et al. |
| 2015/0088007 A1 | 3/2015 | Bardy et al. |
| 2015/0088020 A1 | 3/2015 | Dreisbach et al. |
| 2015/0094556 A1 | 4/2015 | Geva et al. |
| 2015/0173671 A1 | 6/2015 | Paalasmaa et al. |
| 2015/0193595 A1 | 7/2015 | McNamara et al. |
| 2015/0223711 A1 | 8/2015 | Raeder et al. |
| 2015/0238107 A1 | 8/2015 | Acquista et al. |
| 2015/0289814 A1 | 10/2015 | Mager et al. |
| 2015/0297134 A1 | 10/2015 | Albert et al. |
| 2015/0327781 A1 | 11/2015 | Hernandez-Silverira et al. |
| 2015/0351799 A1 | 12/2015 | Sepulveda et al. |
| 2015/0374244 A1 | 12/2015 | Yoo et al. |
| 2016/0022161 A1 | 1/2016 | Khair |
| 2016/0029906 A1 | 2/2016 | Tompkins et al. |
| 2016/0066808 A1 | 3/2016 | Hijazi |
| 2016/0085927 A1 | 3/2016 | Dettinger et al. |
| 2016/0085937 A1 | 3/2016 | Dettinger et al. |
| 2016/0086297 A1 | 3/2016 | Dettinger et al. |
| 2016/0098536 A1 | 4/2016 | Dettinger et al. |
| 2016/0098537 A1 | 4/2016 | Dettinger et al. |
| 2016/0113520 A1 | 4/2016 | Manera |
| 2016/0120433 A1 | 5/2016 | Hughes et al. |
| 2016/0120434 A1 | 5/2016 | Park et al. |
| 2016/0128597 A1 | 5/2016 | Lin et al. |
| 2016/0135746 A1 | 5/2016 | Kumar et al. |
| 2016/0157744 A1 | 6/2016 | Wu et al. |
| 2016/0166155 A1 | 6/2016 | Benet et al. |
| 2016/0192852 A1 | 7/2016 | Bozza et al. |
| 2016/0192855 A1 | 7/2016 | Geva et al. |
| 2016/0192856 A1 | 7/2016 | Lee |
| 2016/0198972 A1 | 7/2016 | Lee et al. |
| 2016/0232807 A1 | 8/2016 | Ghaffari et al. |
| 2016/0262619 A1 | 9/2016 | Marcus et al. |
| 2016/0287177 A1 | 10/2016 | Huppert et al. |
| 2016/0287207 A1 | 10/2016 | Xue |
| 2016/0296132 A1 | 10/2016 | Bojovic et al. |
| 2016/0302726 A1 | 10/2016 | Chang |
| 2016/0317048 A1 | 11/2016 | Chan et al. |
| 2016/0317057 A1 | 11/2016 | Li et al. |
| 2016/0367164 A1 | 12/2016 | Felix et al. |
| 2016/0374583 A1 | 12/2016 | Cerruti et al. |
| 2017/0042447 A1 | 2/2017 | Rossi |
| 2017/0055896 A1 | 3/2017 | Al-Ali et al. |
| 2017/0065823 A1 | 3/2017 | Kaib et al. |
| 2017/0188872 A1 | 7/2017 | Hughes et al. |
| 2017/0188971 A1 | 7/2017 | Liu |
| 2018/0146875 A1 | 5/2018 | Friedman et al. |
| 2018/0242876 A1 | 8/2018 | Hughes et al. |
| 2018/0289274 A1 | 10/2018 | Bahney et al. |
| 2018/0374576 A1 | 12/2018 | Dettinger et al. |
| 2019/0021671 A1 | 1/2019 | Kumar et al. |
| 2019/0038148 A1 | 2/2019 | Valys |
| 2019/0046066 A1* | 2/2019 | Hughes ............... A61B 5/259 |
| 2019/0167143 A1 | 6/2019 | Li et al. |
| 2019/0209022 A1* | 7/2019 | Sobol ............... A61B 5/7435 |
| 2019/0246928 A1 | 8/2019 | Bahney et al. |
| 2019/0274574 A1 | 9/2019 | Hughes et al. |
| 2019/0282178 A1 | 9/2019 | Volosin et al. |
| 2019/0290147 A1 | 9/2019 | Persen et al. |
| 2019/0298201 A1 | 10/2019 | Persen et al. |
| 2019/0298209 A1 | 10/2019 | Persen et al. |
| 2019/0298272 A1 | 10/2019 | Persen |
| 2019/0374163 A1 | 12/2019 | Faabaek et al. |
| 2020/0060563 A1* | 2/2020 | Boleyn ............... A61B 5/0022 |
| 2020/0121209 A1 | 4/2020 | Kumar et al. |
| 2020/0170529 A1 | 6/2020 | Bahney et al. |
| 2020/0178825 A1* | 6/2020 | Lu ............... A61B 5/363 |
| 2020/0178828 A1 | 6/2020 | Bahney et al. |
| 2020/0193597 A1 | 6/2020 | Fan |
| 2020/0289014 A1 | 9/2020 | Park et al. |

FOREIGN PATENT DOCUMENTS

| | | |
|---|---|---|
| CA | 2 752 154 | 8/2010 |
| CA | 2 898 626 | 7/2014 |
| CA | 2 797 980 | 8/2015 |
| CA | 2 651 203 | 9/2017 |
| CA | 2 966 182 | 6/2020 |
| CN | 102883775 | 12/2014 |
| CN | 103997955 | 11/2016 |
| CN | 303936805 | 11/2016 |
| CN | 107205679 | 9/2017 |
| EM | 001857966-000 | 5/2011 |
| EM | 003611714-000 | 1/2017 |
| EP | 0 509 689 | 4/1992 |
| EP | 1 738 686 | 6/2006 |
| EP | 1 782 729 | 5/2007 |
| EP | 1 981 402 | 10/2008 |
| EP | 2 262 419 | 12/2010 |
| EP | 2 395 911 | 12/2011 |
| EP | 2 568 878 | 3/2013 |
| EP | 2 635 179 | 9/2013 |
| EP | 2 635 180 | 9/2013 |
| EP | 2 948 050 | 12/2015 |
| EP | 2 983 593 | 2/2016 |
| EP | 3 165 161 | 5/2017 |
| EP | 3 212 061 | 9/2017 |
| EP | 3 753 483 | 12/2020 |
| GB | 2 299 038 | 9/1996 |
| GB | 2 348 707 | 10/2000 |
| IN | 002592907-000 | 12/2014 |

(56) References Cited

FOREIGN PATENT DOCUMENTS

| | | |
|---|---|---|
| JP | S61-137539 | 6/1986 |
| JP | H08-317913 | 3/1996 |
| JP | 2000-126145 | 5/2000 |
| JP | 2001-057967 | 3/2001 |
| JP | 2004-121360 | 4/2004 |
| JP | 2007-045967 | 2/2007 |
| JP | 2007-503910 | 3/2007 |
| JP | 2007-504917 | 3/2007 |
| JP | 2007-097822 | 4/2007 |
| JP | 2007-296266 | 11/2007 |
| JP | 2009-518099 | 5/2009 |
| JP | 2009-525816 | 7/2009 |
| JP | 2011-519583 | 7/2011 |
| JP | 2013-521966 | 6/2013 |
| JP | 5203973 | 6/2013 |
| JP | 1483906 S | 10/2013 |
| JP | 5559425 | 7/2014 |
| JP | 2014-236982 | 12/2014 |
| JP | 2016-504159 | 2/2016 |
| JP | 2013-517053 | 5/2016 |
| JP | 2017-136380 | 8/2017 |
| JP | 6198849 | 9/2017 |
| JP | 6336640 | 5/2018 |
| JP | D1596476 | 8/2018 |
| JP | 2018-153651 | 10/2018 |
| JP | 6491826 | 3/2019 |
| JP | 6495228 | 3/2019 |
| JP | 2020-058819 | 4/2020 |
| JP | 6766199 | 9/2020 |
| KR | 3003784570000 | 3/2005 |
| KR | 10-1513288 | 4/2015 |
| KR | 3008476060000 | 3/2016 |
| KR | 3008476090000 | 3/2016 |
| KR | 3008482960000 | 3/2016 |
| KR | 3008584120000 | 6/2016 |
| KR | 3008953750000 | 2/2017 |
| KR | 3008953760000 | 2/2017 |
| KR | 3008987790000 | 3/2017 |
| KR | 3009445870000 | 2/2018 |
| KR | 3009547690000 | 4/2018 |
| KR | 3009547710000 | 4/2018 |
| WO | WO 99/023943 | 5/1999 |
| WO | WO 01/016607 | 3/2001 |
| WO | WO 2004/100785 | 11/2004 |
| WO | WO 2005/025668 | 3/2005 |
| WO | WO 2005/037946 | 4/2005 |
| WO | WO 2005/084533 | 9/2005 |
| WO | WO 2006/094513 | 9/2006 |
| WO | WO 2007/049080 | 3/2007 |
| WO | WO 2007/036748 | 4/2007 |
| WO | WO 2007/063436 | 6/2007 |
| WO | WO 2007/071180 | 6/2007 |
| WO | WO 2007/072069 | 6/2007 |
| WO | WO 2007/092543 | 8/2007 |
| WO | WO 2008/005015 | 1/2008 |
| WO | WO 2008/005016 | 1/2008 |
| WO | WO 2008/057884 | 5/2008 |
| WO | WO 2008/120154 | 10/2008 |
| WO | WO 2009/055397 | 4/2009 |
| WO | WO 2009/074928 | 6/2009 |
| WO | 2009/112972 | 9/2009 |
| WO | WO 2009/112976 | 9/2009 |
| WO | WO 2009/112979 | 9/2009 |
| WO | WO 2009/134826 | 11/2009 |
| WO | WO 2010/014490 | 2/2010 |
| WO | WO 2010/104952 | 9/2010 |
| WO | WO 2010/105203 | 9/2010 |
| WO | WO 2010/093900 | 10/2010 |
| WO | WO 2011/077097 | 6/2011 |
| WO | 2014/055994 | 7/2011 |
| WO | WO/2011112420 | 9/2011 |
| WO | 2011/084636 | 10/2011 |
| WO | WO 2011/143490 | 11/2011 |
| WO | WO 2011/149755 | 12/2011 |
| WO | WO 2012/009453 | 1/2012 |
| WO | WO 2012/061509 | 5/2012 |
| WO | WO 2012/061518 | 5/2012 |
| WO | WO 2012/125425 | 9/2012 |
| WO | WO 2012/160550 | 11/2012 |
| WO | WO 2014/047032 | 3/2014 |
| WO | WO 2014/051563 | 4/2014 |
| WO | WO 2014/055994 | 4/2014 |
| WO | WO 2014/116825 | 7/2014 |
| WO | WO 2014/168841 | 10/2014 |
| WO | WO 2016/044514 | 3/2016 |
| WO | WO 2016/044515 | 3/2016 |
| WO | WO 2016/044519 | 3/2016 |
| WO | WO 2016/057728 | 4/2016 |
| WO | WO 2016/070128 | 5/2016 |
| WO | WO 2016/181321 | 11/2016 |
| WO | WO 2017/039518 | 3/2017 |
| WO | WO 2017/041014 | 3/2017 |
| WO | WO 2019/191487 | 10/2019 |
| WO | WO 2020/013895 | 1/2020 |
| WO | WO 2020/041363 | 2/2020 |

OTHER PUBLICATIONS

U.S. Appl. No. 15/005,854, filed Jan. 25, 2016, Kumar et al.
3M Corporation, "3M Surgical Tapes—Choose the Correct Tape" quicksheet (2004).
Altini, et al., An ECG Patch Combining a Customized Ultra-Low-Power ECG SOC With Bluetooth Low Energy for Long Term Ambulatory Monitoring, Conference: Proceddings of Wireless Health 2011, WH 2011, Oct. 10-13, 2011.
British-Made Early Warning Monitor a "Game Changer", healthcare-in-europe.com, Mar. 31, 2014.
Comstock, Proteus Digital Health Quietly Launches Consumer-Facing Wearable for Athletes, Mobile Health News, Oct. 29, 2014.
Coxworth, Small Adhesive Partch Outperforms Traditional Tech for Detecting Arrhythmia, Scripps, iRhythm Technologies, Jan. 3, 2014.
Del Mar et al.; The history of clinical holter monitoring; A.N.E.; vol. 10; No. 2; pp. 226-230; Apr. 2005.
Enseleit et al.; Long-term continuous external electrocardiographic recording: a review; Eurospace; vol. 8; pp. 255-266; 2006.
Hoefman et al.; Optimal duration of event recording for diagnosis of arrhythmias in patients with palpitations and light-headedness in the general practice; Family Practice; Dec. 7, 2006.
Kennedy et al.; The history, science, and innovation of holter technology; A.N.E.; vol. 11; No. 1; pp. 85-94; 2006.
"Mayo Alumni", Mayo Clinic, Rochester, MN, Spring 2011, in 24 pages.
Medtronic Launches Seeq Wearable Cardiac Monitoring System in United States, Diagnostic and Interventional Cardiology, Oct. 7, 2014.
Mundt et al. "A Multiparameter Wearable Physiologic Monitoring System for Space and Terrestrial Applications" IEEE Transactions on Information Technology in Biomedicine, vol. 9, No. 3, pp. 382-384, Sep. 2005.
Prakash, New Patch-Based Wearable Sensor Combines Advanced Skin Adhesives and Sensor Technologies, Advantage Business Marketing, Jul. 17, 2012.
Reiffel et al.; Comparison of autotriggered memory loop recorders versus standard loop recorders versus 24-hour holter monitors for arrhythmia detection; Am. J. Cardiology; vol. 95; pp. 1055-1059; May 1, 2005.
Request for Reexamination of U.S. Pat. No. 7,020,508 under 35 U.S.C. §§ 311-318 and 37 C.F.R. § 1.913 as submitted Sep. 14, 2012 in 78 pages.
Scapa Medical product listing and descriptions (2008) available at http://www.caapana.com/productlist.jsp and http://www.metplus.co.rs/pdf/prospekti/Samolepljivemedicinsketrake.pdf; retrieved via WayBack Machine Sep. 24, 2012.
Strong, Wearable Technologies Conference 2013 Europe—Notes and Roundup, Wearable Technologies Conference, Feb. 8, 2013.
Sumner, Stanford Engineers Monitor Heart Health Using Paper-Thin Flexible 'Skin', Stanford Report, May 14, 2013.

(56) References Cited

OTHER PUBLICATIONS

Ward et al.; Assessment of the diagnostic value of 24-hour ambulatory electrocardiographic monitoring; Biotelemetry Patient monitoring; vol. 7; 1980.
Ziegler et al.; Comparison of continuous versus intermittent monitoring of atrial arrhythmias; Heart Rhythm; vol. 3; No. 12; pp. 1445-1452; Dec. 2006.
Zimetbaum et al.; The evolving role of ambulatory arrhythmia monitoring in general clinic practice; Ann. Intern. Med.; vol. 130; pp. 846-8556; 1999.
Zimetbaum et al.; Utility of patient-activated cardiac event recorders in general clinical practice; The Amer. J. of Cardiology; vol. 79; Feb. 1, 1997.
PCT Search Report dated May 6, 2021 for International Patent Application No. PCT/US2021/017667.

\* cited by examiner

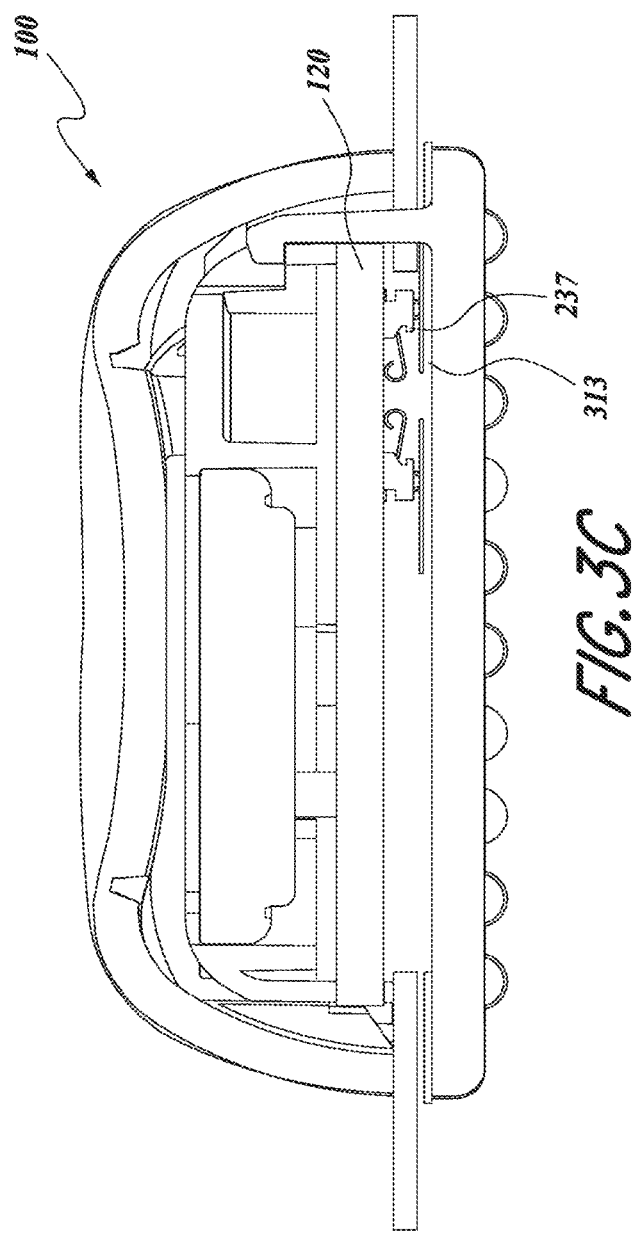

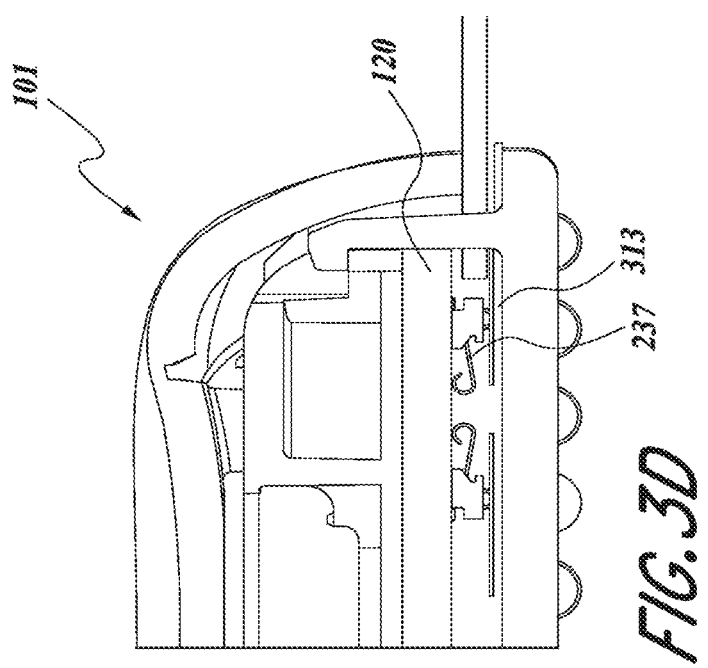

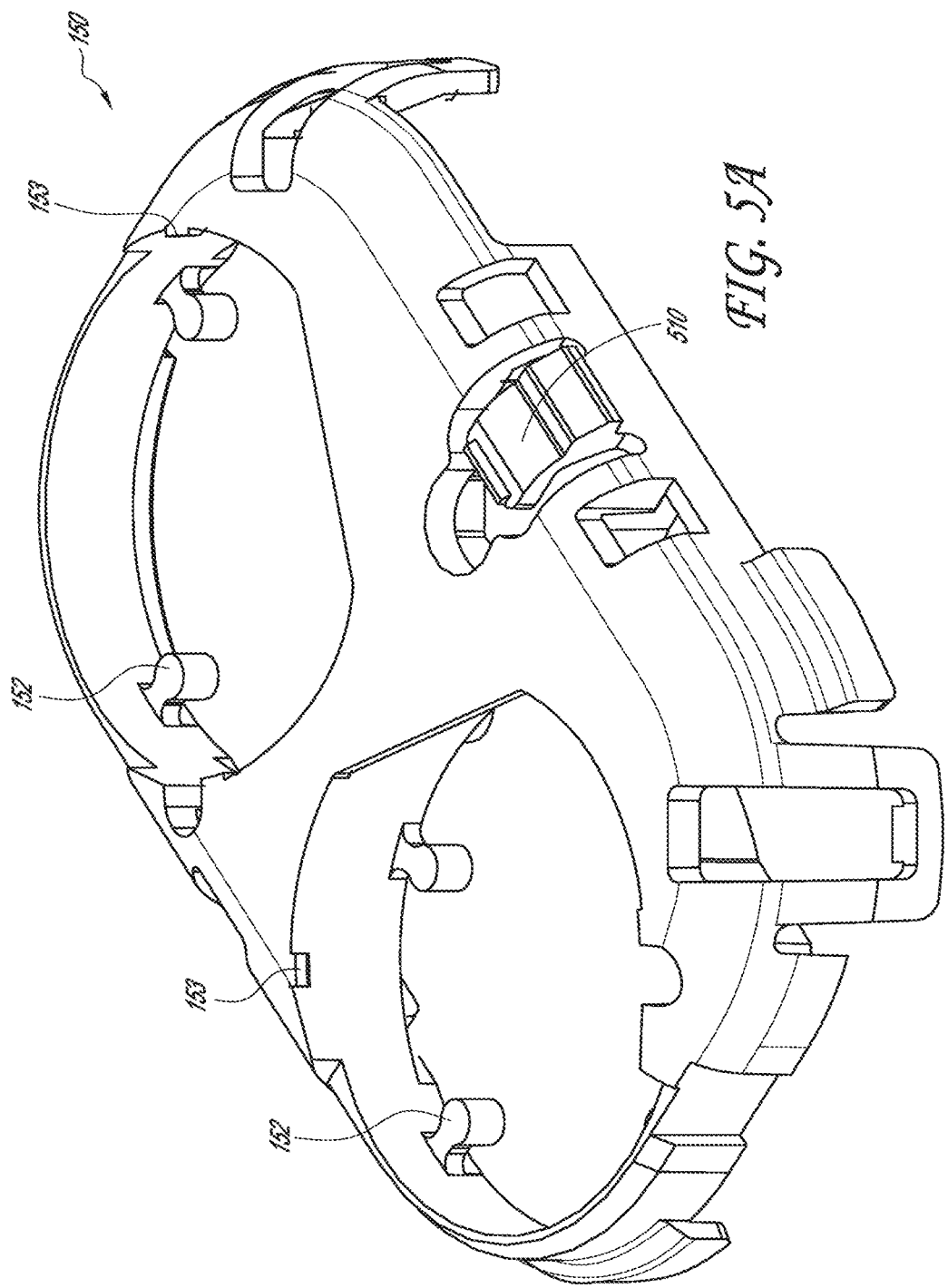

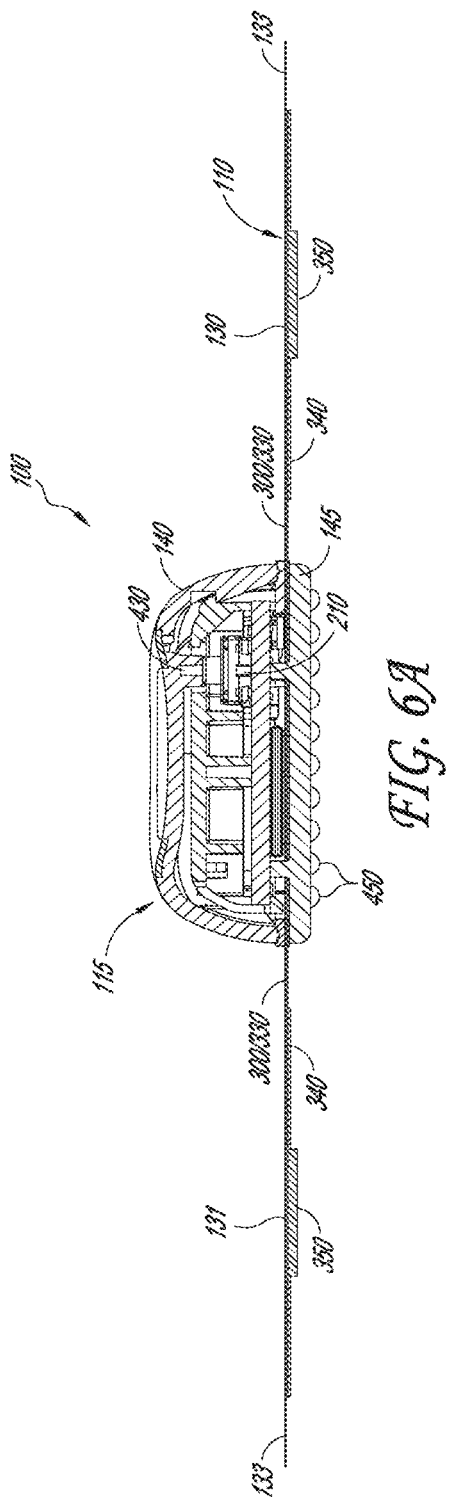

- Less Computations on the Device
- Longer Battery Life
- Smaller Form Factor
- Can Make More Predictions
- Higher Accuracy
- Lower False Alarms
- Smaller Memory to Store/Update Neural Network Instructions
- Process Layers Agnostic to Wearable Device Limitations

METHODS AND SYSTEMS FOR PROCESSING DATA VIA AN EXECUTABLE FILE ON A MONITOR TO REDUCE THE DIMENSIONALITY OF THE DATA AND ENCRYPTING THE DATA BEING TRANSMITTED OVER THE WIRELESS NETWORK

CROSS-REFERENCE TO RELATED APPLICATIONS

This application claims priority from provisional U.S. Pat. App. No. 62/975,626, filed on Feb. 12, 2020 and from provisional U.S. Pat. App. No. 63/090,951, filed on Oct. 13, 2020, which is hereby incorporated by reference in its entirety.

BACKGROUND

For purposes of this disclosure, certain aspects, advantages, and novel features of various embodiments are described herein. It is to be understood that not necessarily all such advantages may be achieved in accordance with any particular embodiment. Thus, various embodiments may be or carried out in a manner that achieves one advantage or group of advantages as taught herein without necessarily achieving other advantages as may be taught or suggested herein.

BRIEF SUMMARY OF EMBODIMENTS

Embodiments described herein are directed to a physiological monitoring device that may be worn continuously and comfortably by a human or animal subject for at least one week or more and more typically two to three weeks or more. In one embodiment, the device is specifically designed to sense and record cardiac rhythm (for example, electrocardiogram, ECG) data, although in various alternative embodiments one or more additional physiological parameters may be sensed and recorded. Such physiological monitoring devices may include a number of features to facilitate and/or enhance the patient experience and to make diagnosis of cardiac arrhythmias more accurate and timely.

Some embodiments include a wearable cardiac monitor device for monitoring cardiac rhythm signal data of a user, the wearable cardiac monitor device comprising: a watertight housing; a surface on the housing configured to be sealably engaged to a mammal; an adhesive on the surface configured to remain continuously affixed to the mammal for at least 7 days, without removal until completion of monitoring; at least two electrodes permanently disposed within the housing, positioned to detect continuous cardiac rhythm signals of the mammal while the surface is sealably engaged to the mammal; a hardware processor configured to process the detected cardiac rhythm signals through a first subset of computer-executable instructions; and a transmitter, the transmitter configured to transmit the output of the first subset to a computing system, the computing system configured to infer a likelihood of an occurrence of cardiac arrhythmia by processing the output through a second subset of computer-executable instructions.

In some embodiments, the arrhythmia comprises at least one of: ventricular tachycardia, supraventricular tachycardia, ectopy, ventricular fibrillation, or extended pauses.

In some embodiments, to infer a likelihood of an occurrence of cardiac arrhythmia comprises processing the output of the first subset through the second subset, wherein the first subset processed at least 24 hours of continuously detected, stored cardiac rhythm signals.

In some embodiments, the housing comprises a patient trigger configured to depress and initiate recordation of an instance in time of a perceived cardiac event.

In some embodiments, the electrodes are disposed entirely within the housing.

In some embodiments, the first subset of computer-executable instructions comprise a first subset of layers of a neural network, wherein the second subset of computer-executable instructions comprise a second subset of layers of the neural network.

Some embodiments include a wearable cardiac monitor device for monitoring bio-signal data of a user, the wearable device comprising: an adhesive assembly comprising a housing and a wing, the wing comprising an electrode configured to detect cardiac signals from a user; a hardware processor configured to process the detected cardiac signals through a first subset of layers of a neural network; and a transmitter, the transmitter configured to transmit the output of the first subset to a computing system, the computing system configured to infer a likelihood of an occurrence of cardiac arrhythmia by processing the output through a second subset of layers of the neural network.

In some embodiments, the computing system is further configured to determine an atrial fibrillation burden from the detected cardiac signals.

In some embodiments, the atrial fibrillation burden comprises an amount of time spent in atrial fibrillation by the user during a period of time.

In some embodiments, the atrial fibrillation burden comprises an amount of time spent in atrial fibrillation by the user during a sleep period and during a wake period.

Some embodiments include a wearable device for monitoring bio-signal data of a user, the wearable device comprising: an assembly comprising an electrode configured to detect cardiac signals from a user; a hardware processor configured to process the detected cardiac signals through a first subset of layers of a neural network; and a transmitter, the transmitter configured to transmit the output of the first subset to a computing system, the computing system configured to infer a likelihood of an occurrence of cardiac arrhythmia by processing the output through a second subset of layers of the neural network.

In some embodiments, the hardware processor is configured to process the detected cardiac signals through the first subset of layers of the neural network continuously in substantially real-time of detecting ECG signals.

In some embodiments, the output of the first subset of layers of the neural network comprises an indication of an R peak.

In some embodiments, the computing system is further configured to reconstruct the cardiac signals via the second subset of layers.

In some embodiments, the output of the first subset of layers of the neural network is of a smaller dimensionality than the input of the first subset of layers of the neural network.

In some embodiments, the hardware processor is configured to select the neural network from a plurality of neural networks based on a characteristic.

In some embodiments, the characteristic comprises at least one of: a characteristic of the wearable device, a network characteristic between the wearable device and the computing system.

In some embodiments, the hardware processor is further configured to compress the output of the first subset of layers of the neural network, wherein to transmit the output of the first subset to the computing system comprises transmitting the compressed output, wherein the computing system is configured to decompress the transmitted data; and wherein processing the output through the second subset of layers comprises processing the decompressed data.

In some embodiments, the hardware processor is further configured to quantize the output of the first subset of layers of the neural network, wherein to transmit the output of the first subset to the computing system comprises transmitting the output.

In some embodiments, the hardware processor is further configured to compress the quantized output, wherein to transmit the output of the first subset to the computing system comprises transmitting the compressed output, wherein the computing system is configured to decompress the transmitted data; and wherein processing the output through the second subset of layers comprises processing the decompressed data.

In some embodiments, to transmit the output of the first subset to the computing system comprises transmitting the quantized output.

Some embodiments include a monitor to infer a likelihood of a characteristic of a user, the monitor comprising: a housing; at least two electrodes permanently disposed within the housing, positioned to detect continuous signals of a surface; a printed circuit board assembly comprising a hardware processor configured to process the detected signals through a first subset of computer executable instructions; and a transmitter, the transmitter configured to transmit the data output of the first subset of computer executable instructions to a computing system, the computing system configured to infer a likelihood of an occurrence by processing the data output through a second subset of computer executable instructions.

In some embodiments, the dimensionality of the data output of the first subset of the computer executable instructions that is transmitted to the computing system is smaller than the data of the detected signals from the at least two electrodes.

In some embodiments, the data output of the first subset of the computer executable instructions is encrypted, wherein the transmitter transmits the encrypted data output, wherein the computing system processes the encrypted data output through the second subset of computer executable instructions.

In some embodiments, the transmitter transmits the data output to the computing system via a wireless communication channel.

In some embodiments, the monitor further comprises a receiver configured to receive an updated first subset of computer executable instructions from the computing system and updating the first subset of the computer executable instructions to the updated first subset of computer executable instructions, wherein the hardware processor is further configured to process signals through the updated first subset of computer executable instructions.

In some embodiments, the monitor further comprises an accelerometer configured to gather motion data, wherein the computing system is configured to match motion data with the detected signals to infer the likelihood of the occurrence.

In some embodiments, the monitor is a cardiac monitor, wherein the continuous signals are cardiac signals, wherein the occurrence is an arrhythmia event.

In some embodiments, the first subset of computer executable instructions comprise a first subset of layers of a neural network, and the second subset of computer executable instructions comprise a second subset of layers of the neural network.

Some embodiments include a monitor to infer a likelihood of a characteristic of a user, the monitor comprising: a watertight housing; a surface on the housing configured to be sealably engaged to a mammal; an adhesive on the surface configured to remain continuously affixed to the mammal for at least 7 days, without removal until completion of monitoring; at least two electrodes permanently disposed within the housing, positioned to detect continuous cardiac rhythm signals of the mammal while the surface is sealably engaged to the mammal; a printed circuit board assembly comprising a hardware processor configured to process the detected cardiac rhythm signals through a first subset of computer executable instructions; and a transmitter, the transmitter configured to transmit the data output of the first subset of computer executable instructions to a computing system, the computing system configured to infer a likelihood of an occurrence of arrhythmia by processing the data output through a second subset of computer executable instructions.

In some embodiments, the arrhythmia comprises at least one of: ventricular tachycardia, supraventricular tachycardia, ectopy, ventricular fibrillation, or extended pauses.

In some embodiments, to infer a likelihood of an occurrence of cardiac arrhythmia comprises processing the output of the first subset through the second subset, wherein the first subset processed at least 24 hours of continuously detected, stored cardiac rhythm signals.

In some embodiments, the housing comprises a patient trigger configured to depress and initiate recordation of an instance in time of a perceived cardiac event.

Some embodiments include a system for training a neural network to infer a likelihood of a characteristic of a user, the system comprising: a wearable device comprising: an assembly comprising an electrode configured to detect cardiac signals from a user; a hardware processor configured to process the detected cardiac signals through a first subset of layers of a neural network; and a transmitter, the transmitter configured to transmit the output of the first subset to a computing system, the computing system configured to infer a likelihood of an occurrence of cardiac arrhythmia by processing the output through a second subset of layers of the neural network, wherein the system is configured to train the neural network by: training a first neural network to identify a first feature by processing first training data of a first time period through the first neural network; freezing weights of the first neural network; training a second neural network to identify a second feature by processing second training data of a second time period through the first and second neural network, wherein the second time period is longer than the first time period; unfreezing weights of the first neural network; and training the first and second neural network simultaneously to identify the second feature by processing third training data of a third time period through the first and second neural network, wherein the third time period is longer than the first time period.

In some embodiments, the output of the first subset of layers of the neural network is of a smaller dimensionality than the input of the first subset of layers of the neural network.

In some embodiments, the hardware processor is configured to select the neural network from a plurality of neural networks based on a characteristic.

In some embodiments, the characteristic comprises at least one of: a characteristic of the wearable device, a network characteristic between the wearable device and the computing system.

In some embodiments, the hardware processor is further configured to compress the output of the first subset of layers of the neural network, wherein to transmit the output of the first subset to the computing system comprises transmitting the compressed output, wherein the computing system is configured to decompress the transmitted data; and wherein processing the output through the second subset of layers comprises processing the decompressed data.

In some embodiments, the hardware processor is further configured to quantize the output of the first subset of layers of the neural network, wherein to transmit the output of the first subset to the computing system comprises transmitting the output.

Some embodiments include a method for training a neural network to infer a likelihood of a characteristic of a user, the method comprising: training a first neural network to identify a first feature by processing first training data of a first time period through the first neural network; freezing weights of the first neural network; training a second neural network to identify a second feature by processing second training data of a second time period through the first and second neural network, wherein the second time period is longer than the first time period; unfreezing weights of the first neural network; and training the first and second neural network simultaneously to identify the second feature by processing third training data of a third time period through the first and second neural network, wherein the third time period is longer than the first time period.

In some embodiments, the second training data is the third training data, and the second time period is the third time period.

In some embodiments, training is based on available processing power of a wearable device.

In some embodiments, training is based on available memory of a wearable device.

In some embodiments, training is based on network availability between a wearable device and an external computing system.

In some embodiments, training is based on a type of the characteristic of the user.

In some embodiments, the type of the characteristic of the user includes an occurrence of cardiac arrhythmia.

In certain embodiments, the computing system is further configured to provide a report, the report comprising the likelihood of the occurrence of cardiac arrhythmia.

In certain embodiments, the report comprises a graph over time of atrial fibrillation burden.

In certain embodiments, the report comprises indications for a presence of atrial fibrillation.

In certain embodiments, the report comprises at least a 14 day monitoring period.

In certain embodiments, the computing system is a server or a gateway.

In certain embodiments, the computing system is a smartphone.

In certain embodiments, the computing system communicates with the transmitter through a smartphone intermediary.

In certain embodiments, the wearable device is configured to collect a secondary signal and the hardware processor is configured to process the secondary signal through the first subset of layers of the neural network.

In certain embodiments, the wearable device further comprises an accelerometer configured to measure movement of the user, and wherein the secondary signal is accelerometer data.

In certain embodiments, the computing system is further configured to determine an atrial fibrillation burden, and the atrial fibrillation burden comprises an amount of time spent in atrial fibrillation during movement of the user.

In certain embodiments, the movement of the user comprises a first degree of movement and a second degree of movement.

In certain embodiments, the secondary signal is electrode contact quality data.

In certain embodiments, the electrodes and hardware processor are contained within a chest strap.

In certain embodiments, the electrodes and hardware processor are contained within a watch, configured to be worn on a human wrist.

In certain embodiments, the electrodes and hardware processor are contained within a wearable fitness band.

In certain embodiments, the arrhythmia comprises ventricular tachycardia.

In certain embodiments, the arrhythmia comprises supraventricular tachycardia.

In certain embodiments, the arrhythmia comprises ectopy.

In certain embodiments, the arrhythmia comprises ventricular fibrillation.

In certain embodiments, the arrhythmia comprises extended pauses.

In certain embodiments, the hardware processor is configured to be removed from the wearable device and modified while removed from the wearable device.

In certain embodiments, to quantize the output comprises rounding or truncating the values in the output.

In certain embodiments, the amount of quantization to the output is based on lossless compression performance.

In certain embodiments, the amount of quantization to the output is based on an efficiency on at least one of: processing power, storage, or network usage, and accuracy of the neural network.

In certain embodiments, the neural network is trained by applying quantization to the output of the first subset of layers of the neural network.

In certain embodiments, the neural network is trained by applying lossless compression to the output of the first subset of layers of the neural network.

In certain embodiments, the neural network is trained by applying quantization and lossless compression to the output of the first subset of layers of the neural network.

In certain embodiments, the neural network is trained without quantization and lossless compression to generate a first neural network, and the first neural network is trained by applying quantization and lossless compression to the output of the first subset of layers of the neural network to generate a second neural network.

Some embodiments include a wearable device for monitoring data, the wearable device comprising: a sensor configured to detect cardiac signals from a user; a hardware processor configured to process the detected cardiac signals through a first subset of layers of a neural network; and a transmitter, the transmitter configured to transmit the output of the first subset to a computing system, the computing system configured to infer a likelihood of an occurrence of cardiac arrhythmia by processing the output through a second subset of layers of the neural network.

Some embodiments include a computing system for estimating a likelihood of an occurrence of cardiac arrhythmia, the computing system comprising: one or more first hardware processors configured to: receive data from a wearable device, wherein the wearable device comprises a sensor configured to detect cardiac signals from a user, and one or more second hardware processors configured to process the detected cardiac signals through a first subset of layers of a neural network; process the received data through a second subset of layers of the neural network; and receive, from the output of the second subset of layers, an inference of a likelihood of an occurrence of cardiac arrhythmia.

Some embodiments include a method for monitoring data, the method comprising: detecting cardiac signals from a user; processing the detected cardiac signals through a first subset of layers of a neural network; and transmitting the output of the first subset to a computing system, the computing system inferring a likelihood of an occurrence of cardiac arrhythmia by processing the output through a second subset of layers of the neural network.

Some embodiments include a non-transitory computer storage medium storing computer-executable instructions that, when executed by a processor, cause the processor to perform the following method: detecting cardiac signals from a user; processing the detected cardiac signals through a first subset of layers of a neural network; and transmitting the output of the first subset to a computing system, the computing system inferring a likelihood of an occurrence of cardiac arrhythmia by processing the output through a second subset of layers of the neural network.

Some embodiments include a method for training a neural network to infer a likelihood of a characteristic of a user, the method comprising: training a first neural network to identify a first feature by processing first training data of a first time period through the first neural network; freezing weights of the first neural network; training a second neural network to identify a second feature by processing second training data of a second time period through the first and second neural network, wherein the second time period is longer than the first time period; unfreezing weights of the first neural network; and training the first and second neural network simultaneously to identify the second feature by processing third training data of a third time period through the first and second neural network, wherein the third time period is longer than the first time period.

In certain embodiments, the second training data is the third training data, and the second time period is the third time period.

In certain embodiments, training is based on available processing power of a wearable device.

In certain embodiments, training is based on available memory of a wearable device.

In certain embodiments, training is based on network availability between a wearable device and an external computing system.

In certain embodiments, training is based on a type of the characteristic of the user.

In certain embodiments, the type of the characteristic of the user includes an occurrence of cardiac arrhythmia.

Some embodiments include a system for training a neural network to infer a likelihood of a characteristic of a user, the system comprising: a wearable cardiac monitor device comprising: a watertight housing; a surface on the housing configured to be sealably engaged to a mammal; an adhesive on the surface configured to remain continuously affixed to the mammal for at least 7 days, without removal until completion of monitoring; at least two electrodes permanently disposed within the housing, positioned to detect continuous cardiac rhythm signals of the mammal while the surface is sealably engaged to the mammal; a hardware processor configured to process the detected cardiac rhythm signals through a first subset of layers of a neural network; and a transmitter, the transmitter configured to transmit the output of the first subset to a computing system, the computing system configured to infer a likelihood of an occurrence of cardiac arrhythmia by processing the output through a second subset of layers of the neural network, wherein the system is configured to train the neural network by: training a first neural network to identify a first feature by processing first training data of a first time period through the first neural network; freezing weights of the first neural network; training a second neural network to identify a second feature by processing second training data of a second time period through the first and second neural network, wherein the second time period is longer than the first time period; unfreezing weights of the first neural network; and training the first and second neural network simultaneously to identify the second feature by processing third training data of a third time period through the first and second neural network, wherein the third time period is longer than the first time period.

Some embodiments include a wearable device for monitoring bio-signal data of a user, the wearable device comprising: an adhesive assembly comprising a housing and a wing, the wing comprising an electrode configured to detect cardiac signals from a user; a hardware processor configured to process the detected cardiac signals through a first subset of layers of a neural network; and a transmitter, the transmitter configured to transmit the output of the first subset to a computing system, the computing system configured to infer a QT interval by processing the output through a second subset of layers of the neural network.

In certain embodiments, the computing system is further configured to determine an atrial fibrillation burden from the detected cardiac signals.

In certain embodiments, the atrial fibrillation burden comprises an amount of time spent in atrial fibrillation by the user during a period of time.

In certain embodiments, the atrial fibrillation burden comprises an amount of time spent in atrial fibrillation by the user during a sleep period and during a wake period.

In certain embodiments, the hardware processor is configured to process the detected cardiac signals through the first subset of layers of the neural network continuously in substantially real-time of detecting ECG signals.

In certain embodiments, the output of the first subset of layers of the neural network comprises an indication of an R peak.

In certain embodiments, the computing system is further configured to reconstruct the cardiac signals via the second subset of layers.

Some embodiments include a system for training a neural network to infer a likelihood of a characteristic of a user, the system comprising: a wearable device comprising: an assembly comprising an electrode configured to detect cardiac signals from a user; a hardware processor configured to process the detected cardiac signals through a first subset of layers of a neural network; and a transmitter, the transmitter configured to transmit the output of the first subset to a computing system, the computing system configured to infer a likelihood of an occurrence of cardiac arrhythmia by processing the output through a second subset of layers of the neural network, wherein the system is configured to train the neural network by: training a first neural network to identify a first feature by processing first training data of a first time period through the first neural network; freezing weights of the first neural network; training a second neural network to identify a second feature by processing second training data of a second time period through the first and second neural network, wherein the second time period is longer than the first time period; unfreezing weights of the first neural network; and training the first and second neural network simultaneously to identify the second feature by processing third training data of a third time period through the first and second neural network, wherein the third time period is longer than the first time period.

In certain embodiments, the output of the first subset of layers of the neural network is of a smaller dimensionality than the input of the first subset of layers of the neural network.

In certain embodiments, the hardware processor is configured to select the neural network from a plurality of neural networks based on a characteristic.

In certain embodiments, the characteristic comprises at least one of: a characteristic of the wearable device, a network characteristic between the wearable device and the computing system.

In certain embodiments, the hardware processor is further configured to compress the output of the first subset of layers of the neural network, wherein to transmit the output of the first subset to the computing system comprises transmitting the compressed output, wherein the computing system is configured to decompress the transmitted data; and wherein processing the output through the second subset of layers comprises processing the decompressed data.

In certain embodiments, the hardware processor is further configured to quantize the output of the first subset of layers of the neural network, wherein to transmit the output of the first subset to the computing system comprises transmitting the output.

In certain embodiments, the computing system infers the QT interval by reconstructing the ECG signal from the output of the second subset of layers of the neural network.

In certain embodiments, the computing system infers the QT interval based on an average QT interval from a window of encoded features that include a plurality of QT intervals.

Some embodiments include a wearable device for monitoring bio-signal data of a user, the wearable device comprising: an adhesive assembly comprising a housing and a wing, the wing comprising an electrode configured to detect cardiac signals from a user; a hardware processor configured to process the detected cardiac signals through a first subset of layers of a neural network; and a transmitter, the transmitter configured to transmit the output of the first subset to a computing system, the computing system configured to generate a template beat based on a plurality of beats over a period of time.

Some embodiments include a wearable device for monitoring bio-signal data of a user, the wearable device comprising: an assembly comprising an electrode configured to detect cardiac signals from a user; a hardware processor configured to process the detected cardiac signals through a first subset of layers of a neural network, the output of the first subset of layers of the neural network comprises RR peak intervals, wherein an RR peak interval comprises a duration between two consecutive R-peaks; and a transmitter, the transmitter configured to transmit the output of the first subset to a computing system, the computing system configured to infer a likelihood of an occurrence of cardiac arrhythmia by processing the RR peak intervals in the output of the first subset of layers of the neural network through a second subset of layers of the neural network.

In certain embodiments, first subset of layers of the neural network generates a sequence of RR peak intervals by extracting RR-interval sub-sequences using an overlapping sliding window and shifting the sliding window on the detected cardiac signals.

These and other aspects and embodiments of the invention are described in greater detail below, with reference to the drawing figures.

BRIEF DESCRIPTION OF THE DRAWINGS

FIGS. 3A, 3B, 3C, 3D, and 3E are perspective and exploded views of a flexible body and gasket of the physiological monitoring device, according to one embodiment.

FIGS. 5A and 5B provide a perspective view of a battery holder of the physiological monitoring device, according to one embodiment.

FIGS. 6A and 6B are cross sectional views of the physiological monitoring device, according to one embodiment.

DETAILED DESCRIPTION OF EMBODIMENTS

Figure 1A:
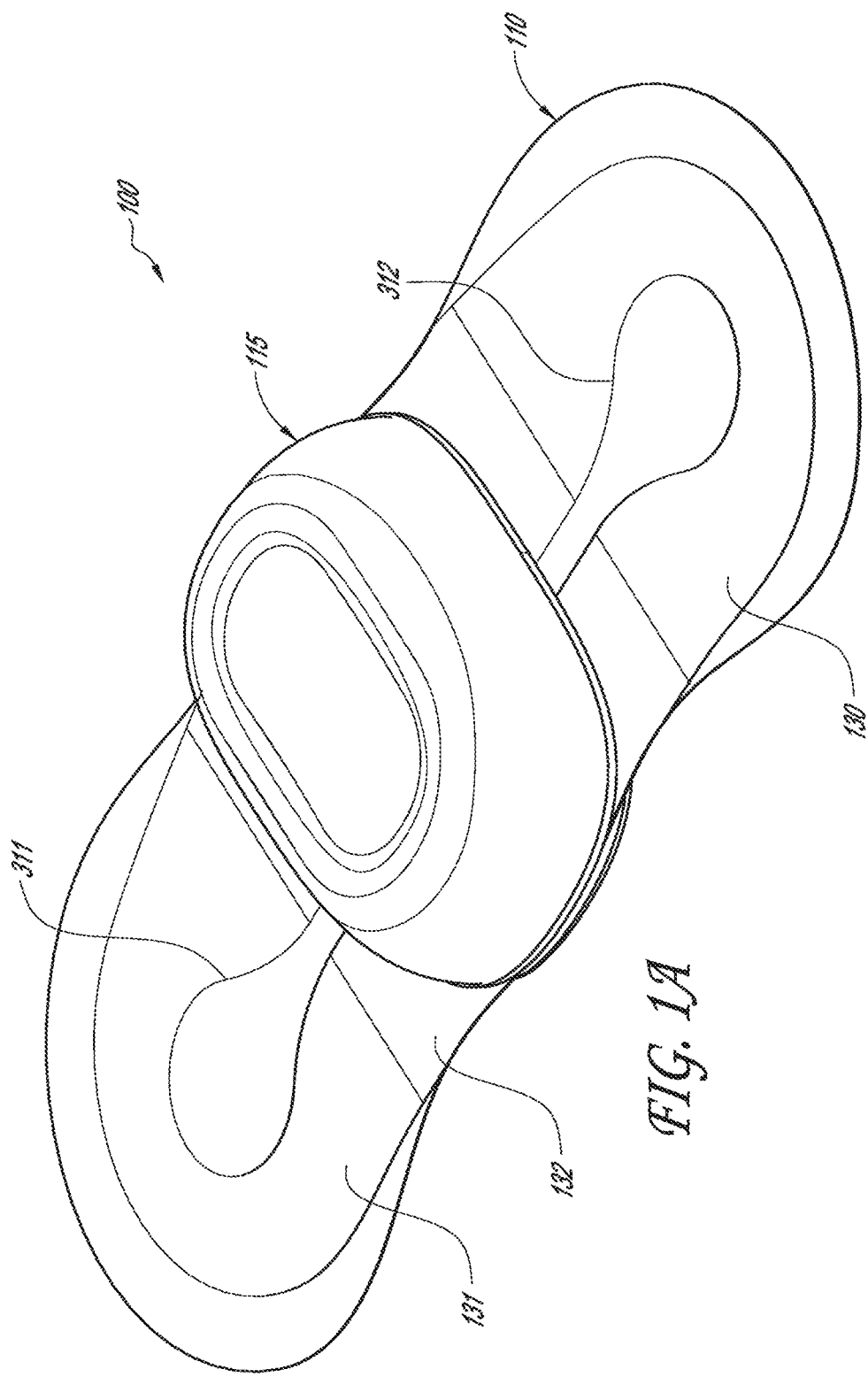
FIGS. 1A and 1B are perspective and exploded profile views, respectively, of a physiological monitoring device, according to one embodiment.

The following description is directed to a number of various embodiments. The described embodiments, however, may be implemented and/or varied in many different ways. For example, the described embodiments may be implemented in any suitable device, apparatus, or system to monitor any of a number of physiological parameters. For example, the following discussion focuses primarily on long-term, patch-based cardiac rhythm monitoring devices. In one alternative embodiment, a physiological monitoring device may be used, for example, for pulse oximetry and diagnosis of obstructive sleep apnea. The method of using a physiological monitoring device may also vary. In some cases, a device may be worn for one week or less, while in other cases, a device may be worn for at least seven days and/or for more than seven days, for example between fourteen days and twenty-one days or even longer.

Since abnormal heart rhythms or arrhythmias can often be due to other, less serious causes, a key challenge is to determine when any of these symptoms are due to an arrhythmia. Oftentimes, arrhythmias occur infrequently and/or episodically, making rapid and reliable diagnosis difficult. Currently, cardiac rhythm monitoring is primarily accomplished through the use of devices, such as Holter monitors, that use short-duration (less than 1 day) electrodes affixed to the chest. Wires connect the electrodes to a recording device, usually worn on a belt. The electrodes need daily changing and the wires are cumbersome. The devices also have limited memory and recording time. Wearing the device interferes with patient movement and often precludes performing certain activities while being monitored, such as bathing. Further, Holter monitors are capital equipment with limited availability, a situation that often leads to supply constraints and corresponding testing delays. These limitations severely hinder the diagnostic usefulness of the device, the compliance of patients using the device, and the likelihood of capturing all important information. Lack of compliance and the shortcomings of the devices often lead to the need for additional devices, follow-on monitoring, or other tests to make a correct diagnosis.

Current methods to correlate symptoms with the occurrence of arrhythmias, including the use of cardiac rhythm monitoring devices, such as Holter monitors and cardiac event recorders, are often not sufficient to allow an accurate diagnosis to be made. In fact, Holter monitors have been shown to not lead to a diagnosis up to 90% of the time ("Assessment of the Diagnostic Value of 24-Hour Ambulatory Electrocardiographic Monitoring", by DE Ward et al. Biotelemetry Patient Monitoring, vol. 7, published in 1980).

Additionally, the medical treatment process to actually obtain a cardiac rhythm monitoring device and initiate monitoring is typically very complicated. There are usually numerous steps involved in ordering, tracking, monitoring, retrieving, and analyzing the data from such a monitoring device. In most cases, cardiac monitoring devices used today are ordered by a cardiologist or a cardiac electrophysiologist (EP), rather than the patient's primary care physician (PCP). This is of significance since the PCP is often the first physician to see the patient and determine that the patient's symptoms could be due to an arrhythmia. After the patient sees the PCP, the PCP will make an appointment for the patient to see a cardiologist or an EP. This appointment is usually several weeks from the initial visit with the PCP, which in itself leads to a delay in making a potential diagnosis as well as increases the likelihood that an arrhythmia episode will occur and go undiagnosed. When the patient finally sees the cardiologist or EP, a cardiac rhythm monitoring device will usually be ordered. The monitoring period can last 24 to 48 hours (Holter monitor) or up to a month (cardiac event monitor or mobile telemetry device). Once the monitoring has been completed, the patient typically must return the device to the clinic, which itself can be an inconvenience. After the data has been processed by the monitoring company or by a technician on-site at a hospital or office, a report will finally be sent to the cardiologist or EP for analysis. This complex process results in fewer patients receiving cardiac rhythm monitoring than would ideally receive it.

To address some of these issues with cardiac monitoring, the assignee of the present application developed various embodiments of a small, long-term, wearable, physiological monitoring device. One embodiment of the device is the Zio® Patch. Various embodiments are also described, for example, in U.S. Pat. Nos. 8,150,502, 8,160,682 8,244,335, 8,560,046, and 8,538,503, the full disclosures of which are hereby incorporated herein by reference. Generally, the physiological patch-based monitors described in the above references fit comfortably on a patient's chest and are designed to be worn for at least one week and typically two to three weeks. The monitors detect and record cardiac rhythm signal data continuously while the device is worn, and this cardiac rhythm data is then available for processing and analysis.

Physiological Monitoring Devices

Figure 1B:
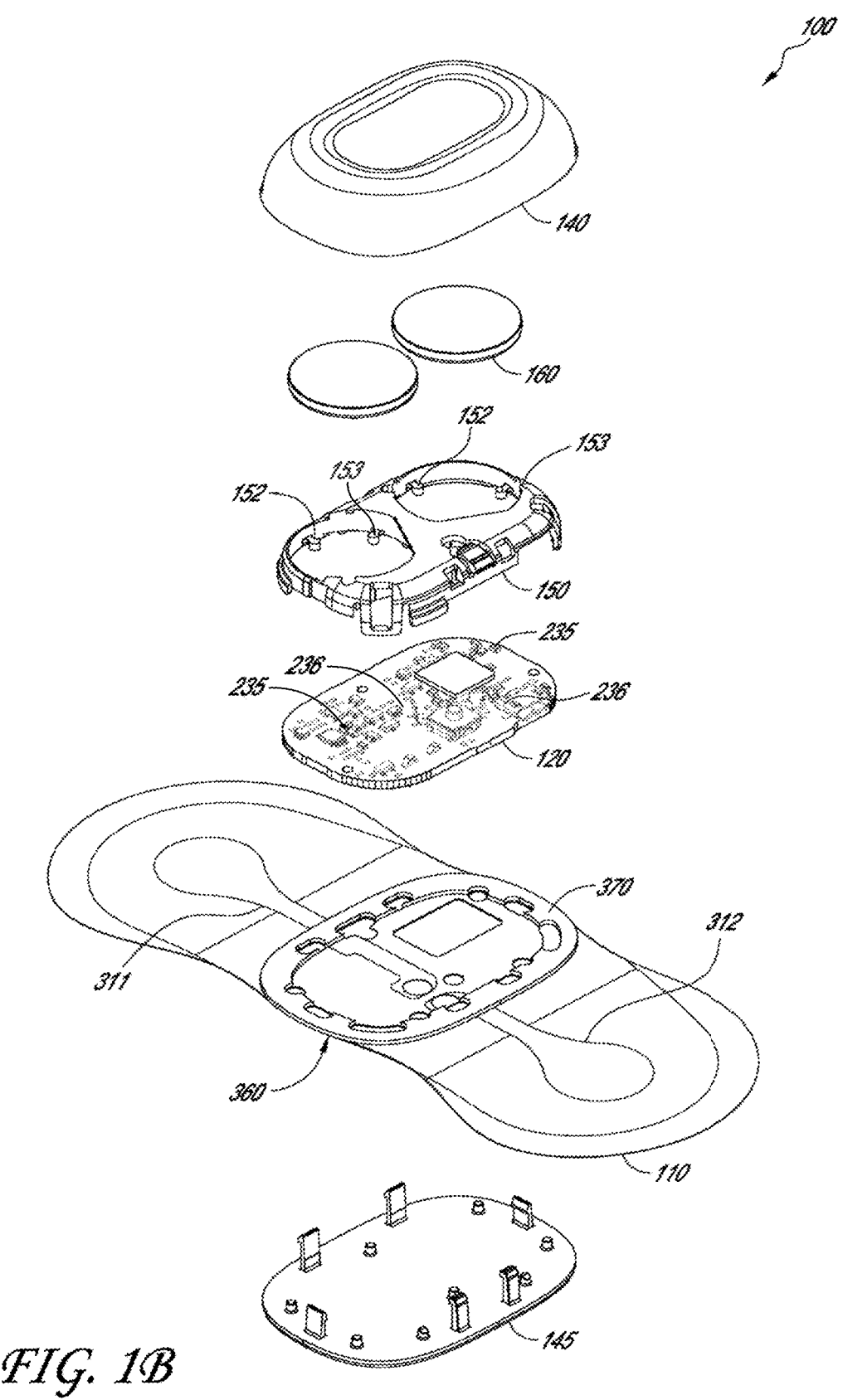

Referring to FIGS. 1A and 1B, perspective and exploded profile views of one embodiment of a physiological monitoring device 100 are provided. As seen in FIG. 1A, physiological monitoring device 100 may include a flexible body 110 coupled with a watertight, rigid housing 115, and a hinge portion 132. Flexible body 110 (which may be referred to as "flexible substrate" or "flexible construct") typically includes two wings 130, 131, which extend laterally from rigid housing 115, and two flexible electrode traces 311, 312, each of which is embedded in one of wings 130, 131. Each electrode trace 311, 312 is coupled, on the bottom surface of flexible body 110, with a flexible electrode (not visible in FIG. 1A). The electrodes are configured to sense heart rhythm signals from a patient to which monitoring device 100 is attached. Electrode traces 311, 312 then transmit those signals to electronics (not visible in FIG. 1A) housed in rigid housing 115. Rigid housing 115 also typically contains a power source, such as one or more batteries.

Referring now to FIG. 1B, a partially exploded view of physiological monitoring device 100 illustrates component parts that make up, and that are contained within, rigid housing 115 in greater detail. In this embodiment, rigid housing 115 includes an upper housing member 140, which detachably couples with a lower housing member 145. Sandwiched between upper housing member 140 and lower housing member 145 are an upper gasket 370, and a lower gasket 360 (not visible on FIG. 1B but just below upper gasket 370). Gaskets 370, 360 help make rigid housing member 115 watertight when assembled. A number of components of monitoring device 100 may be housed between upper housing member 140 and lower housing member 145. For example, in one embodiment, housing 115 may contain a portion of flexible body 110, a printed circuit board assembly (PCBA) 120, a battery holder 150, and two batteries 160. Printed circuit board assembly 120 is positioned within housing 115 to contact electrode traces 311, 312 and batteries 160. In various embodiments, one or more additional components may be contained within or attached to rigid housing 115. Some of these optional components are described further below, in reference to additional drawing figures.

Battery holder 150, according to various alternative embodiments, may hold two batteries (as in the illustrated embodiment), one battery, or more than two batteries. In other alternative embodiments, other power sources may be used. In the embodiment shown, battery holder 150 includes multiple retain tabs 153 for holding batteries 160 in holder 150. Additionally, battery holder 150 includes multiple feet 152 to establish correct spacing of batteries 160 from the surface of PCBA 120 and ensure proper contact with spring fingers 235 and 236. Spring fingers 235 and 236 are used in this embodiment rather than soldering batteries 160 to PCBA 120. Although soldering may be used in alternative embodiments, one advantage of spring fingers 235 and 236 is that they allow batteries 160 to be removed from PCBA 120 and holder 150 without damaging either of those components, thus allowing for multiple reuses of both Eliminating solder connections also simplifies and speeds up assembly and disassembly of monitoring device 100. In some embodiments, upper housing member 140 may act as a patient event trigger.

Figure 2A:
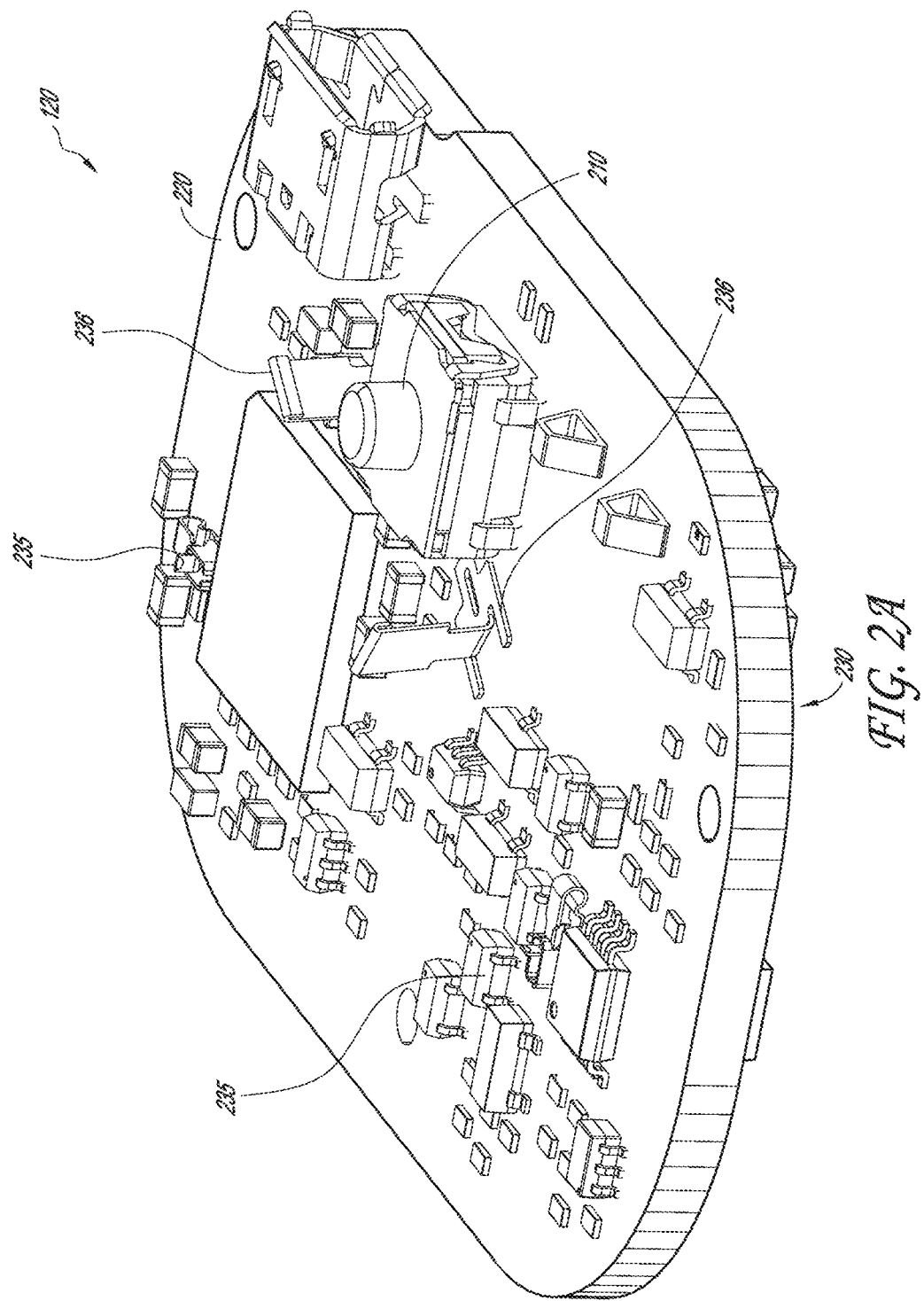
FIGS. 2A and 2B are top perspective and bottom perspective views, respectively, of a printed circuit board assembly of the physiological monitoring device, according to one embodiment.
Figure 2B:
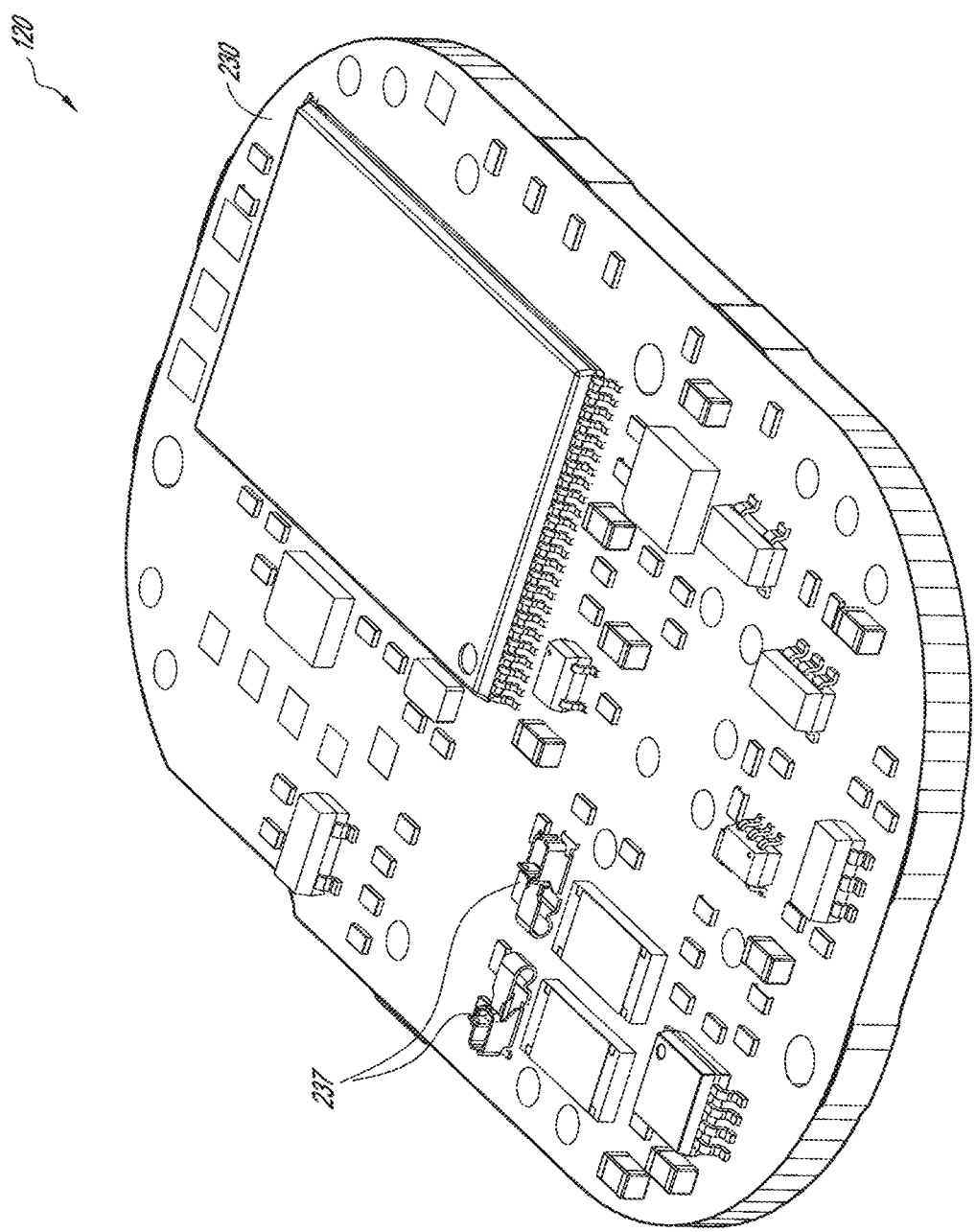

Referring now to the embodiments in FIGS. 2A and 2B, printed circuit board assembly 120 (or PCBA) may include a top surface 220, a bottom surface 230, a patient trigger input 210 and spring contacts 235, 236, and 237. Patient trigger input 210 may be configured to relay a signal from a patient trigger, such as upper housing member 140 described above, to PCBA 120. For example, patient trigger input 210 may be a PCB switch or button that is responsive to pressure from the patient trigger (for example, the upper surface of upper housing portion 140).

Figure 3A:
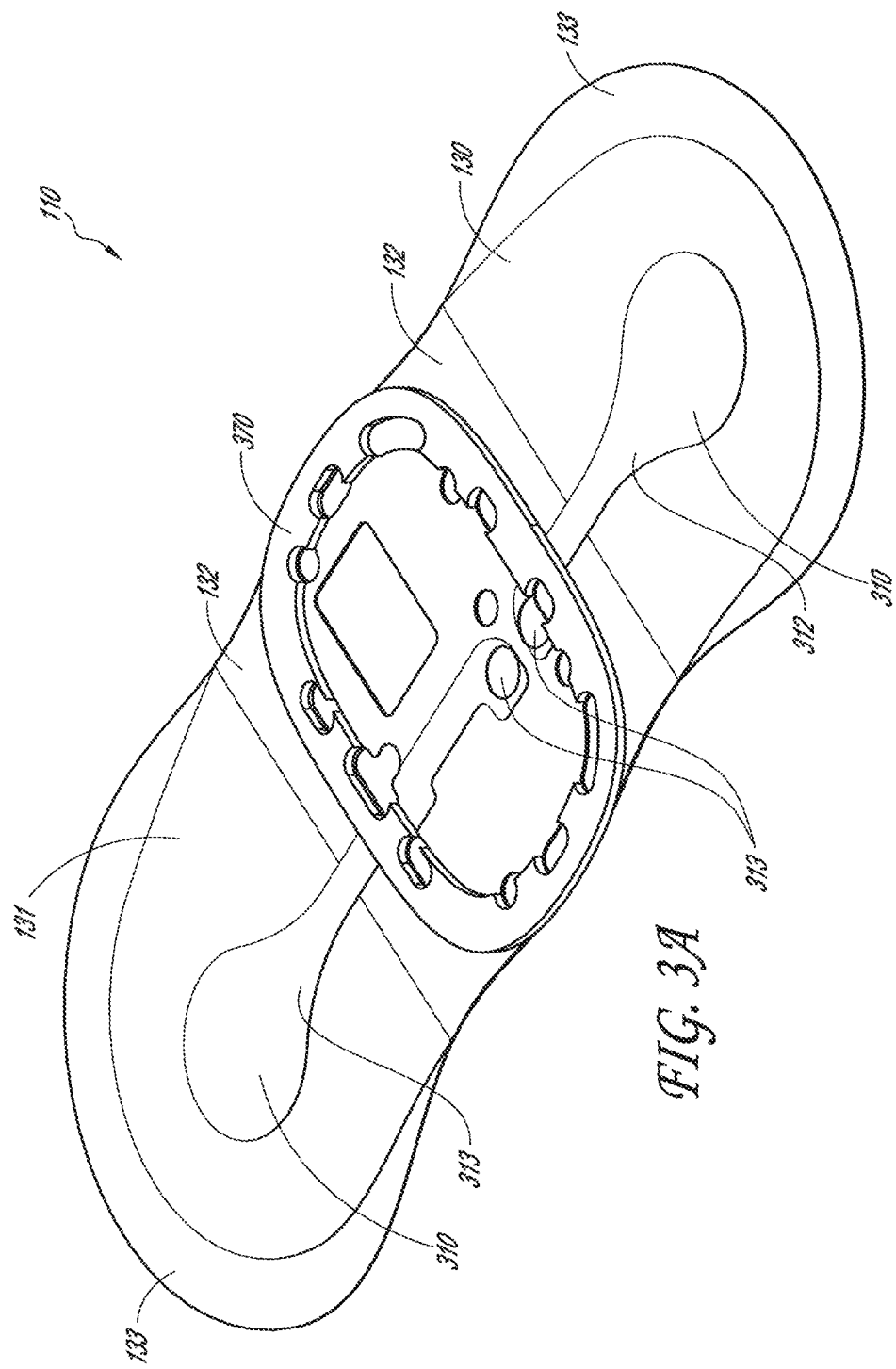
Figure 3B:
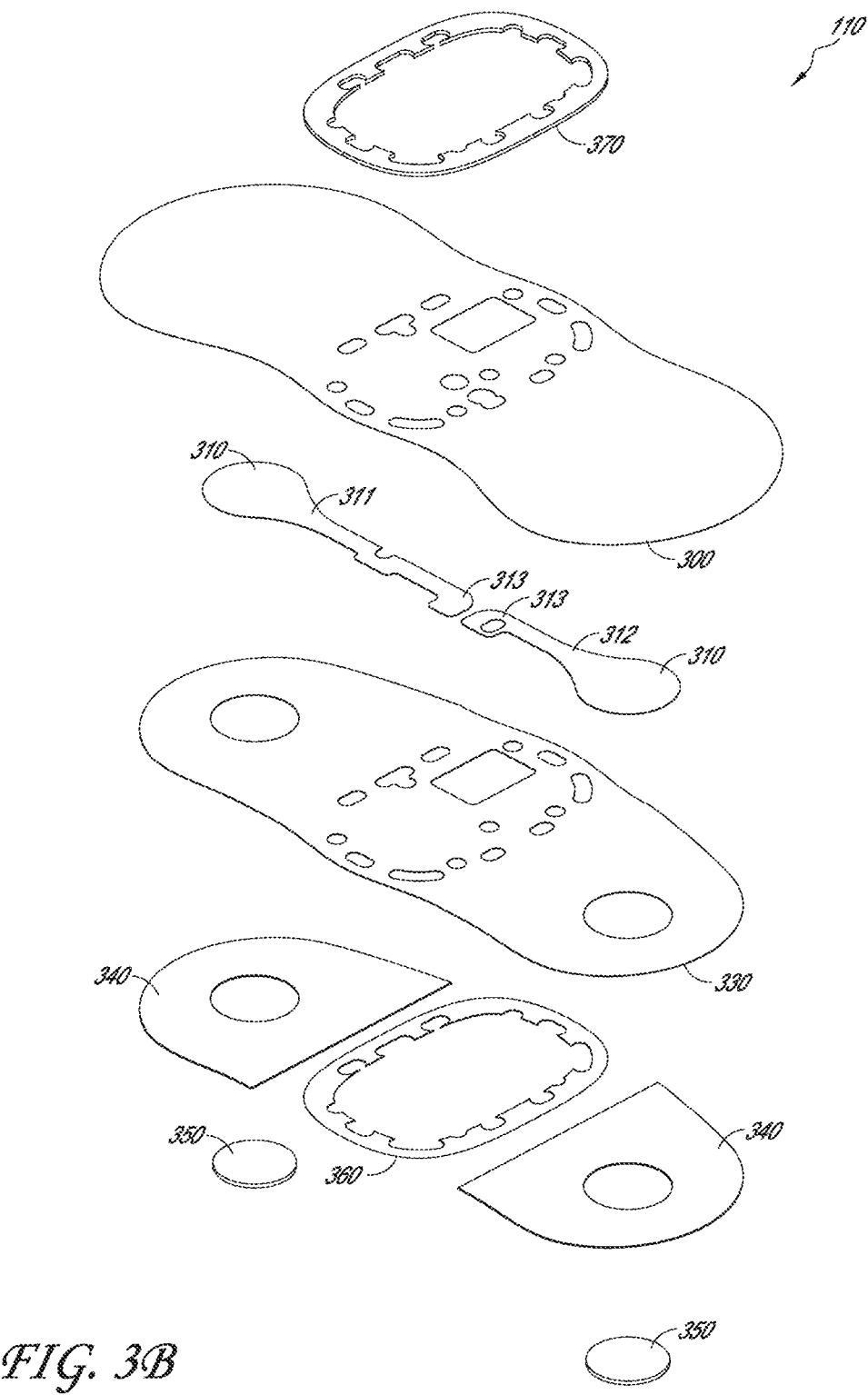

With reference now to the embodiments of FIGS. 3A and 3B, flexible body 110 is shown in greater detail. As illustrated in FIG. 3A, flexible body 110 may include wings 130, 131, a thin border 133 (or "rim" or "edge") around at least part of each wing 130, 131, electrode traces 311, 312, and a hinge portion 132 (or "shoulder") at or near a junction of each wing 130, 131 with rigid housing 115.

As illustrated in the embodiments of FIGS. 3C and 3D, ECG circuit interface portions 313 are in physical contact with spring fingers 237 and provide electrical communication with PCBA 120 when device 100 or zoomed-in device portion 101 is assembled. Electrode interface portions 310 contact hydrogel electrodes 350. Thus, electrode traces 311, 312 transmit cardiac rhythm signals (and/or other physiological data in various embodiments) from electrodes 350 to PCBA 120.

Figure 3E:
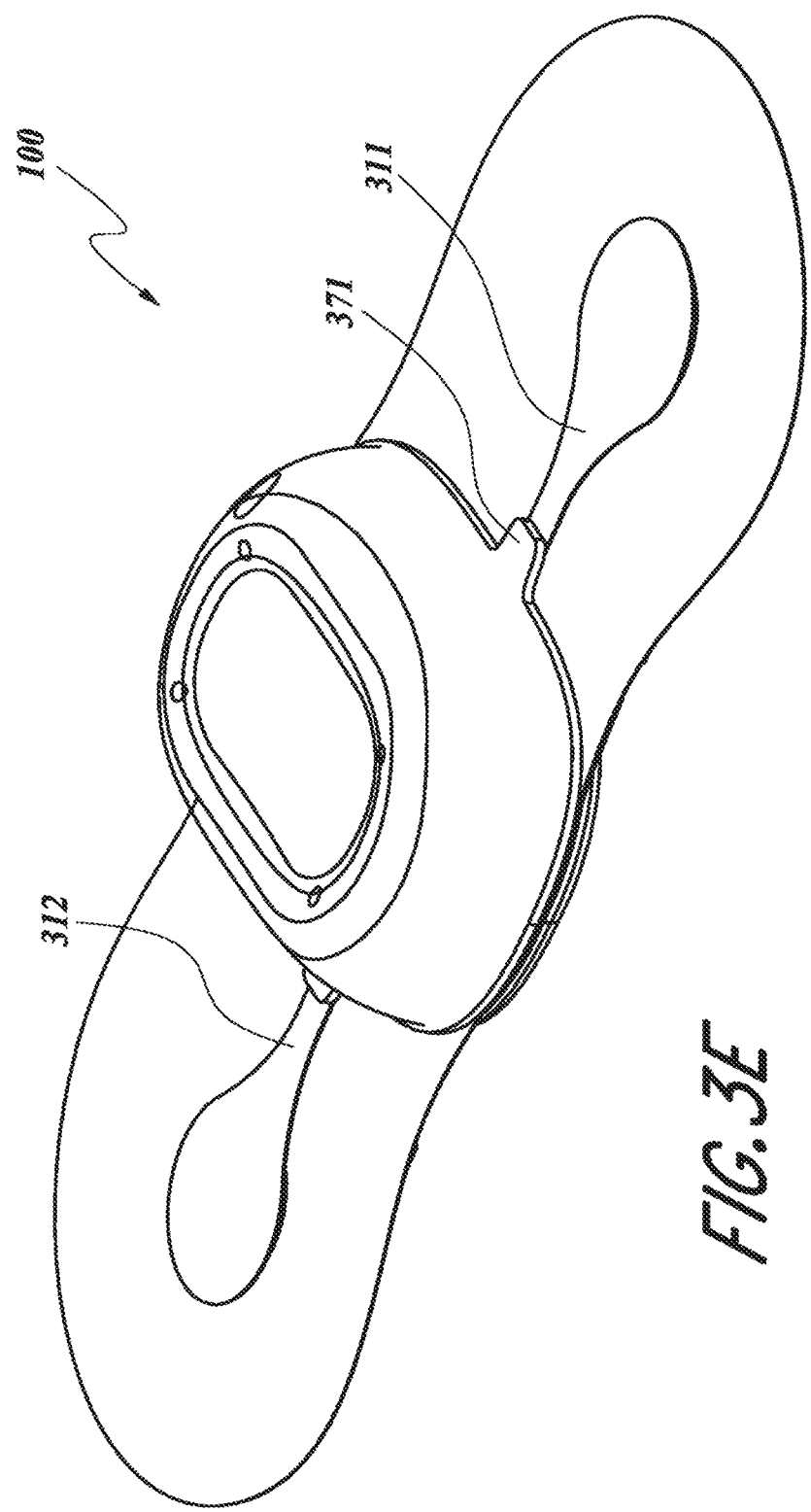

FIG. 3E depicts yet another embodiment where top gasket 370 includes tabs 371 that protrude away from the profile of top housing 140 while still being adhered to upper substrate 300. The tabs 371 cover a portion of electrode traces 311, 312 and provide a strain relief for the traces at the point of highest stress where the flexible body meets the rigid housing.

Figure 4:
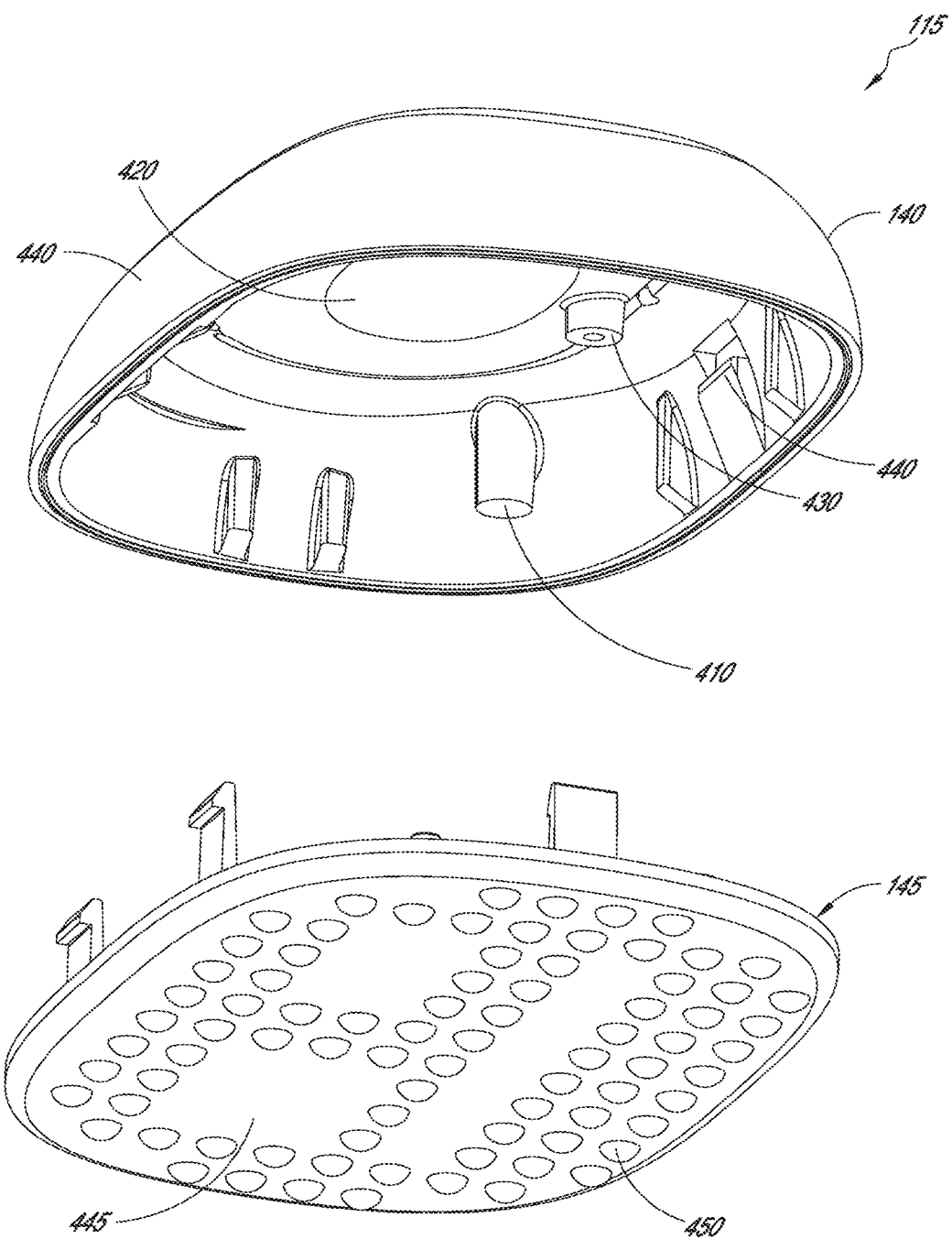
FIG. 4 is an exploded view of a rigid housing of the physiological monitoring device; according to one embodiment.

With reference now to the embodiment of FIG. 4, upper housing member 140 and lower housing member 145 of rigid housing 115 are shown in greater detail. Upper and lower housing members 140, 145 may be configured, when coupled together with gaskets 360, 370 in between, to form a watertight enclosure for containing PCBA 120, battery holder 150, batteries 160 and any other components contained within rigid housing 115. Housing members 140, 145 may be made of any suitable material to protect internal components, such as water resistant plastic.

Figure 5B:
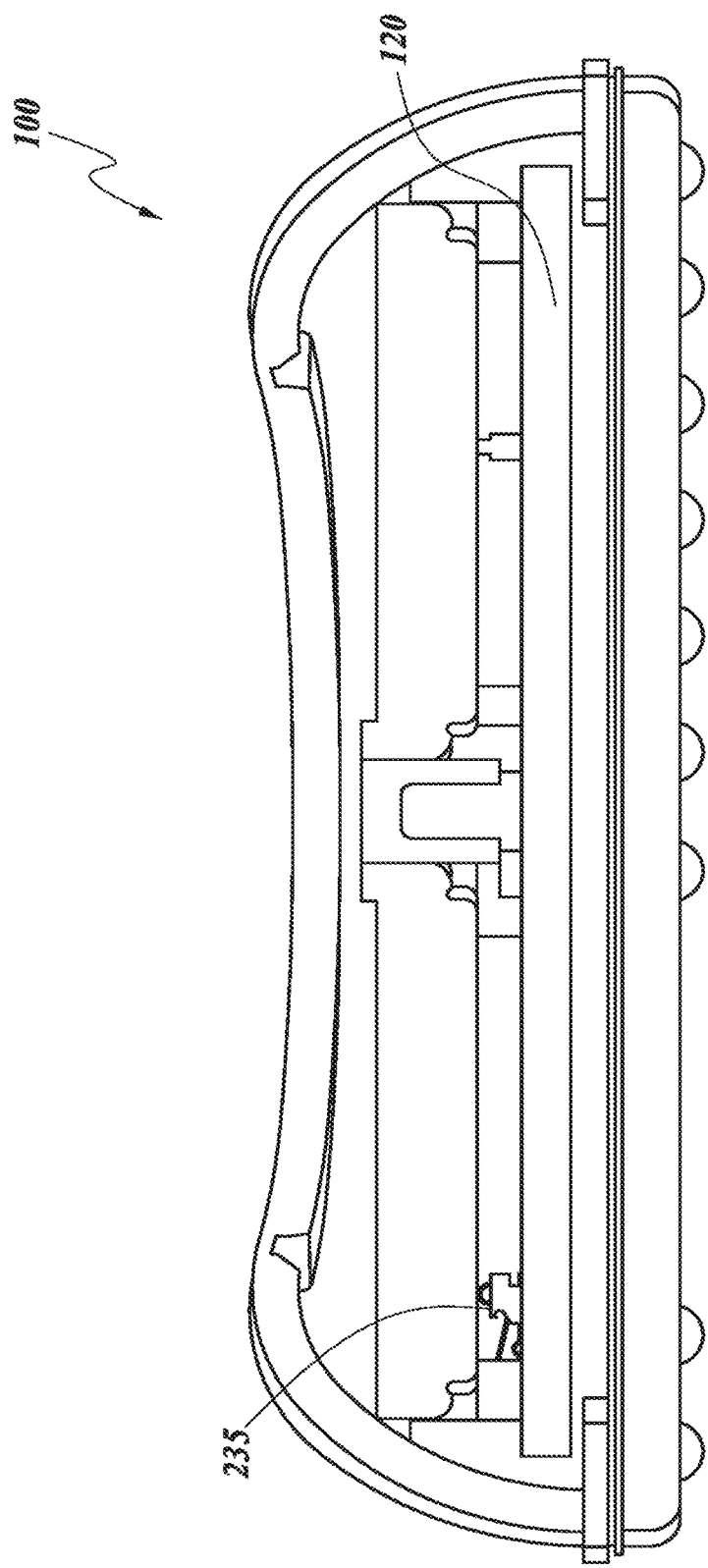

Referring now to the embodiment of FIG. 5A, battery holder 150 is shown in greater detail. Battery holder 150 may be made of plastic or other suitable material, is configured to be mounted to PCBA 120 and subsequently attached to rigid housing 115, and is capable of holding two batteries 160 (FIG. 1B). A plurality of protrusions 152 provide a stable platform for batteries 160 to be positioned a fixed distance above the surface of PCBA 120, avoiding unwanted contact with sensitive electronic components yet providing for adequate compression of spring contacts 235 (FIG. 5B).

Figure 6B:
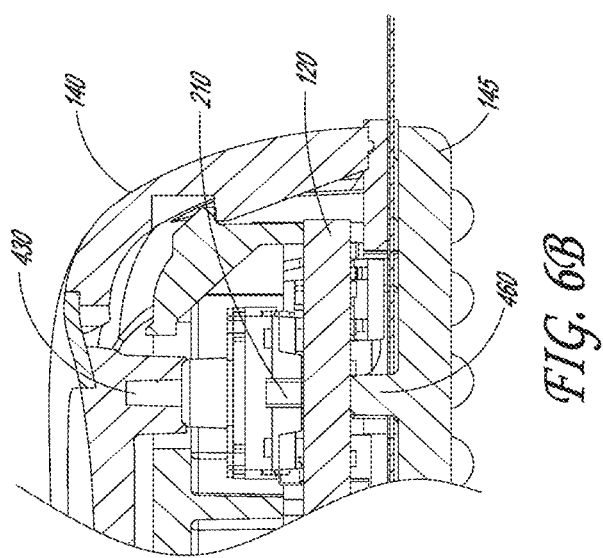

With reference now to the embodiments of FIGS. 6A and 6B, physiological monitoring device 100 is shown in side view cross-section. As shown in 6A, physiological monitoring device 100 may include flexible body 110 coupled with rigid housing 115. Flexible body 110 may include top substrate layer 300, bottom substrate layer 330, adhesive layer 340 and electrodes 350. Electrode traces 311, 312 are also typically part of flexible body 110 and are embedded between top substrate layer 300 and bottom substrate layer 330, but they are not shown in FIG. 6. Flexible body 110 forms two wings 130, 131, extending to either side of housing 115, and a border 133 surrounding at least part of each wing 130, 131. Rigid housing 115 may include an upper housing member 140 coupled with a lower housing member 145 such that it sandwiches a portion of flexible body 110 in between and provides a watertight, sealed compartment for PCBA 120. Upper housing member 140 may include inner trigger member 430, and PCBA may include patient trigger member 210. As discussed previously, lower housing member 145 may include multiple dimples 450 or divots to enhance the comfort of the monitoring device 100. In certain embodiments, an additional mechanism to reduce and prevent unwanted bending of PCBA 120 may be used. This mechanism is shown in FIG. 6B.

Figure 7:
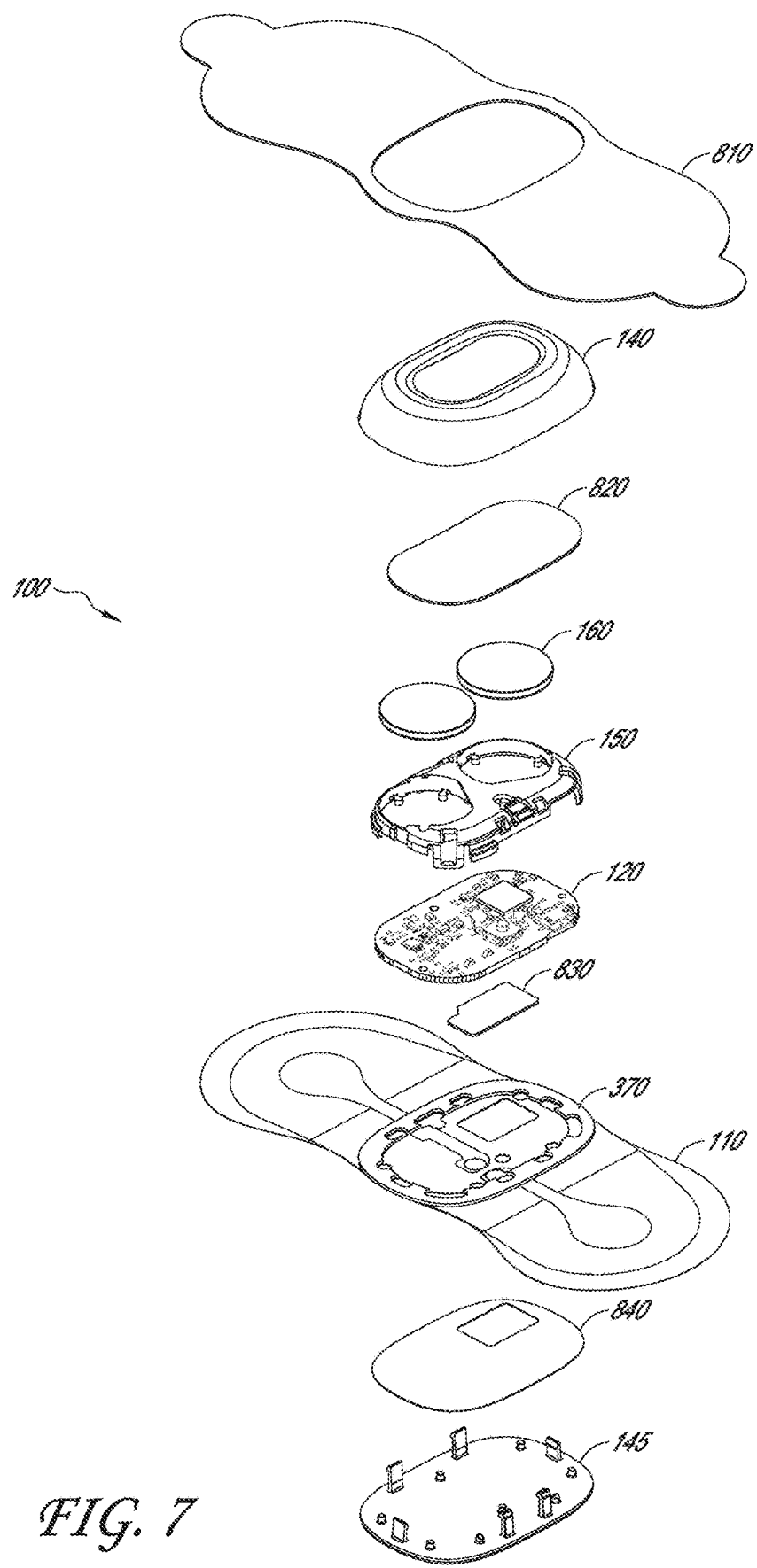
FIG. 7 is an exploded view of the physiological monitoring device including a number of optional items, according to one embodiment.

Referring to FIG. 7, in some embodiments, physiological monitoring device 100 may include one or more additional, optional features. For example, in one embodiment, monitoring device 100 may include a removable liner 810, a top label 820, a device identifier 830 and a bottom label 840.

Figure 8A:
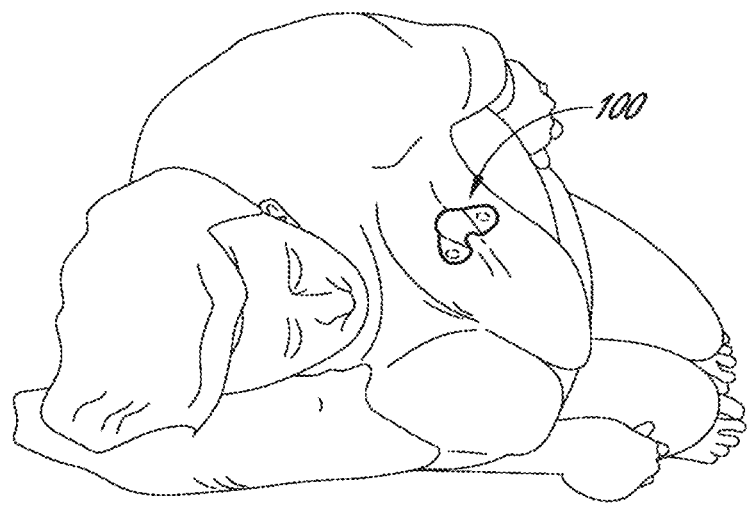
FIGS. 8A and 8B are perspective views of two people wearing the physiological monitoring device, illustrating how the device bends to conform to body movement and position, according to one embodiment.
Figure 8B:
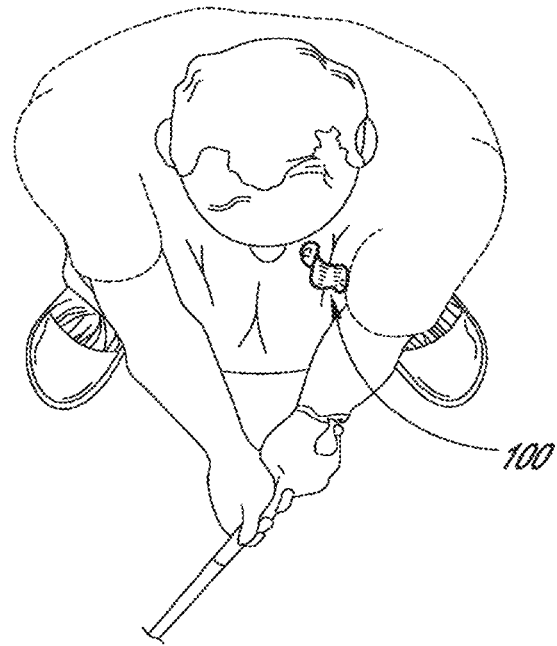

Referring now to the embodiments of FIGS. 8A and 8B, physiological monitoring device 100 generally includes hinge portions 132 at or near the juncture of each wing 130, 131 with rigid housing 115. Additionally, each wing 130, 131 is typically adhered to the patient via adhesive layers 340, while rigid body 115 is not adhered to the patient and is thus free to "float" (for example, move up and down) over the patient's skin during movement and change of patient position. In other words, when the patient's chest contracts, rigid housing pops up or floats over the skin, thus minimizing stress on device 100, enhancing comfort, and reducing the tendency of wings 130, 131 to peel off of the skin.

Figure 9A:
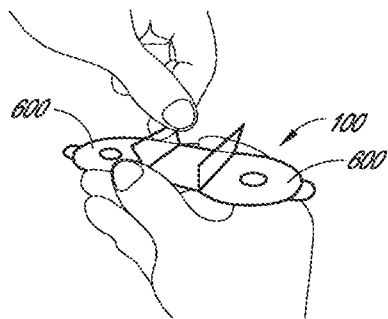
FIGS. 9A, 9B, 9C, 9D, 9E, and 9F illustrate various steps for applying the physiological monitor to a patient's body, according to one embodiment.
Figure 9D:
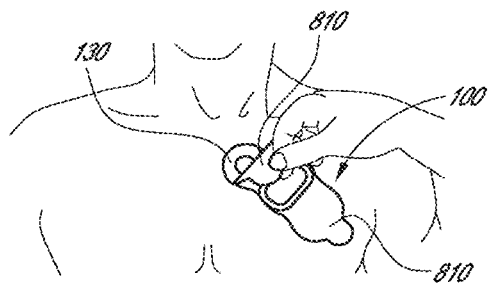
Figure 9B:
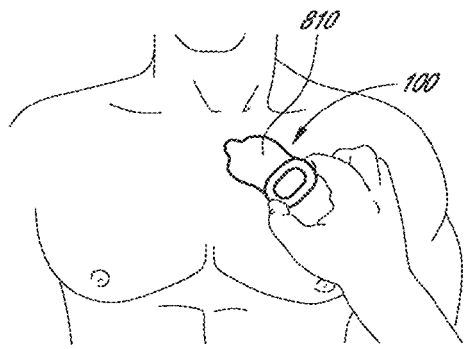
Figure 9E:
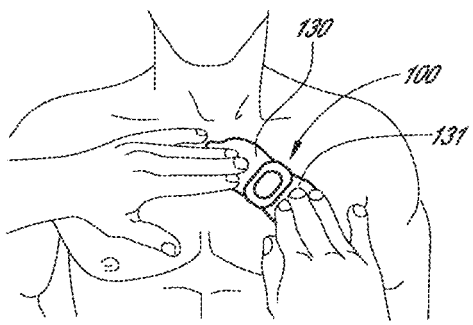
Figure 9C:
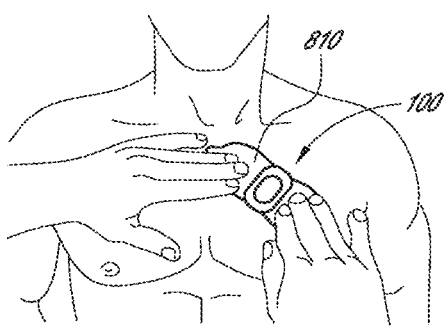

Referring now to FIGS. 9A-9F, one embodiment of a method for applying physiological monitoring device 100 to the skin of a human subject is described. In this embodiment, before the first step shown in FIG. 9A, the patient's skin may be prepared, typically by shaving a small portion of the skin on the left chest where device 100 will be placed and then abrading and/or cleaning the shaved portion. As shown in FIG. 9A, once the patient's skin is prepared, a first step of applying device 100 may include removing one or both of two adhesive covers 600 from adhesive layers 340 on the bottom surface of device 100, thus exposing adhesive layers 340. As illustrated in FIG. 9B, the next step may be to apply device 100 to the skin, such that adhesive layer 340 adheres to the skin in a desired location. Referring to FIG. 9C, after device 100 has been applied to the skin, pressure may be applied to flexible body 110 to press it down onto the chest to help ensure adherence of device 100 to the skin.

Figure 9F:
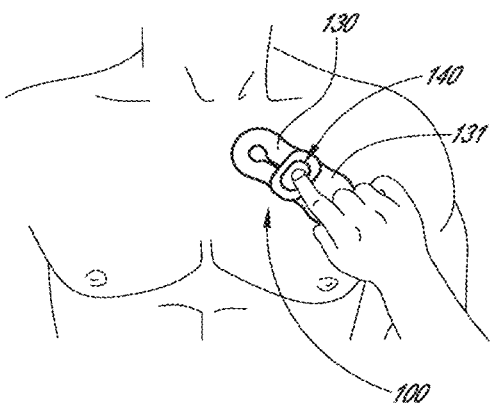

In a next step, referring to FIG. 9D, liner 810 is removed from (for example, peeled off of) the top surface of flexible body 110. As shown in FIG. 9E, once liner 810 is removed, pressure may again be applied to flexible body 110 to help ensure it is adhered to the skin. Finally, as shown in FIG. 9F, upper housing member 140 may be pressed to turn on physiological monitoring device 140. This described method is only one embodiment. In alternative embodiments, one or more steps may be skipped and/or one or more additional steps may be added.

The physiological monitors described above and elsewhere in the specification may further be combined with methods and systems of data processing and transmission that improve the collection of data from the monitor. Further, the methods and systems described below may improve the performance of the monitors by enabling timely transmission of clinical information while maintaining the high patient compliance and ease-of-use of the monitor described above. For example, the methods and systems of data processing and transmission described herein this section of elsewhere in the specification may serve to extend the battery life of the monitor, improve the accuracy of the monitor, and/or provide other improvements and advantages as described herein this section or elsewhere in the specification.

Device Monitoring and Clinical Analysis Platform

The systems and methods described in detail below, in reference to the embodiments of FIGS. 10 to 17, may selectively extract, transmit, and analyze electrocardiographic signal data and other physiological data from a wearable physiological monitor, such as is described above in relation to FIGS. 1 through 9. The systems and methods described below can improve the performance of a wearable physiological monitor that simultaneously records and transmits data through multiple means. For example, selective transmission of extracted data allows for decreased power consumption because the wearable patch is not required to transmit all recorded data. By sending extracted data, much of the analysis may be performed away from the wearable device without requiring full on-board rhythm analysis, which can also be highly power consumptive, reducing battery life. Further, remote analysis without the power constraints inherent to a wearable device may allow for greater sensitivity and accuracy in analysis of the data. Decreased power consumption serves to improve patient compliance because it prolongs the time period between or even eliminates the need for device replacement, battery changes or battery recharging during the monitoring cycle. By decreasing battery consumption, longer monitoring times may be enabled without device replacement, for example, at least one week, at least two weeks, at least three weeks, or more than three weeks.

Figure 10:
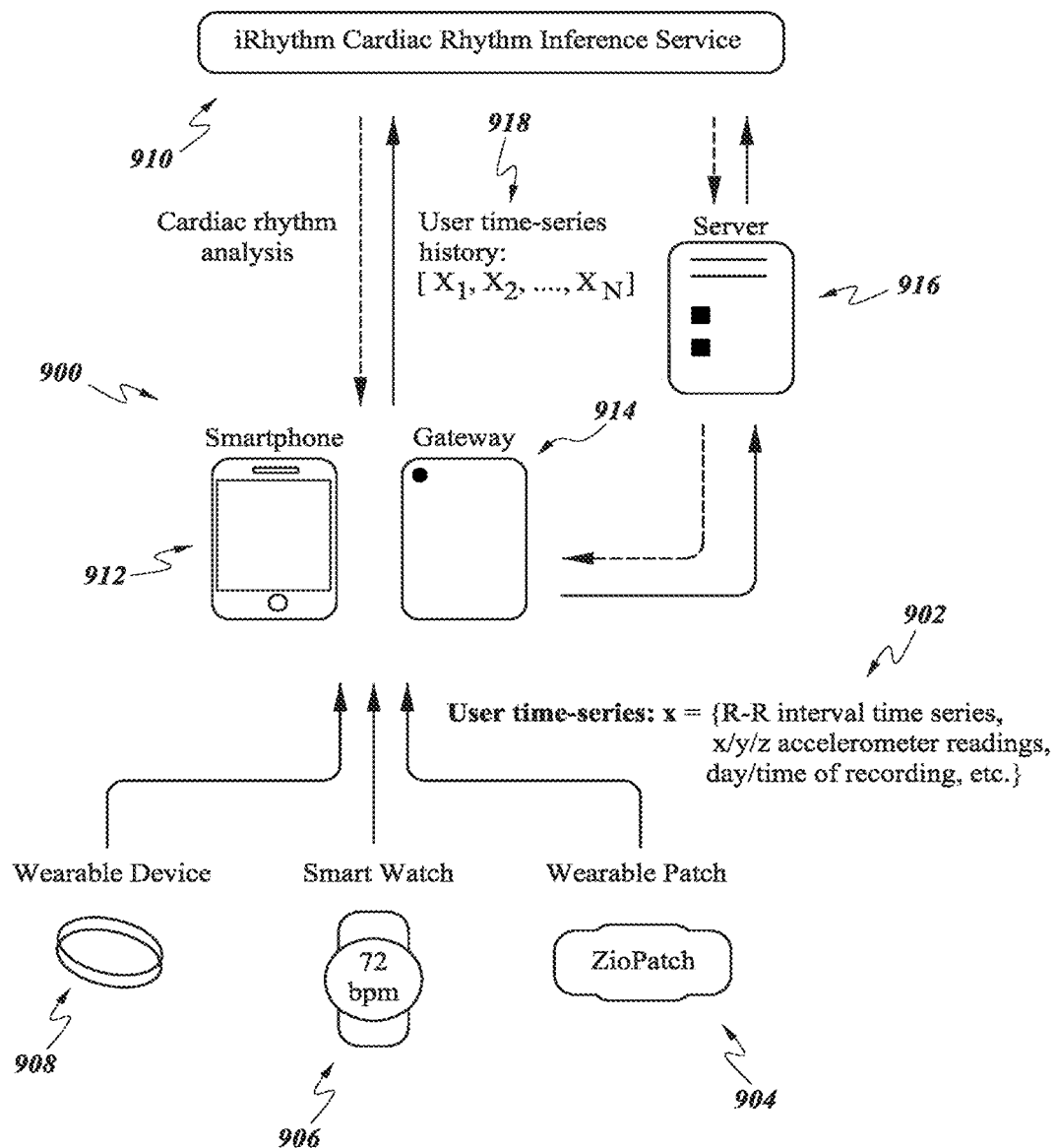
FIG. 10 illustrates a schematic diagram of an embodiment of a cardiac rhythm inference service.

FIG. 10 depicts a general overview of an embodiment of a system 900 for inferring cardiac rhythm information from an R-R interval time series 902, as may be generated by a continuous heart rate monitoring device 904. The R-R interval time series 902 inputted to the system may include a series of measurements of the timing interval between successive heartbeats. The R-R interval time series 902 data may be extracted from or received from a dedicated heart rate monitor such as a heart rate chest strap or heart rate watch, or a wearable health or fitness device 906, 908 that incorporates heart rate sensing functionality. Alternatively, the R-R interval time series 902 may be derived from a wearable patch designed to measure an ECG signal 904 (for instance, by locating the R peaks in the ECG using a QRS detection algorithm). Furthermore, the R-R interval time series 902 may be estimated from an alternative physiological signal such as that obtained from photoplethysmography (PPG). In this scenario, the peak-to-peak interval time series determined from the PPG signal may be used as an accurate estimate of the R-R interval time series.

In certain embodiments, a cardiac rhythm inference system may accept a plurality of R-R interval time series measured from devices of a given user 918, in addition to an individual R-R interval time series 902. In particular embodiments, a cardiac rhythm inference system 910 may accept additional sources of data, generally described as alternate sensor channels, in addition to R-R interval time series data, to enhance the accuracy and/or value of the inferred results.

Current wearable sensors, such as the iRhythm Zio-Patch™ 904, and further described above in relation to FIGS. 1-9, are capable of recording a single-lead electrocardiogram (ECG) signal for up to two weeks on a single battery charge.

Extraction, Transmission, and Processing Systems

Figure 11:
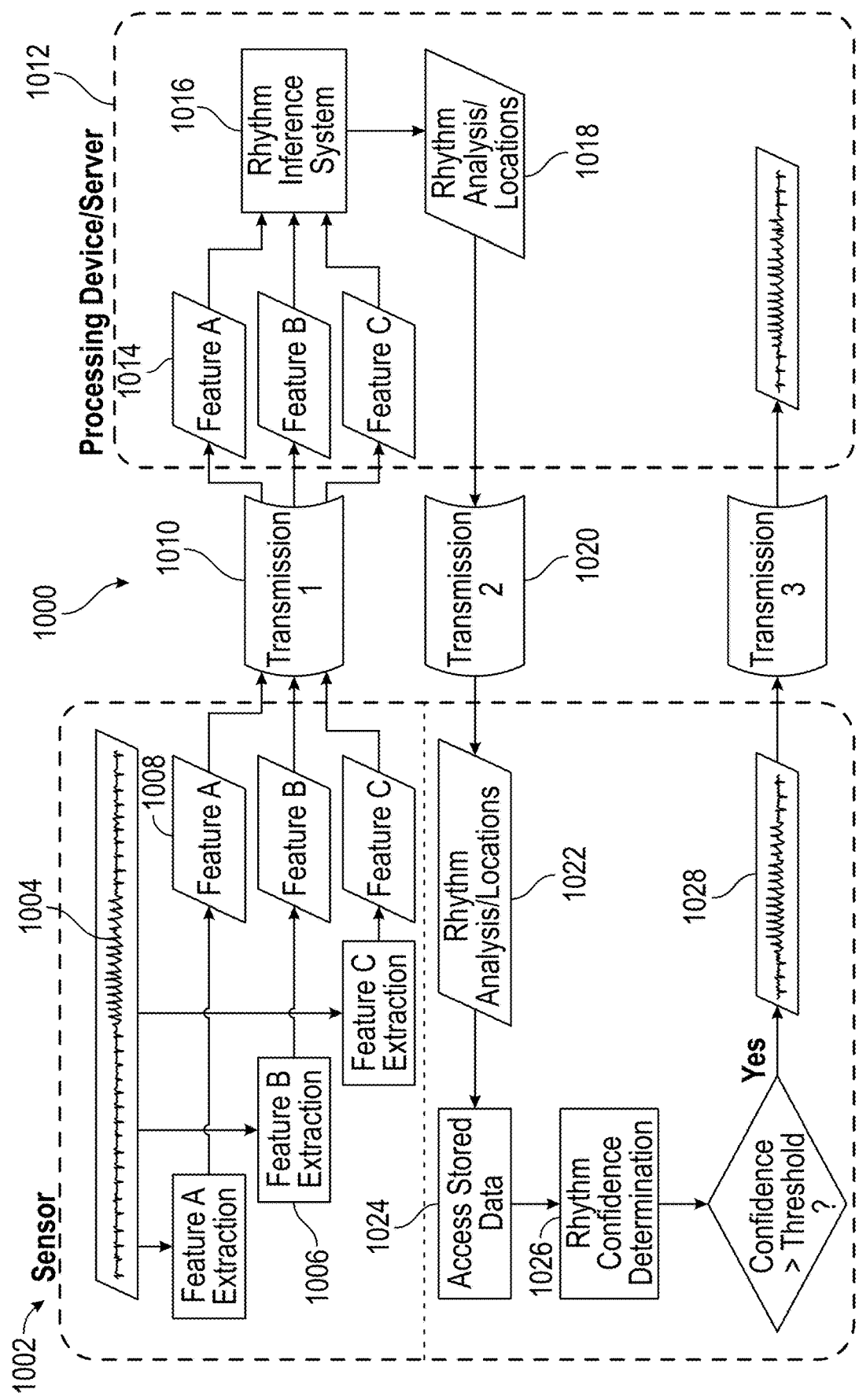
FIG. 11 is a schematic diagram of an embodiment of a system for extracting and transmitting data features from a physiological monitor.

FIG. 11 is a schematic illustration of an embodiment of a system and method 1000 for a wearable medical sensor 1002 with transmission capabilities, similar to the system and/or method described above in relation to FIG. 10. In some embodiments, sensor 1002, which may be any type of sensor or monitor described herein this section or elsewhere in the specification, continuously senses an ECG or comparable biological signal 1004 and continuously records an ECG or comparable biological signal 1004. The collected signal 1004 may then be continuously extracted into one or more features 1006, representing example features A, B, and C. The features of the ECG or comparable biological signal are extracted to facilitate analysis of the signal 1004 remotely.

Once the feature extraction as described above is completed, various features 1008 may then be transmitted 1010 to a processing device/server 1012. The features 1008 (and alternate sensor channel data and/or features as described below) are transmitted 1010 at regular intervals to a processor 1012 that is not a physical part of the sensor 1002.

In some embodiments, the transmitted features 1014 are processed by the remote processor utilizing the data features 1014 to perform analysis via a rhythm inference system 1016 that analyzes and identifies segments/locations 1018 likely to include arrhythmia. For example, arrhythmia and ectopy types that may be identified could include: Pause, $2^{nd}$ or $3^{rd}$ degree AVB, Complete Heart Block, SVT, AF, VT, VF, Bigeminy, Trigeminy, and/or Ectopy. Confidence of determination may be included in the identification of rhythms.

The identified arrhythmia locations 1018 are then transmitted 1020 back to the sensor 1002. The transmission 1020 back to the sensor may be accomplished by any communication protocols/technology described herein this section or elsewhere in the specification, for example via Bluetooth. The sensor then reads the transmitted identified locations 1022 and accesses 1024 the areas of memory corresponding to the transmitted identified locations 1022 of the ECG. In some embodiments, the sensor applies additional analysis of the identified segments to further build confidence in the arrhythmia identification. This further rhythm confidence determination step 1026 allows for increasing positive predictivity prior to the power-hungry transmission step. In embodiments, if the confidence exceeds a defined threshold the data segment is transmitted. If the confidence exceeds a threshold as described above, the sensor 1002 may transmit the requested ECG segments 1028 to the processing device via any transmission means described herein this section or elsewhere in the specification.

Figure 12:
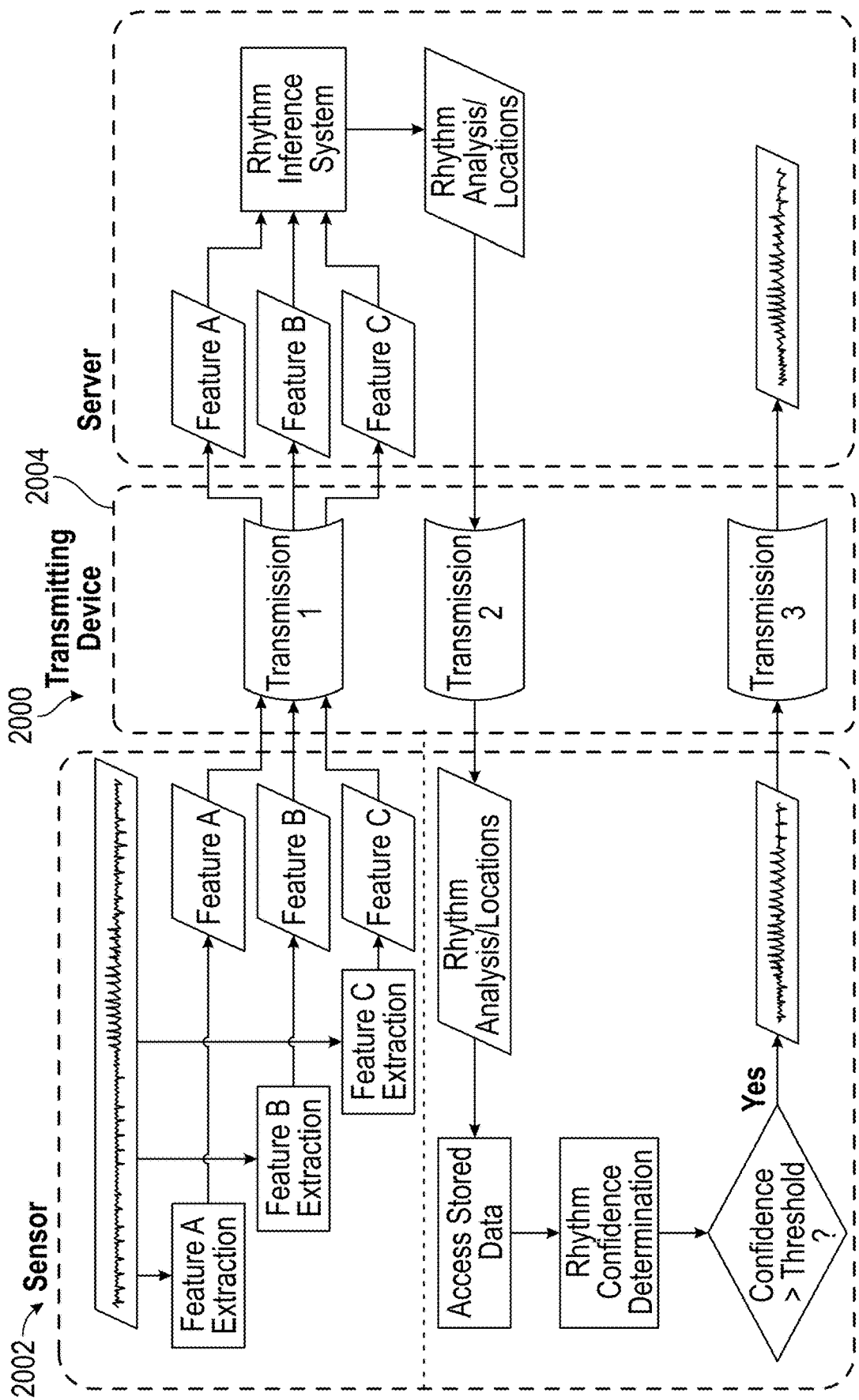
FIG. 12 is a schematic diagram of an embodiment of a system for extracting and transmitting data features from a physiological monitor using a transmitting device.

FIG. 12 is a schematic illustration of an embodiment of a system and method 2000 for a wearable ECG and/or medical sensor 2002 with transmission capabilities very similar to the system and/or method 1000 described above in relation to FIG. 11. The system of FIG. 12 differs from the system of FIG. 11 in that it includes secondary transmitting devices 2004.

Figure 13:
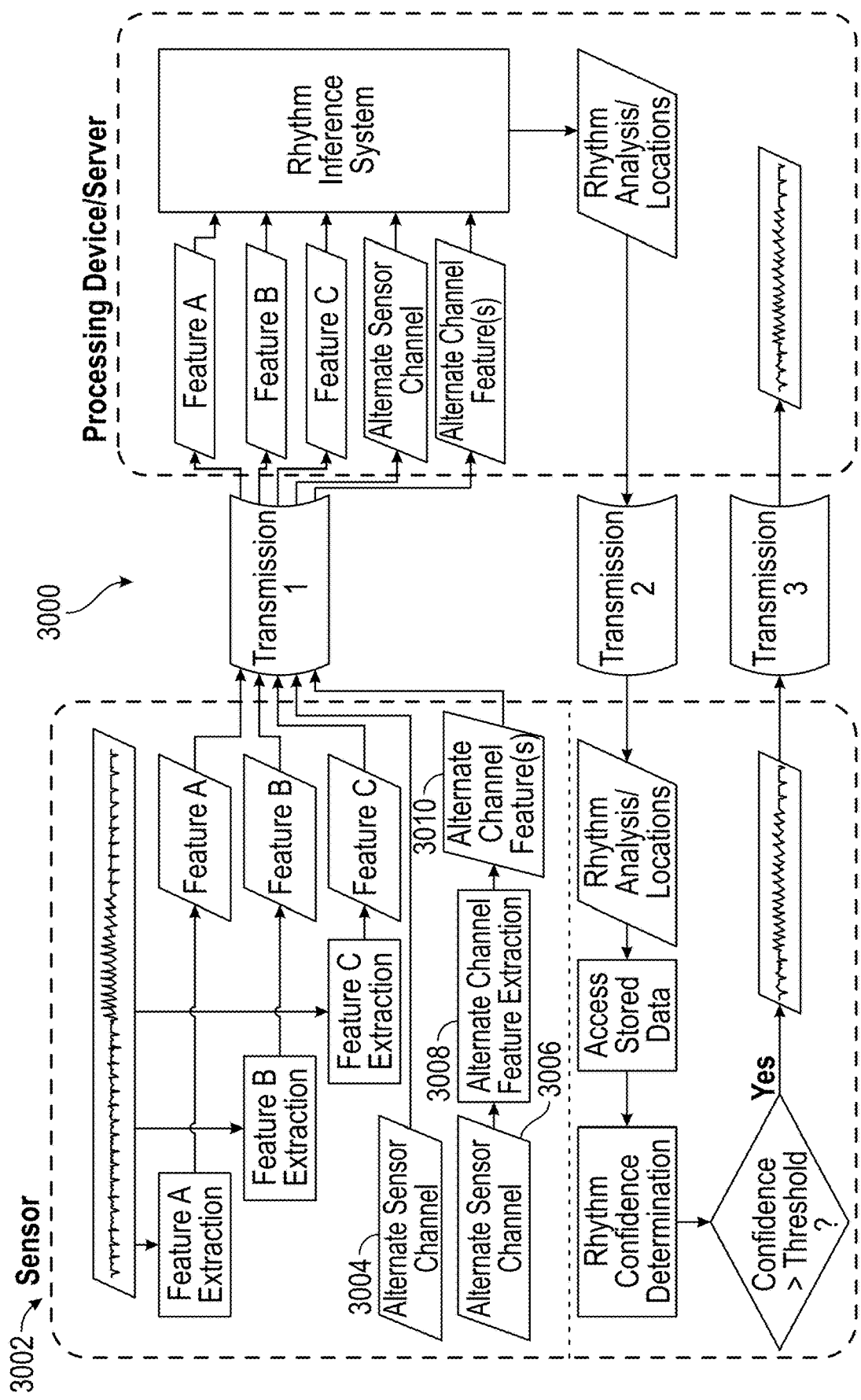
FIG. 13 is a schematic diagram of an embodiment of a physiological monitoring system utilizing additional data channels.

FIG. 13 is a schematic illustration of an embodiment of a system and method 3000 for a wearable ECG and/or medical sensor 3002 with transmission capabilities, very similar to the system and/or methods described above in relation to FIGS. 11 and 12. FIG. 13 differs from FIGS. 11 and 12 in that FIG. 13 illustrates alternate sensor channels 3004, 3006 producing alternate outputs and/or extraction 3008 of features 3010. Collection of other channels of data may serve to further augment ECG-extracted features. Data from the alternate sensor channels may be sent whole or specific features 3010 of the data channel may be extracted 3008.

Figure 14:
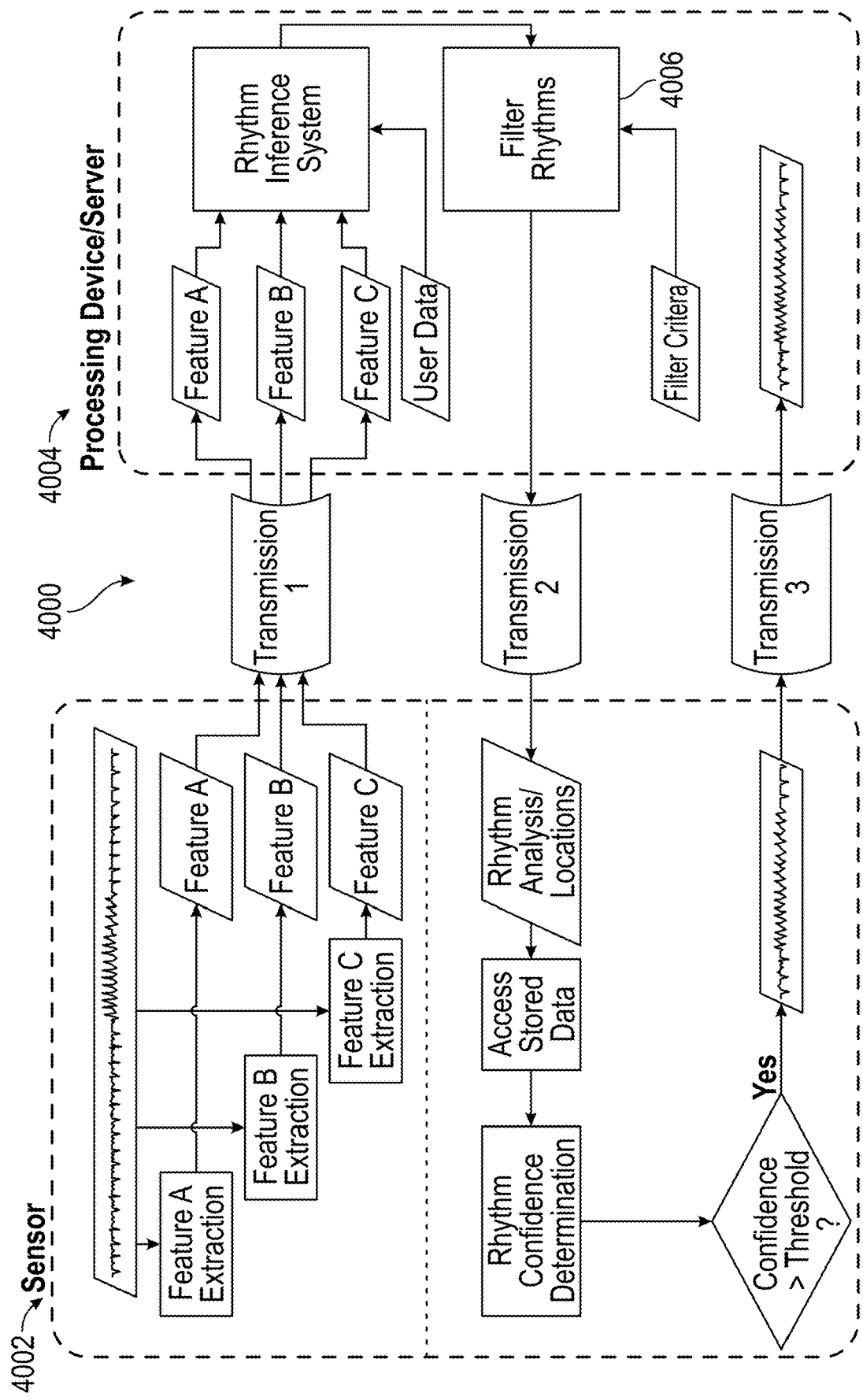
FIG. 14 is a schematic diagram of an embodiment of a physiological monitoring system incorporating data filters.

FIG. 14 is a schematic illustration of an embodiment of a system and method 4000 for a wearable ECG and/or medical sensor 4002 with transmission capabilities, very similar to the system and/or methods described above in relation to FIGS. 11 to 13. FIG. 14 differs from FIGS. 11 to 13 because the embodiment of FIG. 14 incorporates additional data filters. In some embodiments, the Processing Device 4004 may also filter rhythms 4006 identified by the rhythm inference system 4008 by applying filter criteria that may derive from multiple sources.

Figure 15:
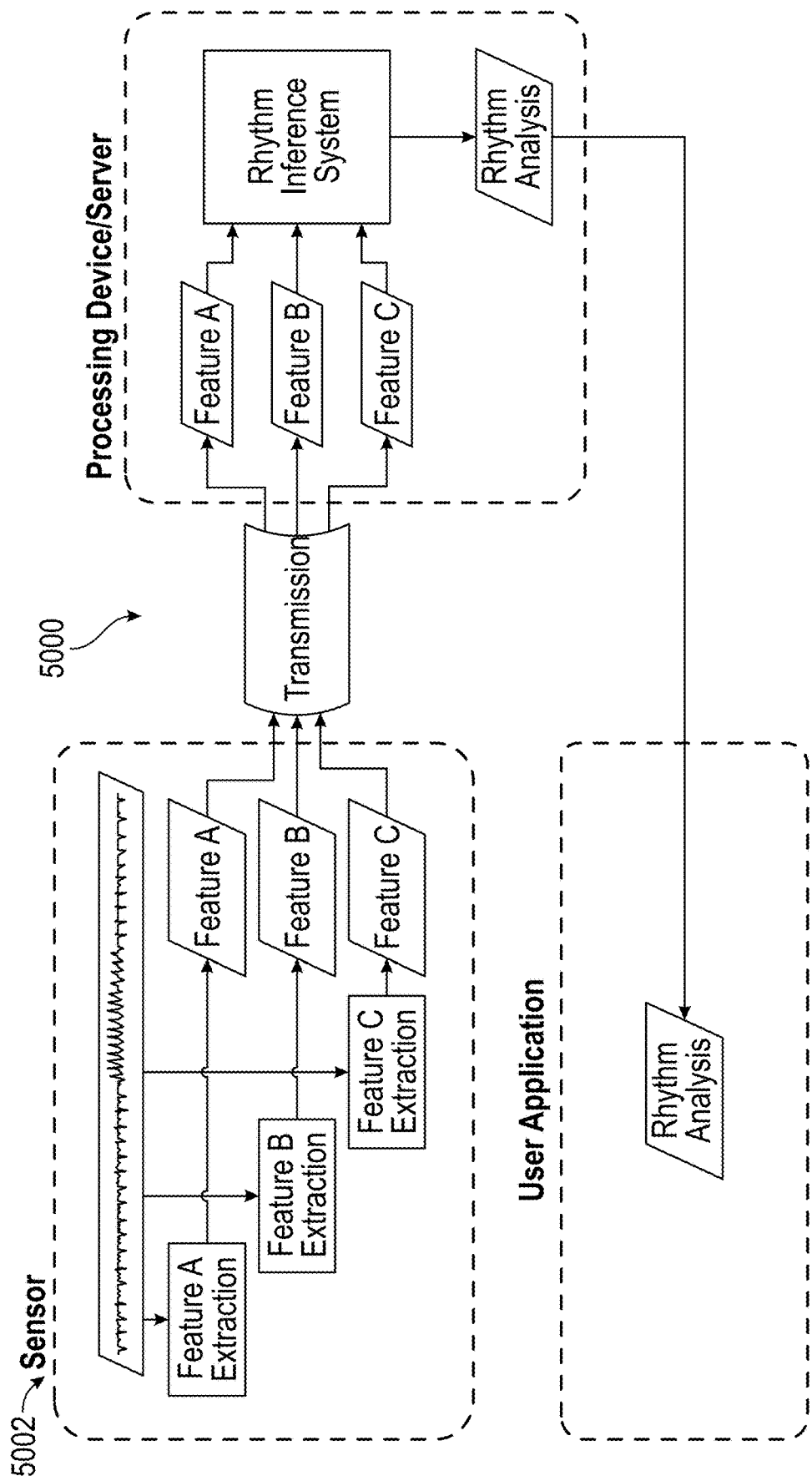
FIG. 15 is a schematic diagram of an embodiment of a wearable device system.

FIG. 15 is a schematic illustration of an embodiment of a system 5000 for a consumer wearable device without full ECG detection, with some similarities to the medical sensors of FIGS. 10 to 14. The sensors 5002 need not be medical-grade ECG sensors, but merely allow detection of beats. In embodiments, the sensor 5002 may continuously sense a data channel from which heart beat locations can be derived. Possible data sources include: PPG (optionally with multiple channels to increase accuracy), bio-impedance, and ECG without full implementation due to insufficient signal quality as compared to the sensors of FIGS. 10 to 14. Similar to the devices of FIGS. 10 to 14, features may be extracted from this signal, for example: R-peak locations, R-peak overflow flag, saturation flag, breathing rate, P/T wave locations, R-peak amplitude (or proxy), or ECG signal amplitude proxy.

The consumer device system 5000 without full ECG sensing advantageously enables arrhythmia analysis using consumer-available heart-rate sensors, thereby reducing the cost and increasing the availability of the device. Consequently, this may enable arrhythmia screening on a larger population, including via over-the-counter screening.

Figure 16:
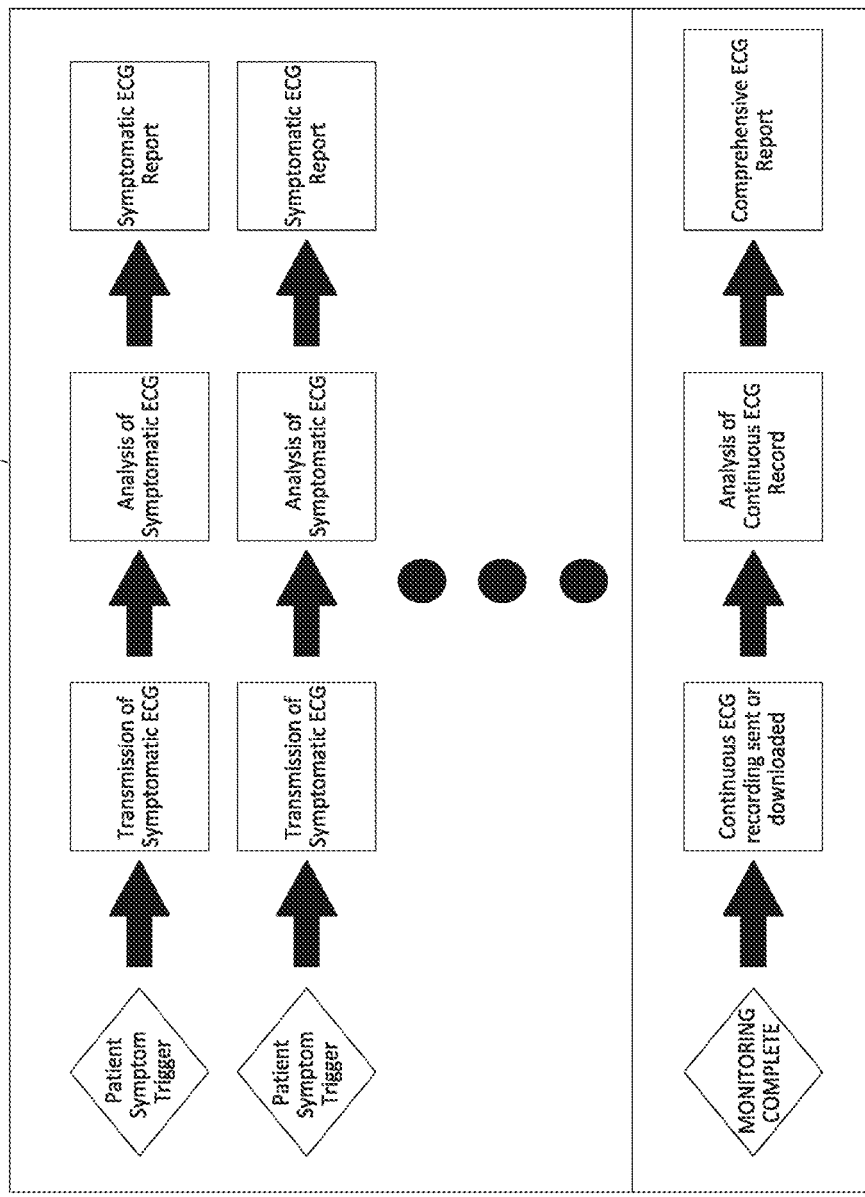
FIG. 16 is a schematic diagram of an embodiment of a symptomatic transmission system.

FIG. 16 is a schematic diagram of an embodiment of an ECG monitor system 6000 with symptomatic transmission. Such a system would involve a wearable ECG sensor, similar to the sensors described in relation to FIGS. 1 to 14. As described above, such a sensor senses and records ECG continuously. Each symptom trigger by a patient may initiate transfer of an ECG data strip.

Figure 17:
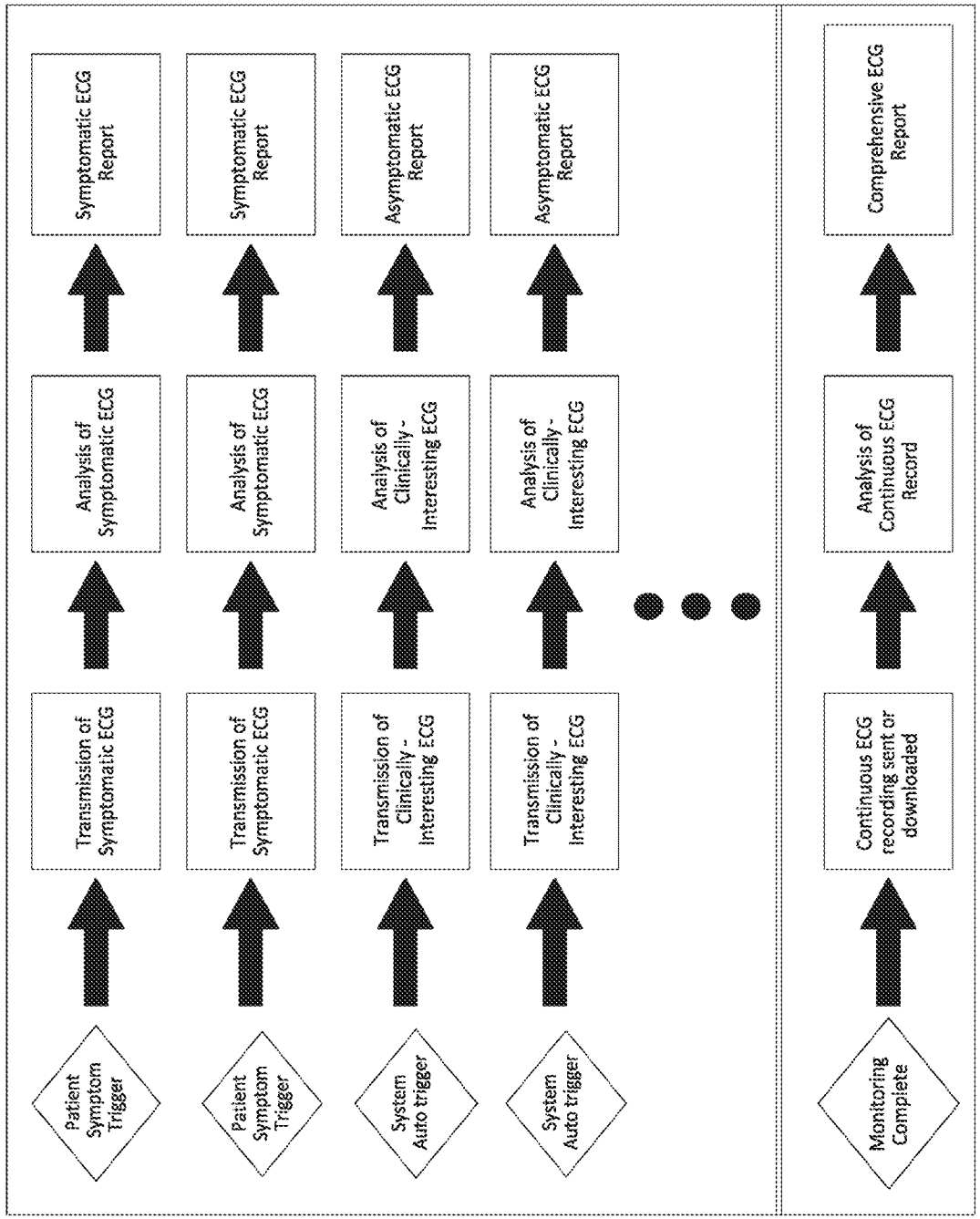
FIG. 17 is a schematic diagram of an embodiment of an asymptomatic transmission system.

FIG. 17 is a schematic diagram of an embodiment of an ECG monitor system 7000 with both symptomatic and asymptomatic transmission. In some embodiments, each asymptomatic trigger initiates transfer of an ECG data strip such as described above.

Systems for Estimating Burden from R-Peak Sequences Using Neural Networks

Some embodiments disclose a wearable device. The wearable device can comprise sensors for detecting bio-signals of a user, such as ECG signals. The wearable device can process the detected bio-signals through a first subset of layers of a neural network. The wearable device can take the output of a first subset of layers of a neural network, and transmit the output to a computing device (e.g., an external system such as a smart phone or a server) to further process the data through a second subset of layers of the same neural network in order to derive a characteristic of the user, such as an indication of past cardiac arrhythmia and/or predict a future onset of arrhythmia. In some embodiments, the computing device is a processor external to the wearable device or a processor within the wearable device. In certain embodiments, as described herein, at least some of the computation may occur on one more processors external to the wearable device and/or one or more processors within the wearable device.

In some embodiments, the output of the first subset of layers are an indication of R peak sequences. In other embodiments, the output of the first subset of layers are an indication of RR intervals. The wearable device can process the ECG signal through the first subset of layers of the neural network to receive R peak sequences from the output of the first subset of layers. The wearable device can transmit the R peak sequences to an external computing device. The external computing device can process the R peak sequences through the second subset of layers of the neural network, and receive as an output of the second subset of layers a derived characteristic of the user (such as the indication of past cardiac arrhythmia and/or predict a future onset of arrhythmia, burden of atrial fibrillation, etc).

There has been a lot of recent activity exploring the usage of wearable sensors to detect cardiac arrhythmias like atrial fibrillation (AFib). The wearable sensors used for such studies fall broadly into two categories. The first category of devices are electrocardiographic (ECG) monitoring devices. The second category of devices are photoplethysmography (PPG) based devices. When using PPG-based devices for AFib detection, the results have been mixed. For example, in one study, utilizing the heart rate and step count data from a PPG based device, a deep neural network based algorithm on a dataset where PPG data was obtained from a patient cohort immediately before and after cardioversion for AFib in a clinical setting resulted in decent results, but the same approach and algorithm had a more modest performance on a much broader ambulatory cohort of patients with persistent AFib. The reasons for the poor performance on the ambulatory cohort of patients could be numerous but the most influential factor is very likely the poor PPG signal quality for heart-rate estimation in uncontrolled settings. This raises the need to detect AFib more accurately using heart rate data derived from ECG signals recorded using a wearable cardiac monitor like the ECG monitoring devices.

AFib burden is the fraction of time that a patient spends in the AFib state. Recently, the notion of AFib burden has gained a lot of attention due to studies demonstrating the association of AFib burden and the risk of ischemic stroke in adults. Therefore cardiac monitoring solutions where one can quickly and accurately estimate the AFib burden of a patient can lead to meaningful medical interventions for patients who have been identified with having a higher risk for stroke.

For clinical analysis, a patient's ECG signal recorded using a cardiac monitoring device is typically segmented into episodes of varying durations and of different rhythm types. A normal, healthy patient will typically be in a state of a normal rhythm referred to as Normal Sinus Rhythm (NSR). Various heart conditions can manifest as patterns of irregular/abnormal heart beats known as cardiac arrhythmias which in turn translate into irregular/abnormal patterns in the ECG signal. There are various types of cardiac arrhythmias such as atrial fibrillation. A patient could switch back and forth between a normal rhythm and one/many of the different types of cardiac arrhythmias or could even be constantly in one of these abnormal rhythms like AFib. AFib burden is the fraction of time that a patient spends in a state of atrial fibrillation. Atrial flutter is another arrhythmia that is closely related to AFib and increases the risk for stroke. AFib and atrial flutter are at times difficult to discern from each other and are typically grouped together for burden calculations due to similar clinical significance. Therefore, for the purposes of this disclosure, embodiments will be described in reference to AFib, but it is understood that some embodiments can apply also (or only) to atrial flutter.

The QRS complex is a dominant feature of an ECG signal. The peak within the QRS complex is commonly referred to as the R-peak. Some embodiments detect R-peak signals from the ECG signal. Once R-peaks are detected, the instantaneous heart rate can be estimated as the inverse of the duration between two consecutive R-peaks (referred to as the RR-interval). A key signature of AFib episodes is high RR-interval variability.

Figure 18A:
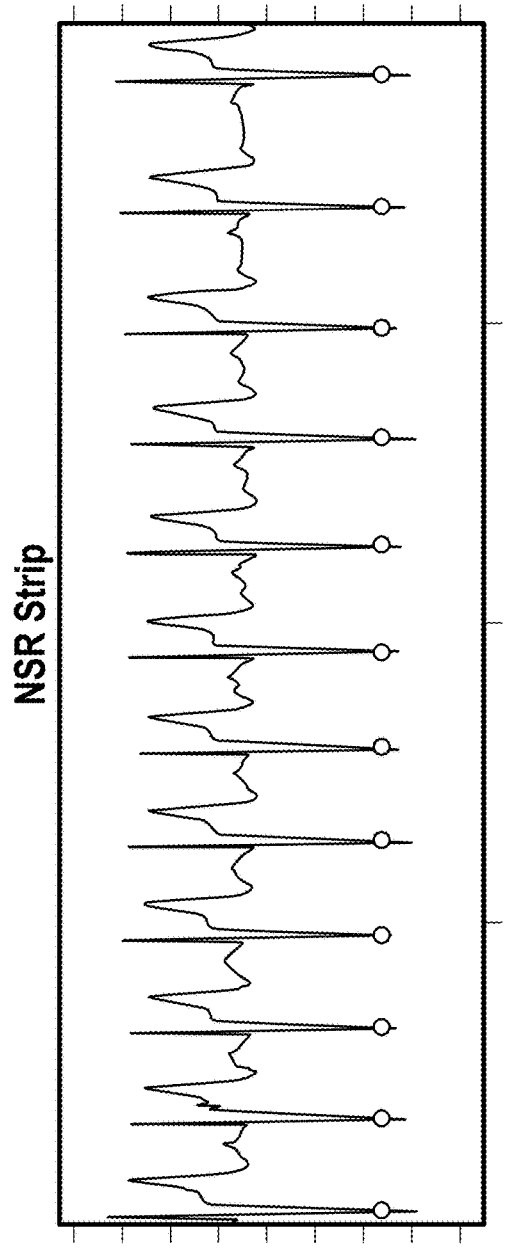
FIG. 18A is a graph of an embodiment illustrating reading from ECG strips corresponding to NSR rhythms.
Figure 18B:
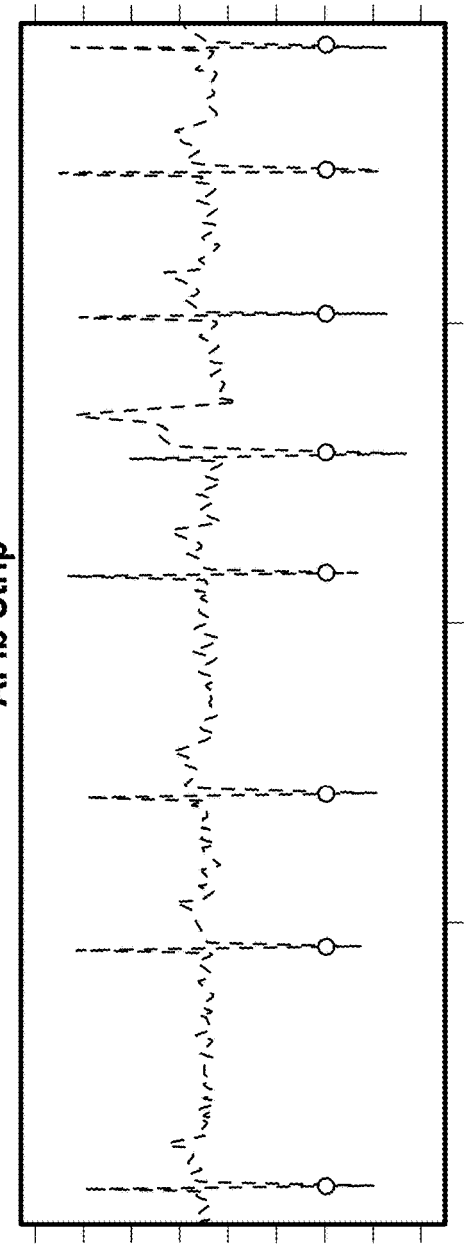
FIG. 18B is a graph of an embodiment illustrating reading from ECG strips corresponding to NSR rhythms.

FIG. 18A is a graph of an embodiment illustrating reading from ECG strips corresponding to NSR rhythms. FIG. 18B is a graph of an embodiment illustrating reading from ECG strips corresponding to NSR rhythms. The dots indicate the location of the R-peaks.

The ECG signal recorded from a patient can be segmented into episodes of different rhythm types and then the AFib burden can be compute by calculating the fraction of time spent in the AFib state. However, if the computation is based only on the extracted sequence of R-peak locations (and not the whole ECG signal), estimating the AFib burden becomes a different algorithmic problem. A scenario where such an algorithm could be useful is when we might want to avoid excessive computations on the monitoring device itself (using the entire ECG signal) or when we might want to limit the amount of data that is transmitted from the monitoring device using wireless communications to computer servers where the AFib burden is calculated.

Described herein are embodiments that detect AFib reliably using heart rate data obtained from a wearable cardiac monitor. Some embodiments can also estimate the daily AFib burden of patients reliably.

In some embodiments, the algorithm (e.g., a neural network) can estimate AFib burden over shorter analysis windows (e.g., duration in the order of a half hour or one hour).

In some embodiments, the burden over a longer period of time (e.g., longer than the shorter analysis windows) can be determined by accumulating the burden predictions over the analysis windows. For example, the burden can be accumulated over non-overlapping analysis windows of half-hour duration. Given the R-peak sequence over an analysis window of half-hour, the RR-interval sequence within the analysis window is derived. This RR-interval sequence is then transformed into a sequence of RR-interval sub-sequences by extracting the RR-interval sub-sequences from a set of possibly overlapping sliding windows of duration w (contained with the analysis window) and shifted by an amount s. The RR-interval sub-sequence obtained from each sliding window is padded/truncated so that all sub-sequences have the same length M. For example, if there are $N_w$ such sliding windows within the analysis window, the dimension for the temporal sequence is ($N_w$, M). The temporal sequence feeds into a neural network model for making burden predictions. For the purposes of explaining the concept, w was chosen to be 30 seconds, s chosen to be 25 seconds and M chosen to be 42. The portion of the neural network (e.g., a first subset of layers of the neural network) on the monitor can process the detected cardiac signals to generate the RR-interval data (and/or the RR-interval sub-sequences), and transmit the RR-interval data to a remote computing device. The remote computing device can process the RR-interval data (such as by processing through a second portion of the neural network (e.g., a second subset of layers of the neural network) to make inferences, such as a likelihood of arrythmia. In some embodiments, the neural network can be trained to make a determination on use of the wearable device, such as an indication that the user should wear the device longer due to a higher risk of a potential negative health event, or that the user is at low risk and can end their wear period earlier.

Advantageously, such segregated processing of the data can have many technical benefits. For example, such selective transmission of data that is partially processed can decrease power consumption for the wearable path. The wearable patch is not required to store the entire data processing algorithm (such as the entire neural network), but may only need to retrieve a subset of the neural network layers to process. Thus, the data processing on the wearable device can be much faster, require less computations, and use less battery via the processing. The analysis on the wearable patch side may not require full on-board rhythm analysis which can often times be very highly power consumptive, reducing battery life. Decreased battery consumption can prolong the use of the wearable device, such as the time period between device replacement, battery recharging, and the like. Moreover, the wearable device can have longer monitoring times to get a fuller picture of a patient's cardiac rhythms.

Another advantage for remote analysis based on RR-interval data may allow for greater sensitivity and accuracy than analysis on the path. Because of the memory, processing, and battery restrictions on the wearable patch, analysis on the wearable patch can be limited by these restrictions. Remote analysis can process the data through a wide variety of algorithms, even algorithms based on a decision tree of determinations and occurrences.

Moreover, the wearable patch can send a smaller dimensionality of data than the entire detected cardiac signal. Advantageously, less network throughput is required. The wearable patch can send sufficient data for remote data processing even when wireless network conditions may not be optimal. Moreover, because only a subset of the neural network need be uploaded to the wearable patch, the wearable patch can be updated with updated neural network computer-executable instructions or downloadable executable faster and under weaker network conditions, and can occur more frequently.

Furthermore, because of the lower battery and power requirements, a smaller CPU or a smaller battery can be used to result in a much smaller form factor for the wearable patch. In addition, the reduction of battery and power requirements for the data processing frees the battery and power budget for the wearable device, such that the wearable device can perform other critical tasks, such as running other critical software processes, or powering other hardware devices, such as more electrodes, other sensors such as accelerometers, or running the same hardware and software for a longer period of time.

The neural network encoding approach advantageously allows for very sophisticated algorithms to be run from data on a battery constrained device. One application of this would be to aggregate the encoded data from the device in real time, and run algorithms that will assess the overall risk of a subject developing a certain clinical outcome. As such, the system can inform the user of a wear period dynamically. For example, if after the wearable device aggregates a certain amount of data, the remote computing device may determine that the subject has very low risk for developing a certain clinical outcome. The system can inform the user to the wear period early. Conversely, if the computing device has determined that the user is at a high risk for a certain clinical outcome, the system can inform the user to wear the device longer.

Another technical advantage of having a first subset of layers of a neural network output the RR interval data to be sent for remote processing is that the algorithms for making inferences remotely can be updated without having to update the wearable patch. For example, an updated algorithm or neural network can be updated on the remote computing device via an update to the second subset of layers, whereas the same first subset of layers can be used on the wearable device. The technical advantage is that the second subset of layers can be selected based on a decision tree, updated or swapped with other algorithms, and the like without having to update the wearable patch, making the system more compatible with other algorithms.

Example High Level Architecture of the Burden Prediction Model

Figure 19:
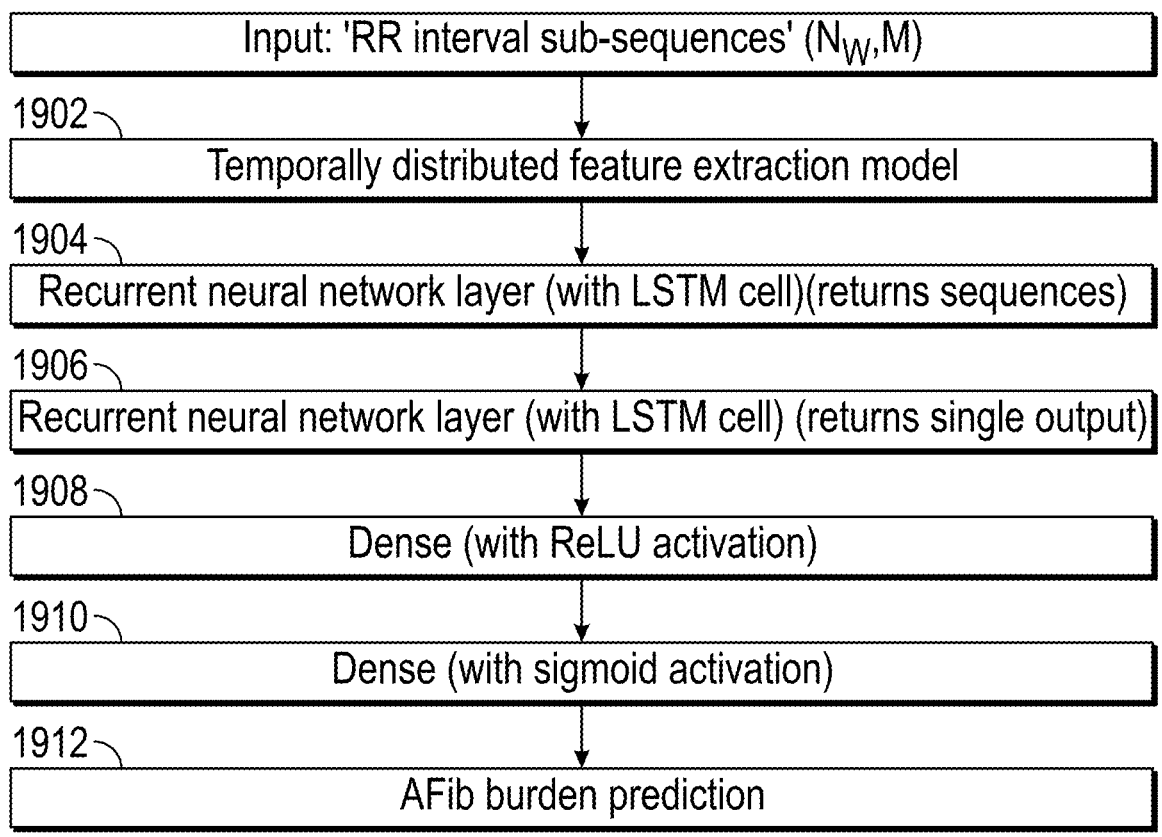
FIG. 19 is a high level architecture of the burden prediction model.

FIG. 19 is a high level architecture of the burden prediction model. The burden prediction model takes as input RR-interval sub-sequences and produces an AFib burden prediction. Here Nw is the number of sliding windows and M is the size of the RR-interval sub-sequence extracted from each sliding window.

The first layer 1902 is a temporally distributed feature extraction layer which extracts a 32-dimensional feature vector for each RR-interval sub-sequence obtained from the sliding windows. The output of this layer is a transformed sequence of dimension ($N_w$, 32). This transformed sequence then feeds into two Recurrent Neural Network (RNN) layers 1904, 1906 with Long Short Term Memory (LSTM) cells. The first RNN layer 1904 returns another transformed sequence of dimension ($N_w$, 32) while the second RNN layer 1906 returns a single output of dimension 32. This is followed by two Dense (fully connected) layers 1908, 1910 producing a scalar value representing the AFib burden for the analysis window.

Figure 20:
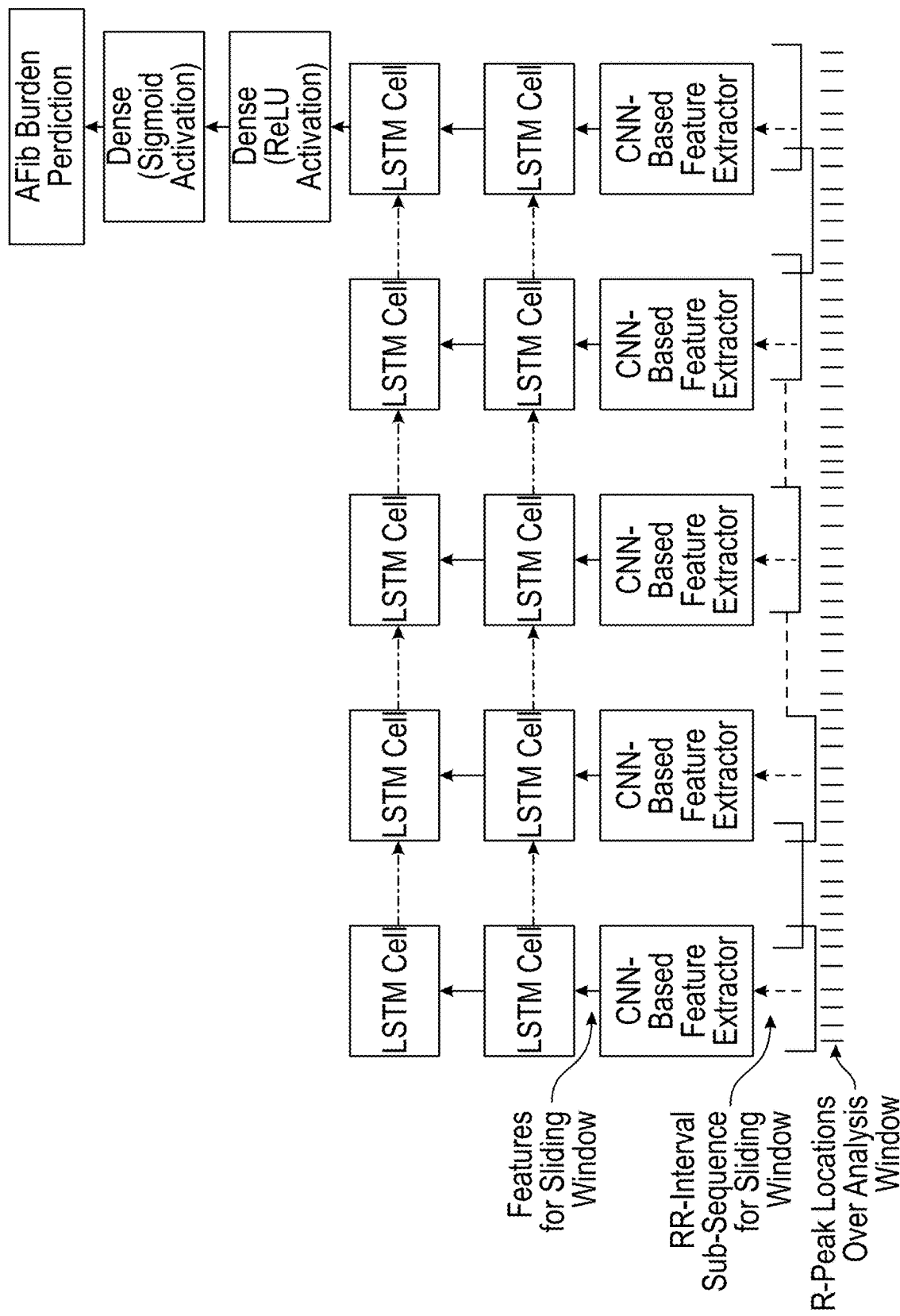
FIG. 20 is an embodiment of the high level architecture of FIG. 19.

FIG. 20 is an embodiment of the high level architecture of FIG. 19, illustrating the LSTM architecture in more detail.

Figure 21:
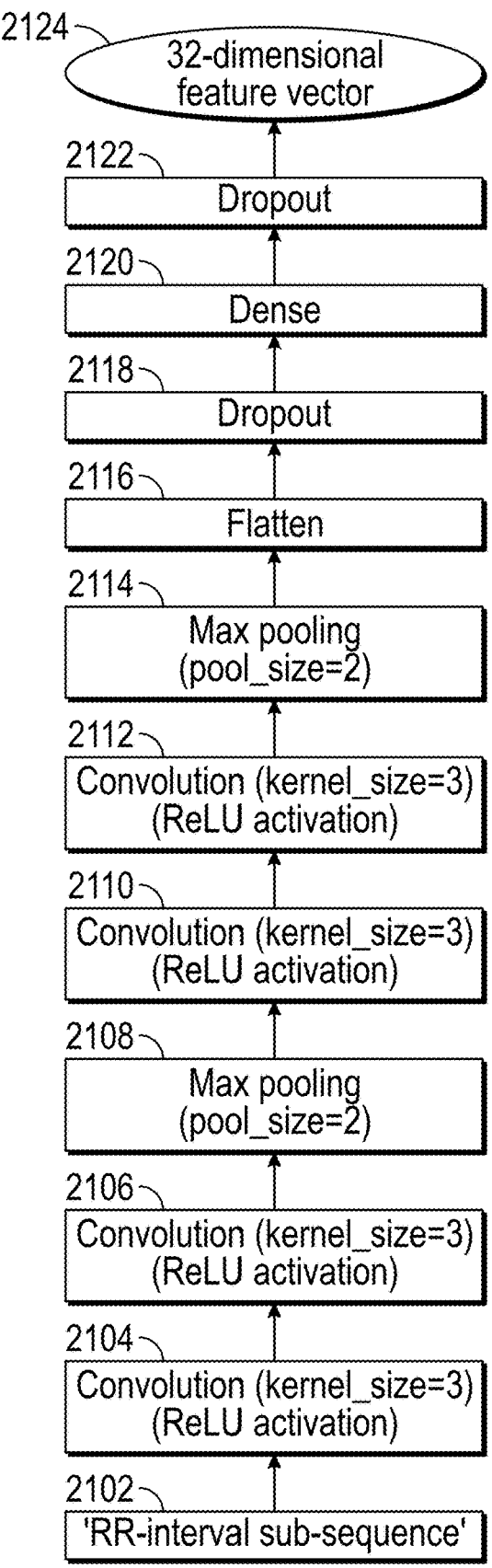
FIG. 21 is an embodiment of the feature extraction model of FIG. 19.

FIG. 21 is an embodiment of the feature extraction model of FIG. 19. As shown, the model for the feature extraction can be temporally distributed over sliding windows in the first layer of the model. The model for feature extraction which is temporally distributed over the sliding windows can be itself another neural network with multiple layers.

At the start of FIG. 19 and step 2102 of FIG. 21, the feature extraction model takes in as input an RR-interval subsequence of length M which is processed by a set of one-dimensional Convolutional layers and Max-pooling layers at steps 1902, 1904, 1906 of FIG. 19 and at steps 2104, 2106, 2108, 2110, 2112, 2114 of FIG. 21. This is followed by a Dense (fully connected layer) which outputs a feature vector of dimension 32 at steps 1908, 1910 of FIG. 19 and 2120, 2122 of FIG. 21. The intent of this feature extraction model is to learn features that are indicative of the presence/absence of AFib within each sliding window of duration w.

For the neural network, a loss function that can be used is the mean (over all samples) of the absolute difference between the burden prediction coming from the model and the true burden value:

$$L = \frac{1}{N}\sum_{i=1}^{N} |\hat{b}_i - b_i| \tag{1}$$

Here, $\hat{b}_i$ is the burden prediction output by the model for the $i^{th}$ window in the dataset, $b_i$ is the true burden for that window and N is the total number of samples in the dataset.

In some embodiments, the parameters of the feature extraction network (e.g., FIG. 21) can be learned separately first. This is done by adding one more Dense (fully connected) layer with a scalar output and sigmoid activation to the feature extracting network and then training the resulting model to do binary classification for detecting the presence of AFib in the 30-sec ECG strips.

The parameters of the feature extracting network thus obtained are then frozen and the resulting feature extracting network is plugged into the burden prediction model (FIG. 20). The subsequent layers (recurrent network layers and fully connected layers) of the burden prediction model are then trained on the half-hour windows described in Section 4.2.

The feature extractor network is trained over a much larger and diverse set of ECG strips and directly learns features that are indicative of the presence/absence of AFib. When training the remaining layers of the burden prediction model, the number of parameters that have to be learned are reduced and therefore the search for the optimal parameters possibly happens faster. In contrast, if the entire network were to be trained at the same time, the number of parameters that have to be learned simultaneously is larger and the model is exposed to a less diverse set of ECG strips. This increases the risk for over-fitting and possibly explains the wider gap between the validation loss and the training loss.

Figure 22A:
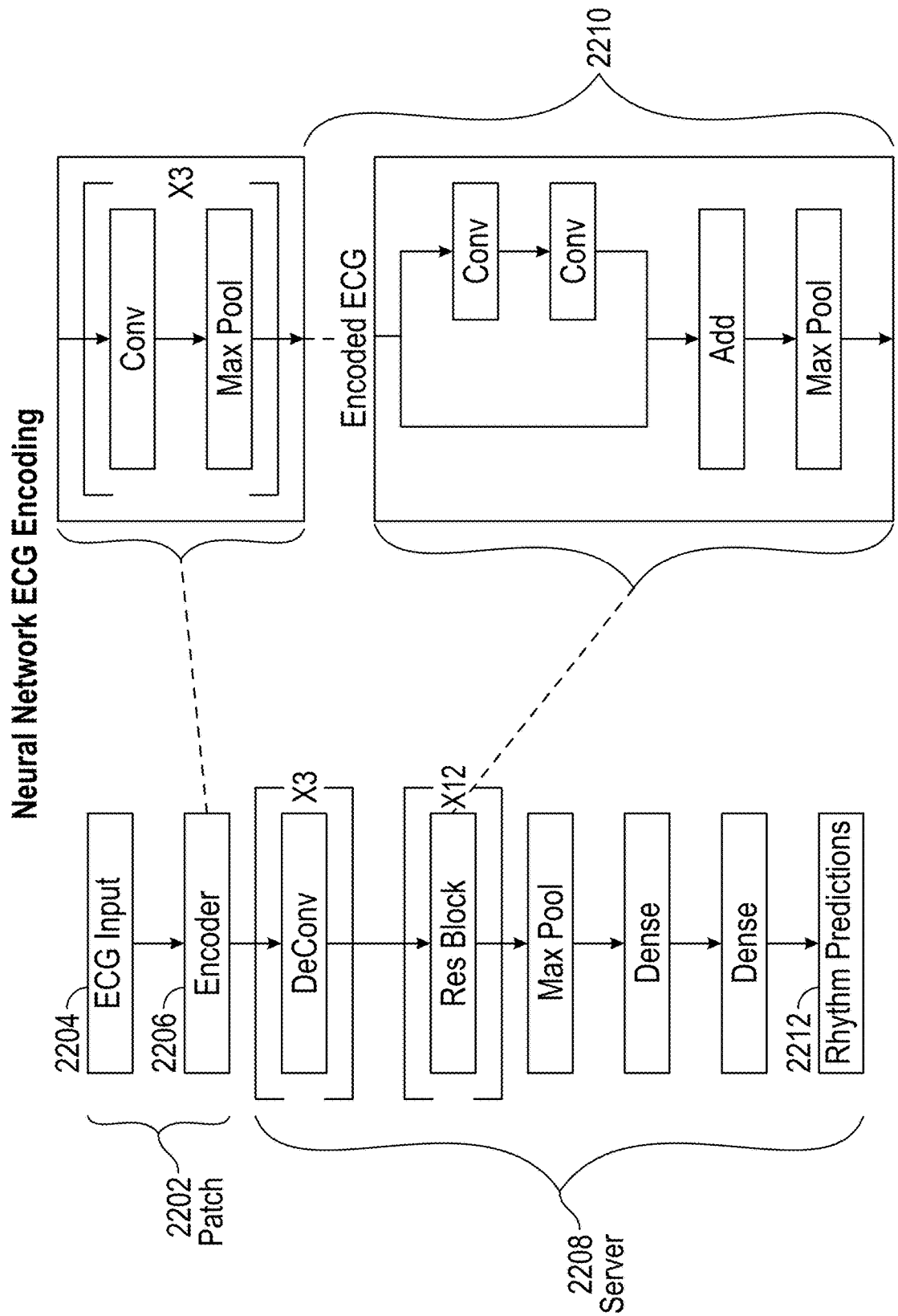
FIG. 22A is a schematic diagram of an embodiment of a system for predicting rhythm annotations using neural network encoding.

Systems for Estimating Burden and/or Predicting Rhythm Annotations Using Neural Network Encoding Some embodiments disclose a wearable device that can process the detected bio-signals through an encoder that includes a first subset of layers of a neural network. FIG. 22A is a schematic diagram of an embodiment of a system for predicting rhythm annotations using neural network encoding. In some embodiments, the system can make one or more predictions, such as predicting rhythm annotations or estimating burden for cardiac rhythms including Atrial Fibrillation and/or Atrial Flutter. The wearable device, such as a cardiac monitor patch 2202, can process an ECG input 2204 through a first subset of layers 2206 of a neural network, such as an encoder. The wearable device can receive the output of a first subset 2206 of layers of neural network, and transmit the output to a computing device 2208 (e.g., an external system such as a smart phone or a server) to further process the data through a decoder that includes a second subset of layers 2210 of the same neural network in order to derive a characteristic of the user 2212, such as an indication or prediction of past cardiac arrhythmia and/or predict a future onset of arrhythmia.

Figure 22B:
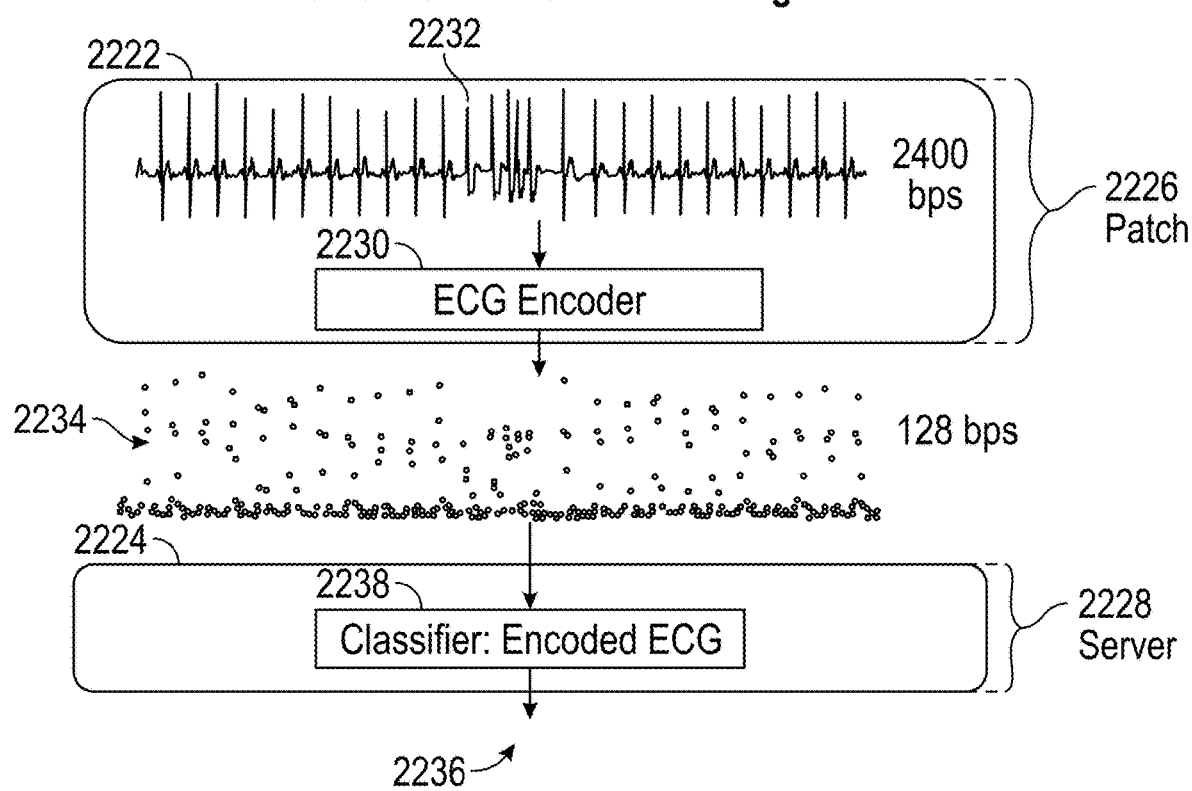
FIG. 22B is a schematic diagram of an embodiment of a first and second subset of layers within a single neural network.

In some embodiments, the first subset and the second subset of layers are within one neural network. The neural network can be designed such that the output of a first subset of layers can output data at a smaller dimensionality than the input to the neural network, and the output of the second subset of layers can be designed to provide an indication of a user characteristic, such as a past or future prediction of AFib. FIG. 22B is a schematic diagram of an embodiment of a first and second subset of layers within a single neural network. The neural network can be trained simultaneously on both the first subset of layers 2222 and second subset of layers 2224. For example, if a neural network has 10 hidden layers, the first 4 layers is processed on the wearable device, such as a cardiac monitor patch 2226, the output of the $4^{th}$ layer, which is of lower dimensionality than the input (e.g., has good data compression features) to the $1^{st}$ layer, is transmitted to an external computing system, such as a server 2228. The external computing system processes the output of the $4^{th}$ layer through the 5-$10^{th}$ layers. The dimensionalities of each layer of the neural network can be designed to output a certain data size (e.g., output dimensions for each convolution or pooling layers). For example, the patch 2226 can include an ECG encoder 2230 that receives ECG data 2232 at 2400 bits per second (bps). The patch 2226 can process the ECG data 2232 through a first subset of layers 2222 of the neural network (such as within the ECG encoder 2230) and output a smaller dimensionality of data 2234, such as data at 128 bps. The output data 2234 can be transmitted to an external server 2228. The external server 2228 can include a classifier 2238 that processes the output data 2234 through a second subset of layers 2224 of the neural network and outputs an indication or prediction 2236 of the patient that it is trained for. The entire neural network, including the first subset 2222 and the second subset 2224 of layers can be designed and trained as a single neural network.

In some embodiments, the output of the first subset of layers can be a smaller dimensionality than the input to the neural network. As such, instead of transmitting the entire ECG signal (e.g., the input to the neural network) from the wearable device to the external computing device, the wearable device can transmit a smaller amount of data to the external computing device, such as the 128 bps output data 2234 of the first subset of layers instead of the full 2400 bps ECG signal 2232. Advantageously, less network throughput is required to derive the indication of past cardiac arrhythmia and/or predict a future onset of arrhythmia.

Figure 22C:
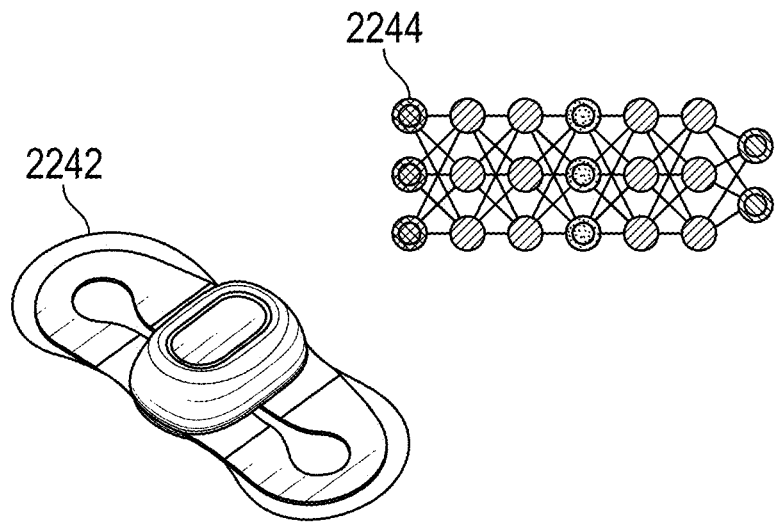
FIG. 22C is a schematic diagram of an embodiment of a system for processing a subset of layers in a neural network on the patch.
Figure 22C:
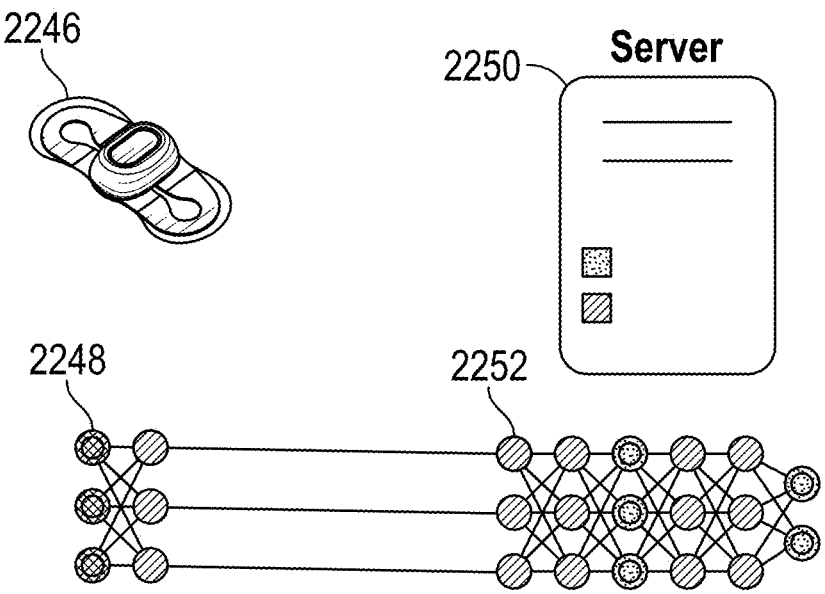

Moreover, instead of processing the ECG signal on the wearable device through all layers of the neural network in order to derive the indication of past cardiac arrhythmia and/or predict a future onset of arrhythmia, the wearable device can process the ECG signal through only a first subset of the layers (such as through an encoder) of the neural network via the ECG encoder 2230, and transmit the output of the first subset to an external device 2228 that processes the second subset of layers (such as through a decoder or classifier 2238). FIG. 22C is a schematic diagram of an embodiment of a system for processing a subset of layers in a neural network on the patch. The patch 2242 can process all layers of the neural network 2244 to receive an indication of prediction of AFib. However, such processing can require high memory and power requirements (which in turn can lead to a larger form factor, a larger sized patch) and increased battery usage leading to shorter use time. However, in other embodiments, the patch 2246 can process a first subset of layers 2248 of a neural network, and an external server 2250 can process a second subset of layers. Advantageously, the wearable device performs a smaller amount of computations and requires less memory to store data between layers.

Moreover, the wearable device 2246 can be smaller in size due to a smaller battery, processor, and other electronic devices required to process only a subset of layers of the neural network. The wearable device can have more resources to perform other tasks. For example, in one scenario, the wearable device 2242 may have enough computational power and battery to process the ECG signal internally and identify AFib for 5 days. However if the wearable device 2246 could compute the first subset of layers of the neural network on the wearable device 2246 and the external computing device 2250 process the second subset, the system as a whole may be able to identify both AFib and atrial flutter over the span of 20 days. Some embodiments disclosed herein can reduce network throughput, reduce computational requirements, and/or memory storage of the wearable device. Advantageously, the wearable device can preserve battery life by using less of the processor.

Certain disclosed embodiments herein improve on memory requirements of the wearable device. If the wearable device is to process a first subset of layers of the neural network and the external computing system the second subset, the wearable device has to store less data (e.g., software executable instructions for the first subset of layers and not the entire neural network). Thus, the electronic files are much smaller in size. Advantageously, the wearable device not only has less memory requirements, but the neural network can also be loaded and processed faster than the full neural network. Moreover, updating the software embedded within the wearable devices can occur much faster, under weaker network connection conditions, and can be programmed to occur more frequently. Furthermore, more neural networks can be stored in the wearable device. For example, instead of a single full neural network being stored in memory, the wearable patch can store the first subset of layers for 5 neural networks in local memory.

Figure 22D:
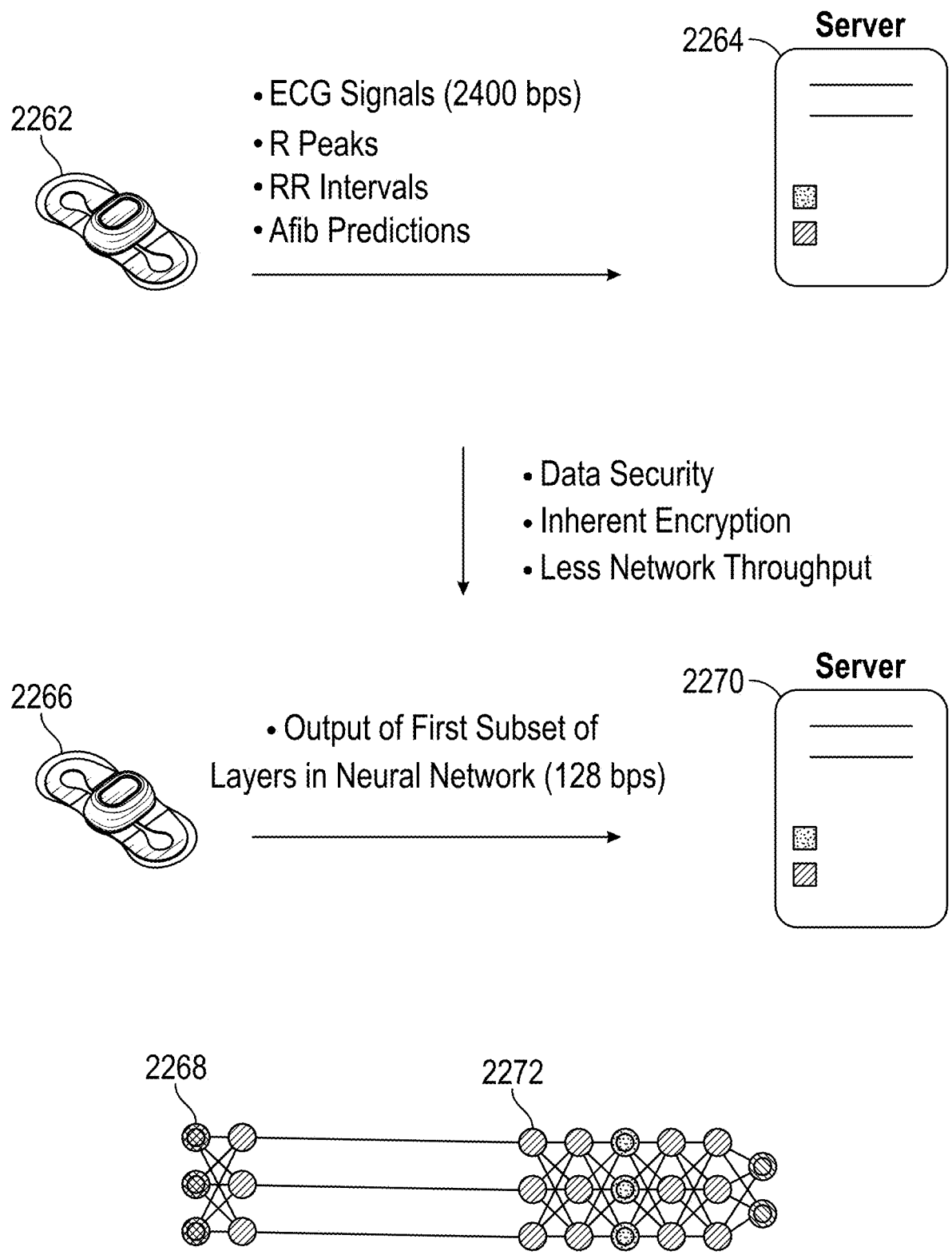
FIG. 22D is a schematic diagram of an embodiment for transmitting the output of a first subset of layers to a server.

In some embodiments, because the purpose of the external computing device is not to reconstruct the ECG signal but rather to derive some user characteristic (e.g., predict rhythm classifications such as AFib), the data that is transmitted from the wearable device does not have to be sufficient to recover the full fidelity of the ECG signal. Thus, the neural network can be trained to generate an output in one of its layers that is a smaller dimensionality than the ECG signal input, and transmit much less to the external computing system to perform the other layers of the neural network. FIG. 22D is a schematic diagram of an embodiment for transmitting the output of a first subset of layers to a server. The patch 2262 can transmit the full ECG signal (e.g., at 2400 bps), or other characteristics of data to the server 2264. However, such data can be hacked and sensitive data retrieved by an unexpected third party. Some embodiments disclose processing a subset of layers of the neural network on the wearable device, which provide a technical advantage over processing the entire ECG signal remotely. Transmitting the entire ECG signal at 2400 bps, or a combination of R peaks, R intervals, and other characteristics, from the wearable device to the external computing system can require more network bandwidth than if the wearable device transmits the output of the subset of layers that are of smaller dimensionality than the ECG signal. Instead, some embodiments of the present disclosure include a patch 2266 that processes a subset of layers 2268, and outputs the first subset of layers to a server 2270 that performs the remaining layers 2272 of the neural network. Advantageously, the data being transmitted can be outputs of a layer in a neural network, which provide for enhanced data security and encryption.

Some embodiments improve on security of health data. For example, if the entire ECG signal, R peaks, RR intervals, or a final determination of the likelihood of AFib was transmitted from the wearable device to an external computing system, a third party may intercept such data and discern sensitive health data of a user. Instead, some embodiments disclosed herein transmit output of an intermediary layer of the neural network (such as the output of the encoder) to be processed by subsequent layers externally (such as the decoder). The transmitted data can be output of a layer in a neural network, which inherently provides encryption of data for data transmission. Thus, even if a third party were to intercept such data, they would not be able to decode the data, nor reverse engineer the original input of the neural network.

In some embodiments, the first subset of layers can include less computationally heavy layers whereas the second subset of layers can include more computationally heavy layers. Advantageously, the wearable device can process the less computationally heavy layers, and the external computing systems that are agnostic to the processing of the wearable device can process the more computationally heavy layers (such as in servers with much larger processing power and memory capacity).

In some embodiments, the wearable patch can perform preprocessing on the detected cardiac signals before processing the data through the first subset of layers of the neural network. For example, the wearable patch can perform preprocessing such as downsampling, normalizing, digital filtering, and/or the like. Moreover, the wearable patch can perform more complex preprocessing, such as a discrete wavelet transform, continuous wavelet transform, discrete Fourier transform and discrete cosine transform. These transforms can be beneficial in lossy compression schemes because the transformations transform the data in a way that results in a lot of values in the data being very close to zero. An encoding can then be created to simply store the values with the highest amplitude, which would limit error when reconstructing the signal.

The wearable patch may apply a discrete wavelet transform or a discrete cosine transform, and simply apply algorithms to make inferences on the detected cardiac data. However, such approaches may fail to capture more subtle features that are critical for the end application, such as ECG rhythm classification, because higher amplitude features are favored. In some embodiments, the system can train a neural network encoder on this transformed set of data (e.g., cardiac data that has been preprocessed) in order to more intelligently encode the data needed for the end application. Advantageously, this may be beneficial for some applications, because a transform may already be performing certain actions to the signal needed for the end application, which could lead to a more powerful or simpler neural network encoder design that had fewer parameters compared to one that works off the raw signal.

Figure 22E:
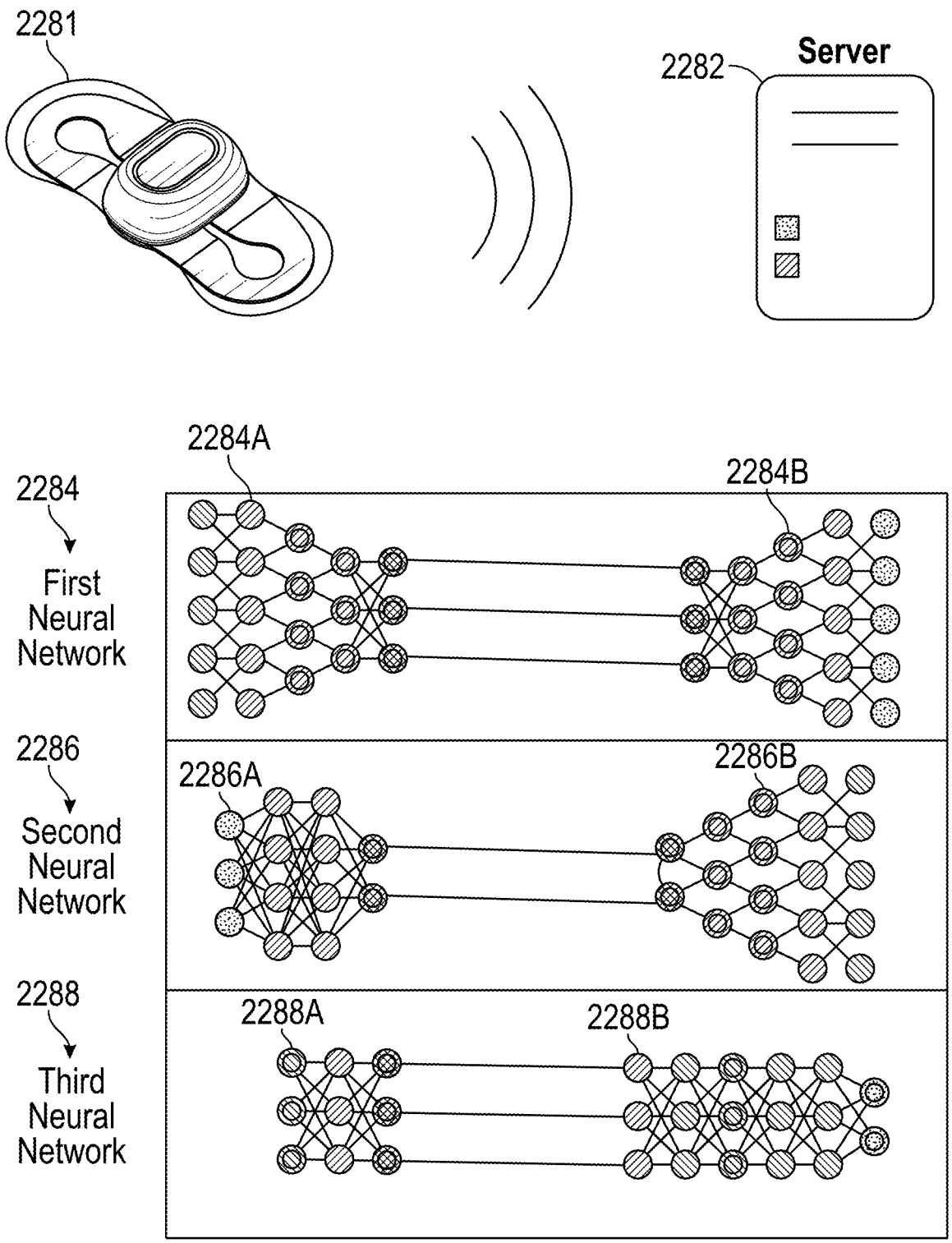
FIG. 22E is a schematic diagram of an embodiment of designing (and/or training) the neural network.

In some embodiments, the neural network can be trained and/or designed to transmit an optimal data dimensionality from the wearable device to the external computing system. FIG. 22E is a schematic diagram of an embodiment of designing (and/or training) the neural network. The patch 2281 can process a first subset of layers 2284A, 2286A, 2288A of a first neural network 2284, a second neural network 2286, and/or a third neural network 2288. The patch 2281 can transmit the output of the first subset of layers to a server 2282. The server can process a second subset of layers 2284B, 2286B, 2288B of the first neural network 2284, the second neural network 2286, and/or the third neural network 2288.

The neural network can be trained and/or designed based on one or more factors, such as available processing power and/or memory of the wearable device (for the purposes of the disclosure, the neural networks will be described as being trained, but the features can be applied for designing or processing data through the neural network, and vice versa). For example, if the wearable device has less processing power, the neural network can be trained to perform less computation and/or perform processing through less layers of the neural network on the wearable device, and process more on the external computing system side. The patch 2281 can apply the third neural network 2288 that includes fewer computations and/or layers of the neural network.

In some embodiments, the neural network can be trained according to network availability between the wearable device and the computing system. For example, the neural network can be trained to process more layers and/or transmit a smaller data dimensionality from the wearable device to the external computing system when the network throughput is lower. The patch 2281 can apply the second neural network 2286 that includes a smaller data dimensionality being transferred to the server 2282 for when the network connection is weak (or below a threshold).

In some embodiments, the neural network can be trained according to available battery life of the wearable device. For example, the neural network can be trained to process less layers on the wearable device when the battery life is lower. The patch 2281 can apply the third neural network 2288 that includes fewer computations and/or layers of the neural network.

In some embodiments, the neural network can be trained according to the desired outcome. For example, the patch 2281 can apply the first neural network 2284 that includes more outputs of the neural network, such as more characteristics of the user. For example, if the patient is in critical care or has an indication of AFib, the patch 2281 can apply the first neural network 2284 and process more layers and nodes through the first subset of layers 2284A, such that the server 2282 can output more information via the outputs of the second subset of layers 2284B.

In some embodiments, the software in the patch 2281 can include instructions for a particular neural network designed (and/or trained) for a particular application. For example, a neural network can be selected for a patch 2281 with certain technical constraints (e.g., memory or processor), and to serve a particular purpose (e.g., predict AFib), whereas another neural network can be selected for a different patch with different characteristics and for different purposes. For example, an accurate detection of AFib can require more data from the patch than another desired purpose. Thus, a patch that is to detect AFib may have software that computes more layers than another patch.

In some embodiments, the software in the patch 2281 can be designed (and/or trained) based on performance metrics. For example, the software can select a neural network that is designed to produce a certain accuracy in detection and/or a certain false alarm rate.

In some embodiments, the software in the patch 2281 can include a plurality of neural networks. The patch 2281 can select a particular neural network out of the plurality of networks. For example, the selection can be based on a neural network designed for low battery power or network connectivity (e.g., switching to a neural network that processes less on the patch or transmits less data through the network).

In some embodiments, the neural network can be trained to recreate the original input signal to the neural network, such as the ECG signal, RR interval information, R peak information, a metric derived from the ECG signal, accelerometer data, impedance, temperature, audio (e.g., snoring), ambient light, and/or the like. The patch 2281 can transmit data of a smaller data dimension to server 2282 for the server 2282 to recreate the original input signal, or a derivative thereof, such as the original input signal sampled at a lower frequency, lower quality signal, signal with a certain threshold for reconstruction error, and/or the like.

Figure 22F:
FIG. 22F is a schematic diagram of an embodiment for designing, training, and/or selecting a neural network based on a current activity of the user.
Figure 22F:
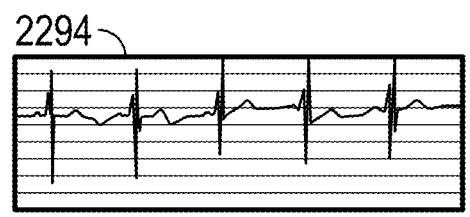
Figure 22F:
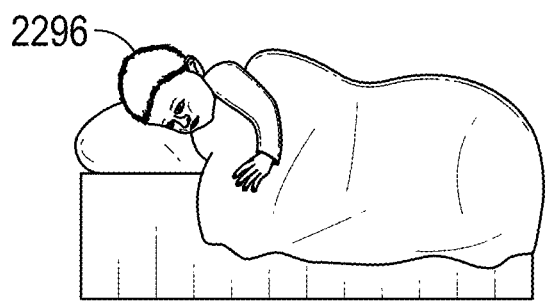
Figure 22F:
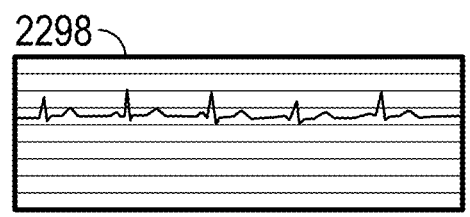

In some embodiments, the neural network can be trained according to the current activity of the user. FIG. 22F is a schematic diagram of an embodiment for designing, training, and/or selecting a neural network based on a current activity of the user. For example, the user can be sleeping 2296 or running 2292, or subject to certain medical treatment that may require different types of peak sensitivities. There are certain activities that may require higher precision or accuracy to be able to effectively detect heart beat irregularities. If the activity requires higher R peak accuracy (e.g., for a user who is sleeping 2296, and signal levels 2298 are less affected by motion artifacts—and thus can rely more confidently on the ECG signal—than a user who is running 2292, so a higher R peak accuracy is preferred for the running user 2292 for a more accurate prediction. For the running user 2292, a more robust encoding process may be used to ensure data accuracy), neural network can be trained such that the wearable device may transmit data of higher resolution. In contrast, for a user who is running 2292, the R signal levels 2294 may be clear (e.g., clearly show R peaks), and thus, a may require lower R peak sensitivity. In this scenario, the patch can select a neural network that is designed to not require higher R peak sensitivity, which can lead to advantages described herein, such as reduced processing power or network throughput.

Training of models, such as artificial intelligence models is necessarily rooted in computer technology, and improves on models by using training data to train such models and thereafter applying the models to a new set of user data. Such training involves complex processing that typically requires a lot of processor computing and extended periods of time with large training data sets, which are typically performed by massive server systems. Training of models can require logistic regression or forward/backward propagating of training data that can include input data and expected output values that are used to adjust parameters of the models. Such training is the framework of machine learning algorithms that enable the models to be applied to new data (such as new biometric data) and make predictions that the model was trained for based on the weights or scores that were adjusted during training. Such training reduces false positives and increases the performance of detection of AFib.

In some embodiments, the wearable device can store a plurality of neural networks and can apply a neural network based on one or more characteristics, such as characteristics of the wearable device, network, current activity of the user, etc. For example, the wearable device can process a first neural network if the battery life is low, or a second neural network if the network throughput is high.

In some embodiments, the wearable device can process the ECG signal continuously through the first subset of layers of the neural network as the wearable device detects the ECG signal in real time. The wearable device can transmit the output of the first subset of layers continuously to the external computing device, and the external computing device can process the received output through the second subset of layers of the neural network in order to derive a characteristic of the user (e.g., cardiac arrhythmia) in substantially real-time. Advantageously, the external computing device can identify cardiac arrhythmia in substantial real-time of occurring with the user while reducing network throughput, memory requirements, and processing power requirements. Moreover, more powerful algorithms and neural networks, which would not have been able to be performed on the wearable device itself due to device restrictions nor completely on external computing systems due to input requirements, are now feasible.

In some embodiments, the neural network can include a first neural network and a second neural network. The first neural network (e.g., a temporally distributed feature extraction model) can receive as inputs one or more types of data, such as the ECG signal of a user, R peak data, RR interval sub-sequences (e.g., RR intervals in 30 second sliding windows), encoded features, and/or the like as further described herein. The first neural network can process the inputted RR interval sub-sequences and generate Atrial Fibrillation (AF) features for each sliding window. The output of the first neural network can be fed into the second neural network including recurrent layers with Long Short Term Memory (LSTM) cells. The LSTM cells can process the AF features of the current sliding window and past sliding windows to process the data using a transfer learning approach, where over the course of multiple sliding windows, the LSTM can advantageously predict an indication of a cardiac arrhythmia that takes into account data longer than the 30 second window.

In some embodiments, the first neural network and the second neural network is trained in stages. The first neural network can be trained first. Training data of 30 second intervals can be fed into the first neural network, and the weights can be adjusted based on the expected output of the first neural network. After the first neural network is trained, the weights of the first neural network can be frozen, and the second neural network can be trained. The second neural network can be trained based on longer intervals of data that are fed into the first neural network in 30 second windows, and the outputs are fed into the second neural network with LSTM cells. The second neural network can make predictions of AFib over the longer data sets, and the predicted outputs can be used to adjust the weights of the second neural network. Once the second neural network is trained, the weights of the first neural networks can be unfrozen, and both the first and second neural networks can be trained simultaneously using further training data.

As wearable bio-signal processing applications grow, there is an increasing need to improve the sophistication and utility of these applications. A common scenario is to have a small, battery-powered wearable, with an array of sensors measuring bio-signals processed and, optionally, transmitted in real-time or near real-time. Since device size will affect comfort, which in turn influences compliance and thus usefulness, it is advantageous to have as small of a device as possible. This introduces several constraints to the system—mainly battery life and processing capability—which in turn can negatively affect user experience by requiring the user to charge the battery or resulting in lower quality analytics and lower compliance. These constraints typically limit the sophistication of processing that occurs on the device, so an option utilized by many applications is to offload processing to systems with fewer constraints, such as smartphones, cloud servers or base stations.

Within this paradigm, a trade-off exists between the amount and type of data offloaded for additional processing. Ideally, the full-fidelity, raw bio-signals are offloaded in real-time to maximize processing sophistication on the lesser constrained part of the system. Unfortunately, within the limits of current technology, this is typically infeasible due to the battery cost and technical limitations of transmitting full-fidelity signals in real-time or even timely manner. A way to overcome this limitation is to send some smaller representation of the signal, thus minimizing power requirements and maximizing the time between battery charging or replacement, or the potential monitoring duration of a device if powered by a single battery charge.

There exist many strategies for creating this alternative representation. Depending on the application, custom-designed algorithms can be used to select features uploaded for further processing. An example of this strategy is a Mobile Cardiac Telemetry (MCT) device, or a wearable activity tracker capable of detecting and uploading the location of heart beats derived by algorithms running on the device, which could then be further analyzed to detect heart arrhythmias by more sophisticated algorithms on a cloud server. Another example is a wearable device that uses accelerometry to analyze gait, assess activity levels, and the risk of falls by uploading the results of the on-device step counting algorithm. The limitation with this set of approaches is that the selected feature may not be optimal for the end application, and the device-side algorithms may also be more computationally burdensome to compute than needed.

Another common approach would be to compress the raw bio-signal data in a way that allows reconstruction of the signal. Commonly used techniques include lossless and lossy compression schemes. Lossless compression, while allowing for optimal processing on cloud-based servers, does not typically provide a high enough compression ratio to reduce the data transmission burden sufficiently to be viable. Lossy compression techniques, such as wavelet-based compression, can achieve a high level of compression relative to the amount of error introduced during reconstruction. While this strategy may work well for certain applications, there is no guarantee that the reconstructed signal will keep the necessary information for the end application, since their objective is only to minimize signal reconstruction error. This type of objective is driven primarily by signal features with a high amplitude, and may ignore or distort features with small amplitude characteristics. Depending on the application, signal features that have relatively small amplitude may be critical to the end objective, such as with the subtle P-waves in an ECG associated with atrial depolarization, critical to detected rhythms such as atrial fibrillation and complete heart block.

System and methods disclosed herein achieves an optimal balance for all elements in a system: device processing burden, system transmission burden, and end application utility. This is accomplished utilizing neural network encoding, which can be used to generate a scheme that compresses raw bio-signal data in a computational friendly manner, preserving information needed for a specific end application. A neural network can encode a signal into a compressed format, and then reconstruct the signal. More generically, a neural network architecture can be built into encoder and decoder sections.

For this application, the encoder section would be responsible for compressing the raw bio-signals, would run on the target device, and would result in an output that has a smaller dimensionality than the input.

The decoder section would be responsible for producing predictions for a target application, starting from the encoded layer of the neural network, and would be employed elsewhere than the target device, for example, on a smartphone, cloud server, or communication hub/gateway. The encoder and decoder portions are trained as one end-to-end neural network, this would effectively create an optimal encoder and a decoder simultaneously because the encoder and decoder sections are being optimized together for the same objective. This method maximizes the flexibility of the system design, which can lead to the most optimal implementation. For example, the encoder section can be designed to target a specific computational complexity and compression, and the neural network output can be selected to be exactly what is needed for the end application. This technique is ideal for any real-time and near real-time signal processing applications that require high computational complexity and have a mechanism to offload processing.

Devices that utilize electrocardiogram (ECG), photoplethysmogram (PPG) or audio signals to detect both electrical and structural heart conditions in real- or near-real time face challenges outlined above. Certain heart arrhythmias present themselves in subtle ways, for example, in low-amplitude P-wave patterns in ECG recordings, often requiring a high level of sophistication and sensitivity in detection algorithms. To maximize clinical utility, rhythms may be categorized in up to fifteen different classes including noise, which not only rely on beat-to-beat heart rate patterns but also the differences in morphology that can often be elusive, especially in single-lead ECG applications. Existing devices may simply offload the entire raw signal, necessitating frequent charging or battery replacement, or use compression techniques to offload processing, or detect commonly understood features of the ECG signal on the device, and upload those to a separate system for further processing. The features may include the location of ECG morphological features such as QRS complexes, P waves, etc. Due to the limited computation power and battery life of these devices, algorithms will have limited accuracy in their ability to detect these morphological features. Neural network encoding can be employed to transmit a compressed representation of the ECG signal. This representation can be optimized for the specific end application, such as identifying specific cardiac arrhythmias, identifying ECG morphological features such as QRS complexes, classifying beat types, determining heart rate, etc.

In an example implementation of this strategy for real- or near real-time arrhythmia detection from ECG recordings, a neural network could first be trained using a set of 30s ECG strips, sampled at 200 Hz, for example, with 14 distinct rhythm labels for each sample. As a preprocessing step, the 200 Hz signal will be down sampled by a factor of 3 using a moving average filter, and then conditioned using an IIR high pass filter with a 2 Hz cutoff. This input is also scaled to have unit variance. This will leave information in the range of −2-33 Hz, which will contain most of the ECG morphological information. This makes the input dimension of the signal into the neural network 2000×1. As mentioned above, the goal of the first section of the Neural Network is to compress the signal, so it will need to reduce the dimension of the input signal.

In an example embodiment, the encoding section of the neural network would have a sequence of convolutions and pooling layers, where each pooling layer reduces the temporal dimension by a factor of 2. With a sequence of convolution and pooling layers that repeats 3 times, this would result in a temporal dimension reduced by a factor of 8. Also in this example embodiment, the final convolution layer of the encoder section would have 2 filters, which will make the output dimension 250×2 and is referred to as the encoded output.

The next layers of the network employ a strategy to return the temporal dimension size back to its original size at the network input. This could be accomplished using several transposed convolution layers (sometimes referred to as deconvolution layers). The layers of this network up to this point can, in one embodiment, be pretrained to predict the original input signal. In one embodiment, the remaining layers consist of residual convolutional filter blocks. In this example, 12 sequential blocks were used, with each block containing 2 convolutional layers, with a residual connection from the input to output. These blocks also reduce the temporal dimension by a factor of 2 every other block. After the last of these blocks, a time-distributed dense layer is evaluated at each temporal point to predict a unique rhythm class. The above example describes one embodiment of a framework for training an algorithm to encode ECG information in a way that preserves diagnostic information in a compressed format.

In some embodiments, the encoding process can be implemented to perpetually generate ECG features. Using the above example neural network, a 6000-sample length ECG strip will create 250 examples of a feature vector with two dimensions. This can be thought of as every 24 individual ECG samples resulting in two encoded features. Since the nature of this processing is causal, these features can be created perpetually, without any concept of 30s ECG segments. These features can be scaled to be stored in a compact integer representation, and lossless compression can be applied to further reduce the features memory footprint. With a continuous stream of encoded features, a server-side algorithm may employ a number of different strategies to detect events of interest using the encoded features.

In one embodiment for detecting segments that contain an arrhythmia (such as CHB, VT, AFIB/AFL, SVT, AVB etc), the original multiclass algorithm used to train the ECG encoding can be evaluated using 30-second contexts of encoded features that are generated on the patch. This algorithm can be evaluated on a rolling window of 30-second contexts, with or without overlap. Segments that have a high probability of containing an arrhythmia can be used to determine if an event of interest is present.

In one embodiment, the encoding section of the neural network may use a combination of convolutional, pooling and recurrent layers such as LSTM to reduce the dimensionality of the signal.

In one embodiment for detecting VT events, a neural network can be trained using the encoded features to predict sequences of VT in ECG segments that are about 1 second in duration. The benefit of this is that differentiation between more or less severe segments can be made for determining which events are of more interest. For example, longer segments could be prioritized over shorter ones. This algorithm could be used to determine the burden of VT episodes that meet a more specific length criterion. Traditional approaches to VT detection—particularly on a battery-constrained embedded device—relies on beat patterns that exhibit sudden increase in rate.

The reliance on beat detection, for example, the widely used Pan-Tompkins algorithm, whose performance is often poor on wider QRS beats, inevitably limits the ability to reliably discern beat patterns in arrhythmia such as VT. Even when full ECG is present and morphology information can be studied via signal processing techniques, the computational burden is high on a battery-operated device, leading to devices requiring charging once or more times daily and/or battery replacement on both the sensor and the gateway or mobile phone unit. For example, many current Mobile Cardiac Telemetry (MCT) modalities suffer from this requirement, which transfers its burden upon the patient, therefore contributing to lower compliance and lower analyzable time and clinical value from the diagnostic device.

In one embodiment for evaluating AF burden, the original neural network trained to create the ECG encoding can be evaluated over 30-second contexts to determine if the segment contains Atrial Fibrillation (AFIB) or Atrial Flutter (AFL), and the summation of these times can be used to calculate burden. In addition for Atrial Flutter, existing modalities often struggle with the differentiation of AFL from other regular rhythms such as Normal Sinus, since the irregularly irregular beat pattern characteristic of Atrial Fibrillation is not present. This requires closer examination of the signal between beats, which the encoded features allow. Of course, full ECG allows for this as well, but would require more computational power to process the information, which often takes the form of frequency domain analysis and in turn also leads to a less patient-friendly device with charging or battery replacements as discussed with in the MCTs embodiments above.

In another embodiment for evaluating AF burden, the encoded features can be fed into a recurrent neural network over a larger context, for example 30 minutes, to predict AF burden in the same manner as described above.

In another embodiment for characterizing VT, the encoded features can be fed into a network over a larger context, for example 30 minutes, to predict the total duration of VT and/or the number of discrete VT episodes that are present.

In one embodiment for determining heart rate, a neural network could be trained to predict the number of heart beats contained in a segment of time, for example, 3 seconds, using the encoded features. This neural network can be used to predict the number of beats in a segment of time over a sliding window, which can then be used to estimate heart rate at various times. This heart rate information can be used for further refinement or prioritization of events of interests that are detected using other algorithms. A similar strategy would enable the estimation of heart rate variability in lieu of or in addition to heart rate.

In one embodiment for determining ectopic beats counts, a neural network could be trained to predict the number of ectopic beats contained in a segment of time, for example, 3 seconds, using the encoded features. This neural network can be used to estimate the total number of ectopic beats over a window of time, for example, in a 1-, 12- or 24-hour period. Alternatively, combined with the heart beat embodiment described above, this embodiment could be used to estimate the ratio of ectopic to normal beats, for example, expressed as a percentage over a 1-, 12- or 24-hour period. This embodiment, described agnostically above, could be applied to either ventricular or supraventricular ectopic beats, and/or to couplets and triplets of each.

In one embodiment, R-peak locations may be approximated from the reconstructed time series from the encoded features. These R-peak locations could, on their own, be used to calculate heart rate, augment the accuracy of heart rate estimation from an alternate method, or to detect cardiac Pause events defined as a clinically significant gap in time between two ventricular contractions, for example, greater than three seconds. Like heart rates, this information can be used to further filter or prioritize events of interests whose ECG is to be transmitted and reported. In another embodiment, the reconstructed signal itself can be viewed along with portions of full ECG to provide more context, for example, whether low, high, or irregular heart rate continues from the end of the ECG segment. This contextual information can aid in the process of manually requesting more full resolution ECG from the patch based on visual inspection, leading to an overall higher diagnostic acuity backed by human quality assurance.

In an alternate embodiment, heart rates based on these R-peak locations could be plotted alongside the selected ECG strips in a clinical report in a manner that provides greater temporal context for the event shown in the brief (e.g., 8- or 16-second strip). The heart rates could be plotted as either instantaneous rates (e.g., based on the interval between two R-peaks), or as a heart rate trend over time with each data point derived from multiple R-peaks. An alternative embodiment could plot the average, max and min heart rates trends simultaneously to provide even greater clinical context.

In some embodiments, a wearable device that utilizes PPG and accelerometry can be used to detect Atrial Fibrillation (AFIB) episodes, and to estimate AFIB burden levels. Sensors in this configuration very commonly suffer from degraded signal quality due to environmental factors, such as being worn improperly, motion of the device, or poor physiological conditions. For this reason, it is advantageous to utilize the full fidelity raw sensor readings in order to detect AFIB or estimate AFIB burden, since the noise can be understood and prevent algorithms from predicting false positives.

Existing strategies may detect heart rate intervals on the device, and use this information to infer AFIB episodes. Signal quality metrics may be separately computed and uploaded. This strategy will suffer when periods of poor signal quality create false heart rate interval readings. Using the strategy outlined above, a neural network could be developed to predict AFIB episodes or AFIB burden from the raw PPG/accelerometer signals, which also encodes the signal in a compressed representation. This network can learn to encode the information in a way that is least prone to false predictions due to poor signal quality. The encoding can be run on the device, and the encoded data can be uploaded so that a decoding section would be evaluated on more powerful servers. In addition to identifying AFIB episodes and AFIB burden, encoded sensor data from a wearable PPG device could be used to characterize pulse rate or detect other heart arrhythmias, such as ventricular tachycardia, pause, atrioventricular block etc. They can also be used to detect health conditions such as diabetes, hypertension, depression, congestive heart failure, sleep apnea etc.

In another embodiment, encoded features can be optimized to describe waveform components of ECG beats in addition to R peaks, e.g. P-waves, T-waves and/or segments between points in a waveform. A neural network can be trained on the encoded features to estimate PR intervals, whose patterns can discern between subtle categorization of AV Block ($1^{st}$ degree, $2^{nd}$ degree Mobitz I I.e. Wenckebach, $2^{nd}$ degree Mobitz II) or characterize Wolff-Parkinson-White syndrome along with inference of QRS width. Some of these less life-threatening, asymptomatic arrhythmias may be desirable to be transmitted, especially if the device does not record and store all signal continuously like event recorders and ILRs or some MCTs where not all of the signal is fully analyzed.

In a similar manner, a neural network can be trained on the encoded features to estimate QT intervals, which can uncover clinically significant findings such as Long QT Syndrome, which may be monitored over the course of the wear time. For example, this QT measurement approach could be used for drug titration, where a patient would adjust drug dosage to determine the optimal mix of drug efficacy and safety on an individualized basis. A neural network can also be trained to detect changes in ST segments, which can be monitored to look for ST elevation or depression which may be warning signs for myocardial infarction.

In another embodiment, the encoding method can be dynamically adjusted and adapted as the system receives and learns more about the characteristics of the signal. It can also be swapped with a different scheme if the target rhythm changes for a specific patient. For instance, instead of a generalized method of detecting arrhythmia types, for certain neurology applications like post-stroke monitoring, the primary focus may be to detect AF, and regardless of heart rate or duration of the episode. A pair of encoding and decoding networks pretrained and optimized for high sensitivity of AF may be used in this case. These different encoders can be learned offline and updated over the air to the firmware when change is necessary, or pre-programmed as an option on the embedded device to be activated when requested. Alternate embodiments might implement algorithms optimized for either sensitivity or specificity performance, in a similar manner.

In certain embodiments, the input signal may include channels from accelerometer and/or gyroscope axes, which can often take up a lot of space due to the number of axes multiplied by the required sampling rate (e.g. 20 Hz to enable inference of step counts). The features in 3-axis accelerometer and/or 3-axis gyroscope signal can be reduced to a smaller dimensionality, which may contain valuable information not just limited to pre-defined physical metrics like magnitude. In fact, characteristics that can only be obtained via higher frequency sampling could be encoded to enable finer distinction between activities. Encoded accelerometer and/or gyroscope features on their own can be used to determine sleep stages and activity levels, step counts, orientation, activity type, etc. Encoded accelerometer and/or gyroscope features on their own, or features from these signals encoded together with ECG, can be used to further differentiate between signal generated by the physiological events such as arrhythmia versus that of motion artifact. The same data is also helpful as one input (trended activity level) to evaluating the health of heart failure patients, for example, in the form of an ambulatory monitor of decompensation events after hospital discharge.

In other embodiments, impedance information, or some other measurement indicative of skin contact such as galvanic skin response may be encoded along with the ECG or independently. A neural network can be trained to detect areas of leads off, and in conjunction with ECG features, be used to filter out segments of unreliable signal. Since the same impedance values can mean different levels of signal quality on different patients and conditions, a simple state-machine type of algorithm on impedance values alone may result in leads-on conditions when signal is actually non-physiological, or on the converse, leads off detected when the signal is actually ECG and therefore analyzable. The former is particularly an issue for ambulatory devices that are prone to noise which can sometimes mimic arrhythmia and therefore result in false positive transmissions, though some of it can be mitigated through hardware design and flexible materials such as on a patch form factor. Decoder algorithms that use encoded features of ECG, together with raw or encoded features of secondary signals such as impedance or accelerometer can further eliminate these false positives, while also ensuring that real ECG signal is not lost due to poor impedance.

In certain embodiments, suspected arrhythmia detected using the encoded features may benefit from further analysis using the full-resolution ECG on the original device. The power savings enabled by an encoder implementation would allow a decoder-based algorithm to request either transmission or on-board analysis of portions of full-resolution ECG stored on the device. A separate algorithm, which may be derived from convolutional neural networks trained on labeled full-resolution ECG, running on restricted regions of the original ECG would be computationally feasible.

In certain embodiments, encoded features may be used to learn and predict arrhythmia such as Atrial Fibrillation or other health conditions that may occur in the near future, enabling early intervention.

In certain embodiments, the processing, either the encoding or the subsequent layers that use the encoded features (decoding), may be done on the intermediate device transmitted prior to long-range connection such as cell or satellite, such as a smartphone or a gateway device. In certain use cases, for example, where raw signal does not need to be written to device memory, which is often an heavy part of battery consumption in these limited power modalities, both encoding and decoding can occur on the device itself, such as a patch, smartwatch, or other wearables capable of continuously monitoring ECG or other signals, and only the encoded signal written. This approach could be useful in a scenario where storage space is limited, but algorithms may need to run on data stored in memory (e.g., data for ECG that occurred in the past).

In certain embodiments, the technique may be applied to other surface or transcutaneous bio-signals other than ECG, such as PPG from the wrist, ear lobe or chest. Wearable devices, often consumer-grade, feature PPG signal capture to enable heart rate trending and in some cases, screening for Atrial Fibrillation. These health insight capabilities are often limited to detection of highly limited duration, e.g. 30 seconds, and require relatively high-power optical sensing, e.g. with green light to reliably capture waveforms through various skin types and motion. The entirety of the PPG cannot be stored or transmitted for more rich contextual analysis of anything beyond simple beat detection in case PPG wave morphology contains signatures unique to arrhythmic blood flow, or to aggregate into more long-term and clinically useful metrics such as AF burden.

In some embodiments, PPG and/or ECG waveforms are encoded in order to infer blood pressure and other cardiac metrics such as blood perfusion, blood volume, cardiac output, ejection fraction, valve function and/or health, etc., where the traditionally computed beat-to-beat or even fiducial point intervals may not be the most useful features. Although certain embodiments are described with PPG, it is understood that ECG can also be used where applicable, and vice versa.

In certain embodiments, the technique may be applied to even more data heavy signal such as EEG. Wearable applications employing EEGs are often limited to laboratory settings due to the number of channels and bulk of devices. Encoded features trained of EEG could enable offloading of high-computational power decoder algorithms to a server and enable mobility of devices that for example, translate brain activity into communication.

In some embodiments, the neural network encoding may be implemented in dedicated hardware, such as an FPGA IC to further reduce battery consumption on the target device. The neural network encoder may be further optimized for an embedded application by utilizing integer math or binary operations.

In some embodiments, image or video streams that result in detection of markers or objects or physiological measurements can use neural network encoding to offload processing to more powerful systems. Example applications would be
- object detection in vehicles, security surveillance systems
- emotional response from facial video
- physiological measurements such as heart rate, breathing based on video streams of face or chest
- detection of seizures
- detection of falls
- augmented reality
- infant monitoring of notable events (crying, breathing issues)

In some embodiments, audio data may be encoded for the purpose of identifying speech events or translating speech in real-time, respiration monitoring, diagnosis of respiratory illnesses, detection of snoring or apnea.

In some embodiments, sonography data may be encoded for the purpose for identifying contraction during pregnancy, detecting and characterizing fetal heart beats, identifying anomalous physiology such as tumors, strokes, blocked arteries, infection, etc.

Computing Systems and Methods

Figure 23:
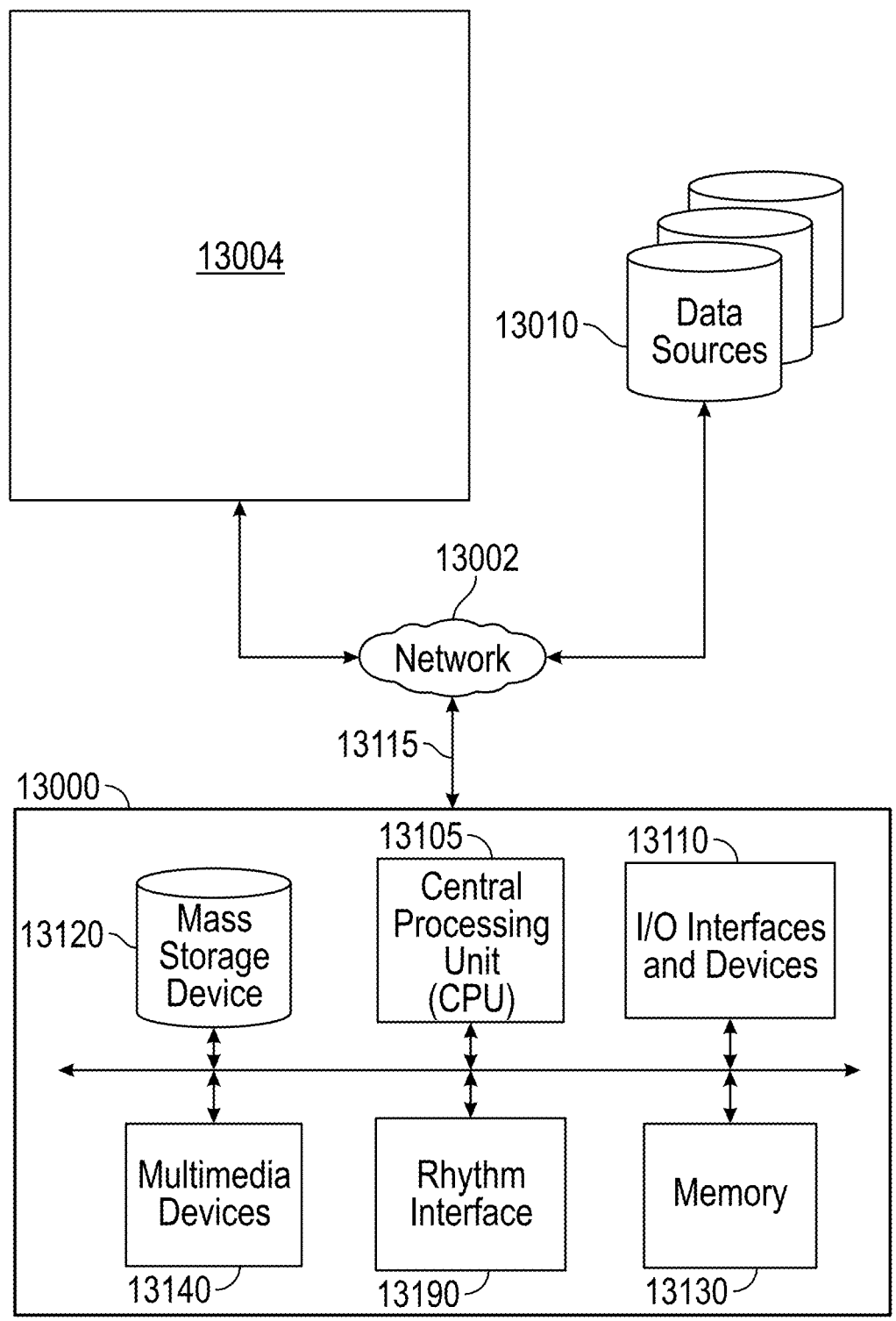
FIG. 23 is a schematic diagram of an embodiment of a computer network system.

In some embodiments, the systems, tools and methods of using same described above enable interactivity and data collection performed by a computing system 13000. FIG. 23 is a block diagram showing an embodiment in which the computing system 13000 is in communication with a network 13002 and various external computing systems 13004, such as a wearable system 13005, a gateway device 13006, which are also in communication with the network 13002. The computing system 13000 may be used to implement systems and methods described herein. While the external system 13004 are shown as grouped it is recognized that each of the systems may be external from each other and/or remotely located.

In some embodiments, the computing system 13000 includes one or more computing devices, for example, a server, a laptop computer, a mobile device (for example, smart phone, smart watch, tablet, personal digital assistant), a kiosk, automobile console, or a media player, for example. In one embodiment, the computing device 13000 includes one or more central processing units (CPUs) 13105, which may each include a conventional or proprietary microprocessor. The computing device 13000 further includes one or more memory 13130, such as random access memory (RAM) for temporary storage of information, one or more read only memory (ROM) for permanent storage of information, and one or more mass storage device 13120, such as a hard drive, diskette, solid state drive, or optical media storage device. In certain embodiments, the processing device, cloud server, server or gateway device, may be implemented as a computing system 1300. In one embodiment, the modules of the computing system 13000 are connected to the computer using a standard based bus system. In different embodiments, the standard based bus system could be implemented in Peripheral Component Interconnect (PCI), Microchannel, Small Computer computing system Interface (SCSI), Industrial Standard Architecture (ISA) and Extended ISA (EISA) architectures, for example. In addition, the functionality provided for in the components and modules of computing device 13000 may be combined into fewer components and modules or further separated into additional components and modules.

The computing device 13000 may be controlled and coordinated by operating system software, for example, iOS, Windows XP, Windows Vista, Windows 7, Windows 8, Windows 10, Windows Server, Embedded Windows, Unix, Linux, Ubuntu Linux, SunOS, Solaris, Blackberry OS, Android, or other operating systems. In Macintosh systems, the operating system may be any available operating system, such as MAC OS X. In other embodiments, the computing device 13000 may be controlled by a proprietary operating system. Conventional operating systems control and schedule computer processes for execution, perform memory management, provide file system, networking, I/O services, and provide a user interface, such as a graphical user interface (GUI), among other things.

The exemplary computing device 13000 may include one or more I/O interfaces and devices 13110, for example, a touchpad or touchscreen, but could also include a keyboard, mouse, and printer. In one embodiment, the I/O interfaces and devices 13110 include one or more display devices (such as a touchscreen or monitor) that allow visual presentation of data to a user. More particularly, a display device may provide for the presentation of GUIs, application software data, and multimedia presentations, for example. The computing system 13000 may also include one or more multimedia devices 13140, such as cameras, speakers, video cards, graphics accelerators, and microphones, for example.

The I/O interfaces and devices 13110, in one embodiment of the computing system and application tools, may provide a communication interface to various external devices. In one embodiment, the computing device 13000 is electronically coupled to a network 13002, which comprises one or more of a local area network, a wide area network, and/or the Internet, for example, via a wired, wireless, or combination of wired and wireless, communication link 13115. The network 13002 can communicate with various sensors, computing devices, and/or other electronic devices via wired or wireless communication links.

Figure 24:
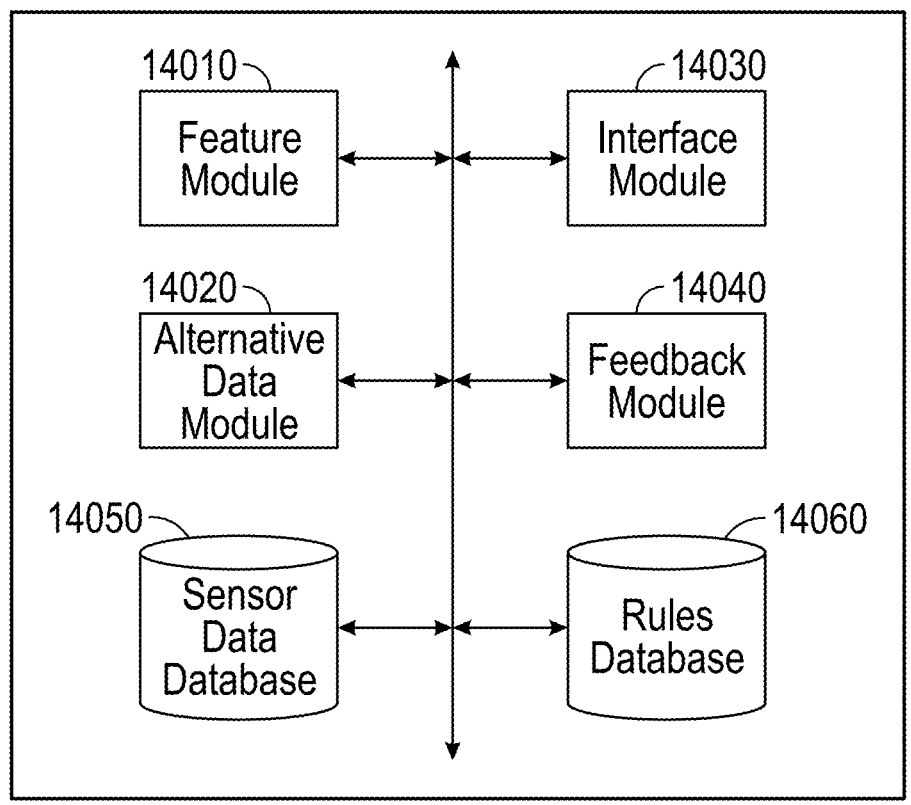
FIG. 24 is a schematic diagram of an embodiment of a programming and distribution module.

In some embodiments, the filter criteria, signals and data are processed by rhythm inference module an application tool according to the methods and systems described herein, may be provided to the computing system 13000 over the network 13002 from one or more data sources 13010. The data sources may include one or more internal and/or external databases, data sources, and physical data stores. The data sources 13010, external computing systems 13004 and the rhythm interface module 13190 may include databases for storing data (for example, feature data, raw signal data, patient data) according to the systems and methods described above, databases for storing data that has been processed (for example, data to be transmitted to the sensor, data to be sent to the clinician) according to the systems and methods described above. In one embodiment of FIG. 24, the sensor data 14050 may, in some embodiments, store data received from the sensor, received from the clinician, and so forth. The Rules Database 14060 may, in some embodiments, store data (for example, instructions, preferences, profile) that establish parameters for the thresholds for analyzing the feature data. In some embodiments, one or more of the databases or data sources may be implemented using a relational database, such as Sybase, Oracle, CodeBase, MySQL, SQLite, and Microsoft® SQL Server, and other types of databases such as, for example, a flat file database, an entity-relationship database, and object-oriented database, NoSQL database, and/or a record-based database.

The computing system, in one embodiment, includes a rhythm interface module 13190 that may be stored in the mass storage device 13120 as executable software codes that are executed by the CPU 13105. The rhythm interface module 13190 may have a Feature Module 14010, an Alternate Data Module 14020, an Inference Module 14030, a Feedback Module 14040, a Sensor Data Database 14050, and a Rules Database 14060. These modules may include by way of example, components, such as software components, object-oriented software components, subroutines, segments of program code, drivers, firmware, microcode, circuitry, data, databases, data structures, tables, arrays, and variables. These modules are also configured to perform the processes disclosed herein including, in some embodiments, the processes described with respect to FIGS. 10 to 17.

Lossless Compression and/or Quantization

In some embodiments of the present disclosure, the system can perform lossless compression on the output of the first set of layers in a neural network before transmitting the data to a remote server to process the data through the second set of layers in a neural network. The lossless compression algorithms may allow the original data to be perfectly reconstructed from compressed data. In some embodiments, the system can perform compression where the remote server can reconstruct the compressed data with an accuracy of a certain threshold, thus reducing loss.

Figure 25:
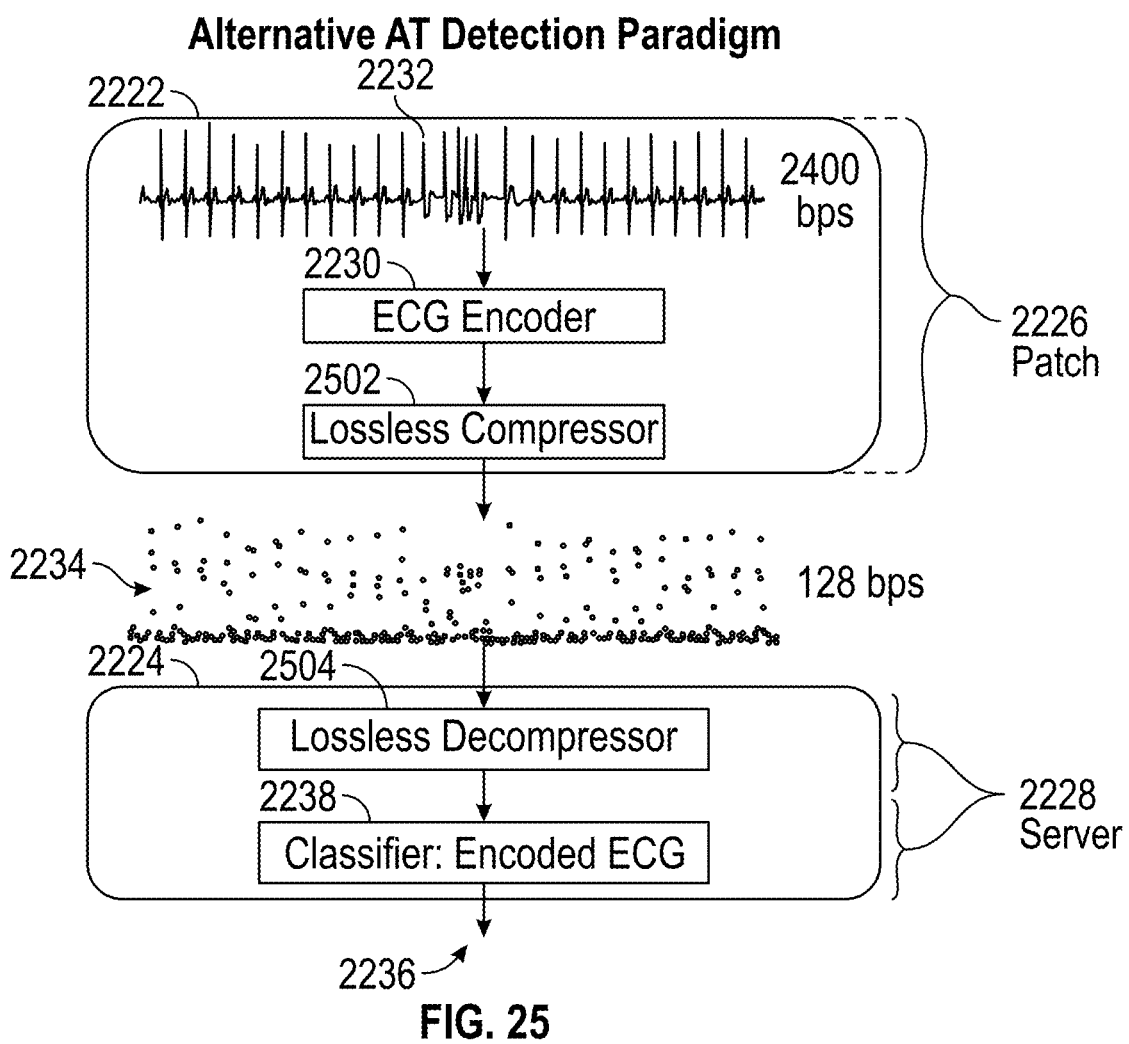
FIG. 25 illustrates an implementation of lossless compression with the ECG encoder.

FIG. 25 illustrates an example of an implementation of lossless compression with the ECG encoder. The patch 2226 can receive ECG data 2232 of a user. The monitor (e.g., the patch 2226) can encode the data through the first set of layers 2222 of the neural network (e.g., via the ECG Encoder 2230) and transmit the encoded output to a lossless compressor 2502. The lossless compressor 2502 can compress the data to an even smaller dimensionality to be transmitted to a remote server 2228. The remote server 2228 can decompress the data via the losses decompressor 2504. The remote server 2228 can then process the decompressed data through the second subset of layers 2224 of the neural network via the classifier 2238.

In one example, a lossless compression scheme can be used to map between output encoded features and a shorter length representation. For an 8 bit integer, a value of 0 as a binary representation "00000000" can be the outputted encoded feature of the first subset of layers of the neural network from the ECG encoder 2230, but the lossless compression scheme can change the "00000000" 8 bit number representation to something else. The lossless compression scheme can have a mapping between values that are outputted from the ECG encoder 2230 to a compressed value. For example, the "0000000" 8 bit number representation from the ECG encoder 2230 can be represented by "10," which only takes 2 bits instead of 8. The lossless compression scheme can use shorter bit length codes for more common output encoded features, whereas longer bit length codes are used for more rare encoded features. Advantageously, less data is transmitted to the remote server. For example, if there are much more 0 values outputting from the ECG encoder 2230, the lossless compression scheme can map a 0 value to "10". However, if a value of 433 is rarely outputted from the ECG encoder 2230, the lossless compression scheme can map a 433 value with a binary representation of "110110001" to "5523".

In some embodiments, the lossless decompressor 2504 can retrieve mapped values that are predetermined. In some embodiments, the lossless decompressor 2504 can retrieve mapped values that are static and do not change. The lossless decompressor 2504 can receive the mapped values from the lossless compressor 2502. The remote server 2228 can map the compressed data (e.g., the mapped values) to actual values that correspond to the ECG encoder 2230. For example, if the lossless decompressor 2504 receives a "10" value and a "5523" value, the lossless decompressor 2504 can map these values to "0" and "443" and output these values accordingly. These values can then be processed through the second subset of layers in the neural network via the classifier 2238.

Advantageously, the dimensionality of the data being transmitted from the patch to the server for a system that (1) encodes the data via a neural network and (2) compresses the encoded data can be smaller than a system with (1) just a neural network encoder (without the lossless compression). Moreover, using lossless compression enables more data to be transmitted to the remote server 2228 while still maintaining the integrity of the data itself because the data can be reconstructed via the lossless decompressor. To illustrate in an example, if there are a plot of 0 values very close to each other, the system can send a representative indication of the plot of 0 values instead of having to transmit all 0 values separately. Advantageously, the data that is being transmitted from the patch to the server can use less network throughput, and can work under tighter network constraints without sacrificing accuracy and performance of the neural network. Moreover, such compression can be another form of encryption that can further enhances the privacy and security of the data as the data travels through various networks from the patch 2226 to the remote server 2228.

As noted herein, some embodiments of the present disclosure train the neural network to compress data, such as via the ECG encoder 2230, through a first set of layers in a neural network in order to reduce the dimensionality of the output. The first set of layers of the neural network is trained to output a certain dimensionality. The compressed data is transmitted to a remote device that applies the output of the first set of layers to the second set of layers of the neural network, which can include the steps described herein, such as decoding the data or determining physiological characteristics of the data.

In traditional neural networks, systems use large number representations, such as a floating point number (e.g., 32 bits of data). A floating point number can represent a very large or very small value, with great precision to many decimal places. These traditional systems use such large number representations for very accurate training of the neural network and processing of data. However, using such large number representations result in inefficiencies in storing, processing, and transmitting the data.

Figure 26:
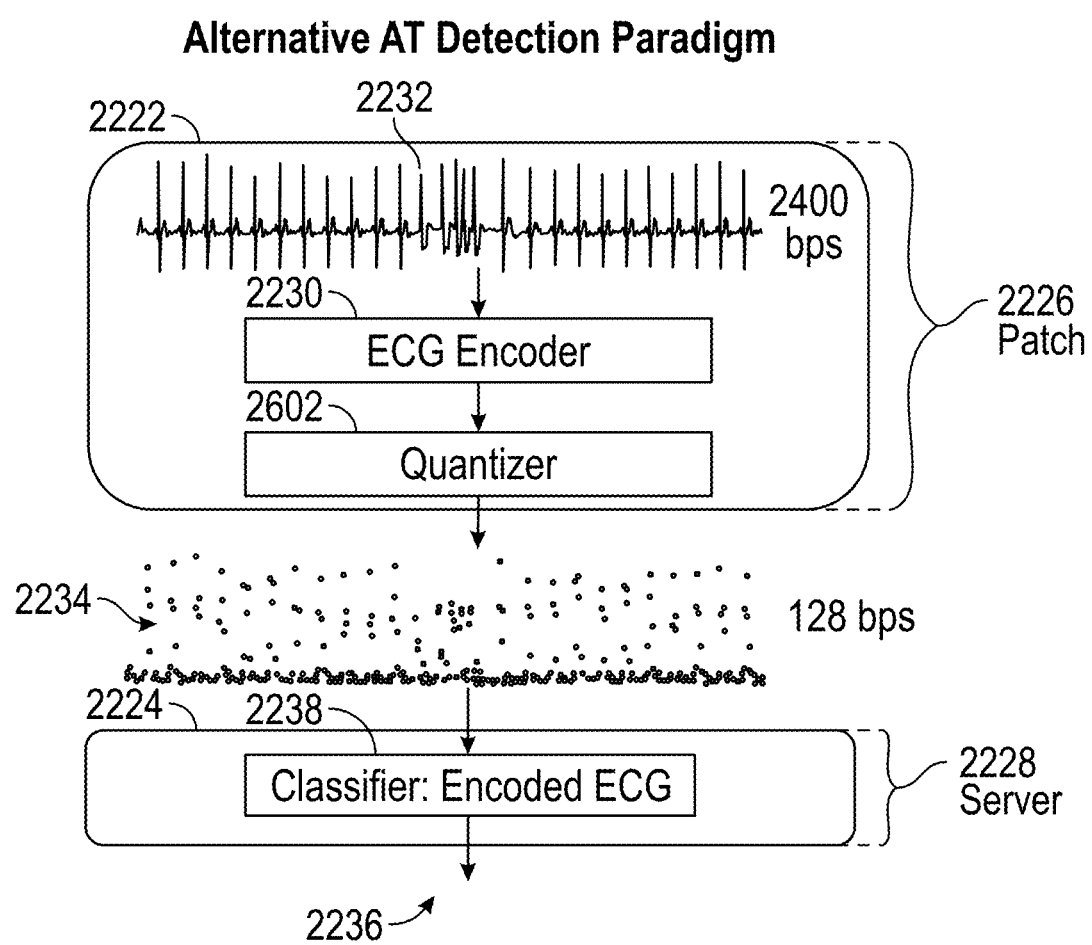
FIG. 26 illustrates an embodiment of a quantizer to perform quantization on the output data of the ECG encoder after processing the first subset of layers in the neural network.

Some embodiments in the present disclosure mitigate such drawbacks by quantizing data. FIG. 26 illustrates a quantizer 2602 to perform quantization on the output data of the ECG Encoder 2230 after processing the first subset of layers 2222 in the neural network. The patch 2226 can receive ECG data 2232 of a user. The monitor (e.g., the patch 2226) can encode the data through the first set of layers 2222 of the neural network (e.g., via the ECG Encoder 2230) and transmit the encoded output to a quantizer 2602. The quantizer 2602 can quantize the data (e.g., truncate or round the data) to be transmitted to a remote server 2228. The remote server 2228 can then process the quantized data through the second subset of layers 2224 of the neural network.

Such quantization can be optimized to have better lossless compression performance while balancing the overall performance of the neural network. The system can quantize the output of the first set of layers of the neural network before transmitting the data to the external server. In some embodiments, quantizing the data can include rounding (e.g., rounding to the nearest integer), truncating, or reducing the number of bits for the data representation.

In some embodiments, the amount of quantization can be determined to optimize the balance between efficiencies and accuracy. A more aggressive quantization (e.g., truncating more bits from the data) can reduce the size of the data representation to a lower number of bits, but can negatively affect the accuracy of the neural network predictions. However, a less aggressive quantization (e.g., truncating less bits from the data) can increase accuracy, but at the cost of increased storage and transmission requirements of the monitor device on the person, increased storage requirements by having to store larger data representations at both the patch 2226 and the remote server 2228, and increased network transfer of data between the patch 2226 and the remote server 2228.

A more aggressive quantization can introduce error into the quantized data, which can lead to degradation in performance of algorithms that use quantization, as noted herein. While a neural network can work to a certain degree in light of the error introduced by quantization, there will be a point where the error will significantly degrade the algorithm's performance. Thus, the amount of quantization can be optimized based on degradation in hardware efficiencies and accuracy of the neural network in its classifications via the classifier 2238.

In some embodiments, the neural network is trained to allow for more aggressive quantization schemes. For example, the neural network can be trained to maximize lossless compression performance. The neural network can be trained by introducing quantization during training in order to reduce degradation associated with the quantization. In some embodiments, the neural network is initially trained without the quantization. Then, the trained neural network is trained again with quantization. Advantageously, the training of the neural network takes into account the quantization. This is particularly relevant here where the neural network is divided into a first set of layers that run on the patch 2226 and a second set of layers that run on a remote server 2228. Advantageously, the results of such training can include a neural network and/or quantization that can better represent low amplitude signals from the quantization. Rather the neural network can adjust the values of its output (e.g., increasing the amplitude of the low amplitude signals) to ensure that the low amplitude signals are taken into consideration, such as by the classifier 2236 of the remote server 2228, to identify features in the signal. For example, the neural network can exaggerate the low amplitude signals such that the signals reach a threshold. Thus, even as the low amplitude signals are processed by the quantization, the remote server 2228 can still register the low amplitude signals. Other systems without such training of the neural network could simply clip the low amplitude signals via the quantization, and the classifier 2238 may not be able to identify features in such signals.

In some embodiments, both lossless compression and quantization can be optimized and applied. In some embodiments, the optimal lossless compression in lieu of the neural network and the quantization can be determined by modeling performance of different lossless compression algorithms or characteristics thereof. For example, the output of features of the neural network can be set to have a distribution centered at 0 with a standard deviation of 1. Then, the system can model how well certain lossless compression algorithms perform under various quantization schemes. For example, if the output of the first subset of layers of a neural network is 128 bits per second, the quantizer can quantize the data to output 100 bits per second. The optimization can be governed at least by the available network and/or network constraints (such as a set number of bits per second or a bit size for the data). Then, lossless compression models (e.g., as described herein) can be applied to find optimal performance on identified features of the neural network at the remote server.

In some embodiments, the optimization can be governed at least by the architecture of the encoder. For example, a first encoder design can be outputting 8 bits and a second encoder design can be outputting 4 bits but outputting at double the sample rate as the first encoder design. In this example, the network constraints can be the same for the first and second encoder. The first encoder design has a less aggressive quantization with fewer outputted features. However in some circumstances, the second encoder design can perform better because of the higher rate of feature generation, in spite of the higher quantization.

In some embodiments, the implementation of quantization into training can apply a tensorflow implementation. During training, the tensorflow can introduce the quantization in the forward pass, but the gradients will be computed without the quantization. This is done so that quantization errors are propagated through the network, but gradients are still smooth and will allow the weight updates to respond appropriately to the errors.

Figure 27:
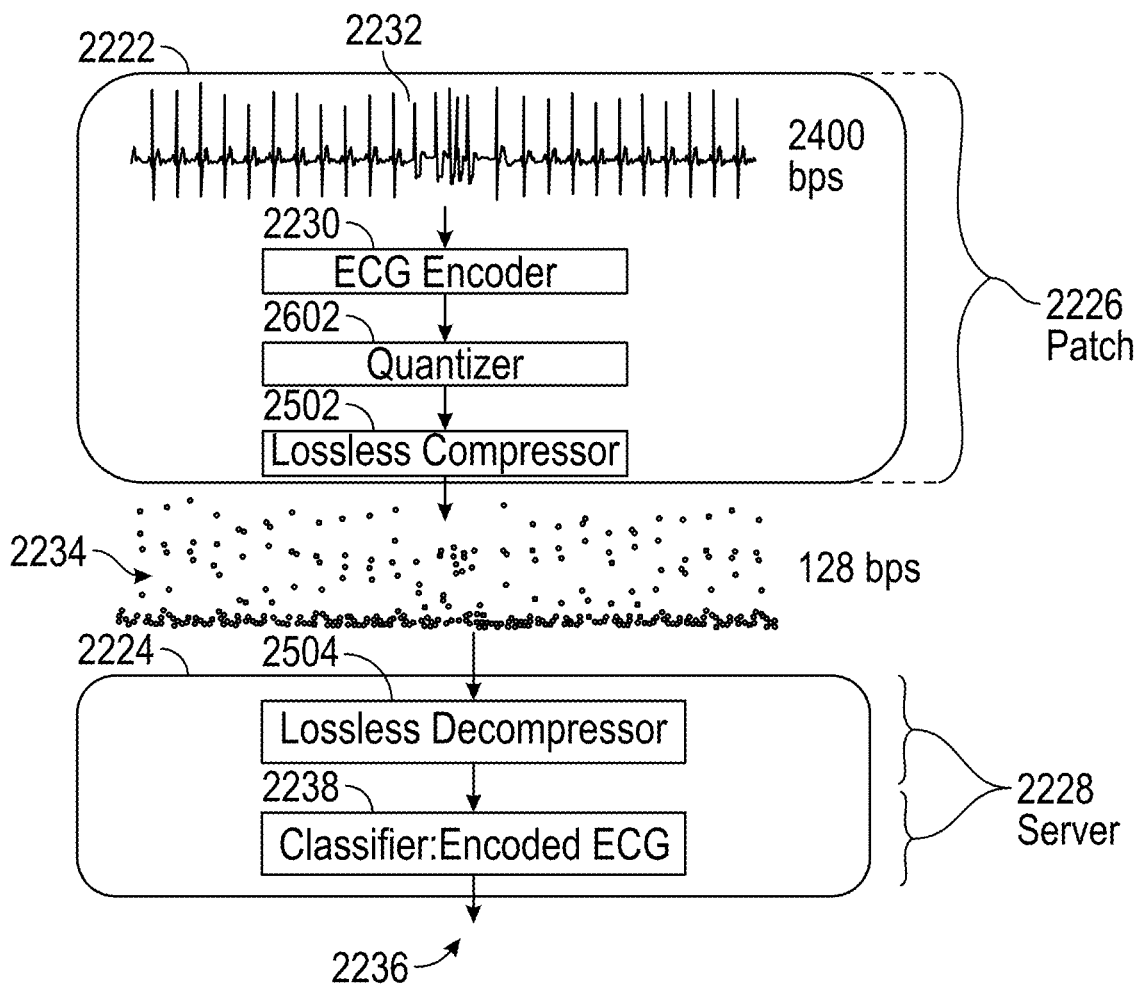
FIG. 27 illustrates an embodiment with both the quantizer and the lossless compression via the lossless compressor and the lossless decompressor.

FIG. 27 illustrates an embodiment with both the quantizer 2602 and the lossless compression via the lossless compressor 2502 and the lossless decompressor 2504. In this embodiment, the output of the ECG Encoder 2230, after the encoder has passed the data through the first subset of layers 2222 of the neural network, is inputted into the quantizer 2602. The quantizer 2602 quantizes the encoded output data. Then, the lossless compressor 2502 can compress the quantized data to be transmitted 2234 to the remote server 2228. The remote server 2228 can then decompress the transmitted data 2234 via a lossless decompressor 2504, and the classifier 2238 can process the decompressed data through the second subset of layers 2224 of the neural network.

Analysis of QT Interval Algorithms

In some embodiments of the present disclosure, the system can quantify QT intervals, which can include quantifying the time between the Q and T morphological features presented in an individual heartbeat. An elongated time between these features can be indicative of a heart condition.

In traditional systems, quantifying the QT interval is typically accomplished by first identifying the different morphological features and simply measuring the difference between specific points on the features. However, systems that do not have access to the full raw ECG data may not be able to apply the traditional methods of quantifying the QT interval.

Described herein are some embodiments that may quantify QT intervals without having access to the full raw ECG signal. In some embodiments, the remote server can receive the encoded features from the encoder, and can reconstruct the ECG signal from the encoded features. Then, the remote server can use signal processing and algorithm techniques for locating morphological features.

In some embodiments, the remote server can train a machine learning algorithm to directly predict the QT interval from a segment of encoded features that contain a QT interval.

In some embodiments, the remote server can train a machine learning algorithm that directly predicts the average QT interval from a window of encoded features that contain one or more QT intervals.

Figure 28A:
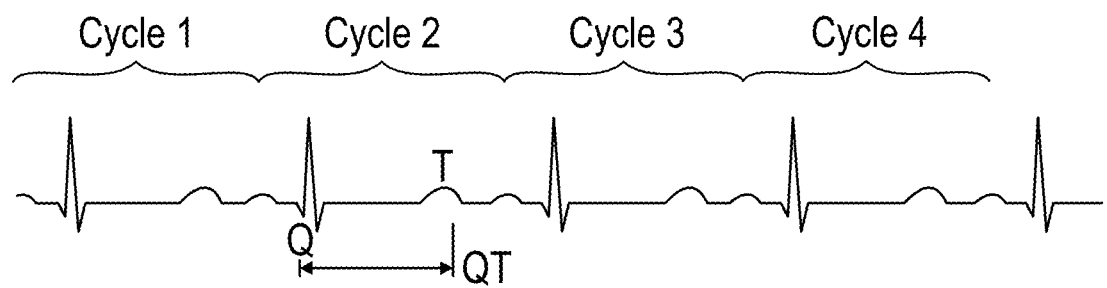
FIGS. 28A and 28B illustrate an embodiment of the process for generating a template beat.
Figure 28B:
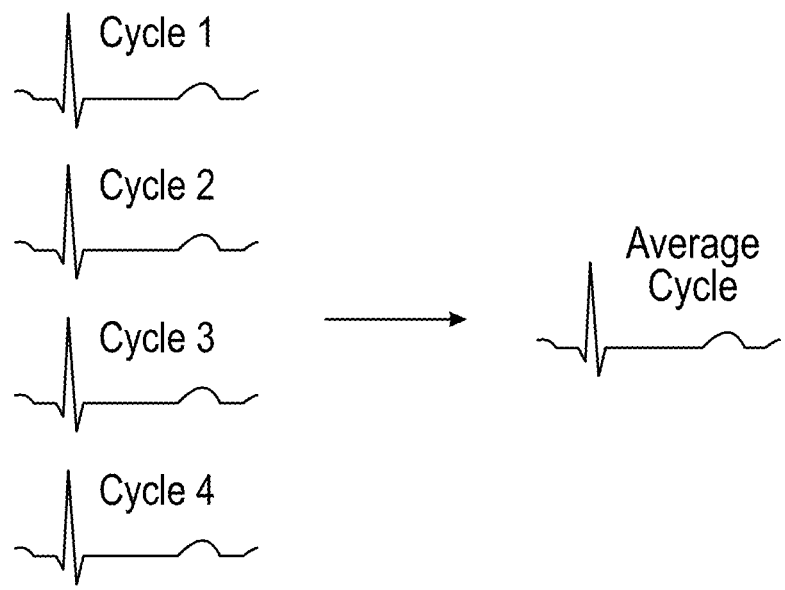

In some embodiments, the system can generate a template beat that is representative of several beats. The template beat can be generated by averaging the raw ECG of a fixed window of samples surrounding a detected beat location. The QT interval can be derived from the template beat using the algorithm techniques or machine learning algorithms described herein. FIGS. 28A and 28B illustrate the process for generating a template beat. For example, FIG. 28A illustrates a window of samples over 4 cycles. Each cycle has a fixed window of samples. The system can determine the number of cycles over a time period or set a number of cycles to be used in the generation of the template beat. FIG. 28B illustrates the generation of the template beat from 4 cycles. In some embodiments, the system determines samples relative to each other. For example, the system can identify corresponding points in each cycle and average each of the samples together. Thus, the 4 cycles illustrated on the left of FIG. 28B can be averaged to generate a template beat on the right.

In some embodiments, the patch can generate the template beat. In other embodiments, the remote server can generate the template beat from the received data from the patch. In some embodiments, the template beat can be processed and identified via data processing through the layers of the neural network. For example, the patch can generate the template beat and input the template beat into the neural network described herein.

In general, the word "module," as used herein, refers to logic embodied in hardware or firmware, or to a collection of software instructions, possibly having entry and exit points, written in a programming language, such as, for example, Python, Java, Lua, C and/or C++. A software module may be compiled and linked into an executable program, installed in a dynamic link library, or may be written in an interpreted programming language such as, for example, BASIC, Perl, or Python. It will be appreciated that software modules may be callable from other modules or from themselves, and/or may be invoked in response to detected events or interrupts. Software modules configured for execution on computing devices may be provided on a computer readable medium, such as a compact disc, digital video disc, flash drive, or any other tangible medium. Such software code may be stored, partially or fully, on a memory device of the executing computing device, such as the computing system 13000, for execution by the computing device. Software instructions may be embedded in firmware, such as an EPROM. It will be further appreciated that hardware modules may be comprised of connected logic units, such as gates and flip-flops, and/or may be comprised of programmable units, such as programmable gate arrays or processors. The block diagrams disclosed herein may be implemented as modules. The modules described herein may be implemented as software modules, but may be represented in hardware or firmware. Generally, the modules described herein refer to logical modules that may be combined with other modules or divided into sub-modules despite their physical organization or storage.

Each of the processes, methods, and algorithms described in the preceding sections may be embodied in, and fully or partially automated by, code modules executed by one or more computer systems or computer processors comprising computer hardware. The code modules may be stored on any type of non-transitory computer-readable medium or computer storage device, such as hard drives, solid state memory, optical disc, and/or the like. The systems and modules may also be transmitted as generated data signals (for example, as part of a carrier wave or other analog or digital propagated signal) on a variety of computer-readable transmission mediums, including wireless-based and wired/cable-based mediums, and may take a variety of forms (for example, as part of a single or multiplexed analog signal, or as multiple discrete digital packets or frames). The processes and algorithms may be implemented partially or wholly in application-specific circuitry. The results of the disclosed processes and process steps may be stored, persistently or otherwise, in any type of non-transitory computer storage such as, for example, volatile or non-volatile storage.

The various features and processes described above may be used independently of one another, or may be combined in various ways. All possible combinations and subcombinations are intended to fall within the scope of this disclosure. In addition, certain method or process blocks may be omitted in some implementations. The methods and processes described herein are also not limited to any particular sequence, and the blocks or states relating thereto can be performed in other sequences that are appropriate. For example, described blocks or states may be performed in an order other than that specifically disclosed, or multiple blocks or states may be combined in a single block or state. The example blocks or states may be performed in serial, in parallel, or in some other manner. Blocks or states may be added to or removed from the disclosed example embodiments. The example systems and components described herein may be configured differently than described. For example, elements may be added to, removed from, or rearranged compared to the disclosed example embodiments.

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment. The term "including" means "included but not limited to." The term "or" means "and/or."

Any process descriptions, elements, or blocks in the flow or block diagrams described herein and/or depicted in the attached figures should be understood as potentially representing modules, segments, or portions of code which include one or more executable instructions for implementing specific logical functions or steps in the process. Alternate implementations are included within the scope of the embodiments described herein in which elements or functions may be deleted, executed out of order from that shown or discussed, including substantially concurrently or in reverse order, depending on the functionality involved, as would be understood by those skilled in the art.

All of the methods and processes described above may be at least partially embodied in, and partially or fully automated via, software code modules executed by one or more computers. For example, the methods described herein may be performed by the computing system and/or any other suitable computing device. The methods may be executed on the computing devices in response to execution of software instructions or other executable code read from a tangible computer readable medium. A tangible computer readable medium is a data storage device that can store data that is readable by a computer system. Examples of computer readable mediums include read-only memory, random-access memory, other volatile or non-volatile memory devices, CD-ROMs, magnetic tape, flash drives, and optical data storage devices.

It should be emphasized that many variations and modifications may be made to the above-described embodiments, the elements of which are to be understood as being among other acceptable examples. All such modifications and variations are intended to be included herein within the scope of this disclosure. The foregoing description details certain embodiments. It will be appreciated, however, that no matter how detailed the foregoing appears in text, the systems and methods can be practiced in many ways. For example, a feature of one embodiment may be used with a feature in a different embodiment. As is also stated above, it should be noted that the use of particular terminology when describing certain features or aspects of the systems and methods should not be taken to imply that the terminology is being re-defined herein to be restricted to including any specific characteristics of the features or aspects of the systems and methods with which that terminology is associated.

Various embodiments of a physiological monitoring device, methods, and systems are disclosed herein. These various embodiments may be used alone or in combination, and various changes to individual features of the embodiments may be altered, without departing from the scope of the invention. For example, the order of various method steps may in some instances be changed, and/or one or more optional features may be added to or eliminated from a described device. Therefore, the description of the embodiments provided above should not be interpreted as unduly limiting the scope of the invention as it is set forth in the claims.

Various modifications to the implementations described in this disclosure may be made, and the generic principles defined herein may be applied to other implementations without departing from the spirit or scope of this disclosure. Thus, the scope of the disclosure is not intended to be limited to the implementations shown herein, but are to be accorded the widest scope consistent with this disclosure, the principles and the novel features disclosed herein.

Certain features that are described in this specification in the context of separate embodiments also can be implemented in combination in a single embodiment. Conversely, various features that are described in the context of a single embodiment also can be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, such operations need not be performed in the particular order shown or in sequential order, or that all illustrated operations be performed, to achieve desirable results. Further, the drawings may schematically depict one more example processes in the form of a flow diagram. However, other operations that are not depicted can be incorporated in the example processes that are schematically illustrated. For example, one or more additional operations can be performed before, after, simultaneously, or between any of the illustrated operations. Moreover, the separation of various system components in the embodiments described above should not be interpreted as requiring such separation in all embodiments. Additionally, other embodiments are within the scope of the following claims. In some cases, the actions recited in the claims can be performed in a different order and still achieve desirable results.

What is claimed is:

1. A monitor to infer a likelihood of a characteristic of a user, the monitor comprising:
   a watertight housing;
   a surface on the housing configured to be sealably engaged to a mammal;
   an adhesive on the surface configured to remain continuously affixed to the mammal for at least 7 days, without removal until completion of monitoring;
   at least two electrodes permanently disposed within the housing, positioned to detect continuous cardiac rhythm signals of the mammal while the surface is sealably engaged to the mammal;
   a printed circuit board assembly comprising a hardware processor configured to process the detected cardiac rhythm signals through an encoder, wherein the encoder comprises a first subset of layers of a neural network; and
   a transmitter, the transmitter configured to transmit the data output of the encoder to an external computing system, the external computing system configured to infer a likelihood of an occurrence of arrhythmia by processing the data output through a decoder, wherein the decoder comprises a second subset of layers of the neural network.

2. The monitor of claim 1, wherein the dimensionality of the data output of the first subset of the computer executable instructions that is transmitted to the computing system is smaller than the data of the detected signals from the at least two electrodes.

3. The monitor of claim 1, wherein the data output of the first subset of the computer executable instructions is encrypted, wherein the transmitter transmits the encrypted data output, wherein the computing system processes the encrypted data output through the second subset of computer executable instructions.

4. The monitor of claim 1, wherein the transmitter transmits the data output to the computing system via a wireless communication channel.

5. The monitor of claim 1, further comprising a receiver configured to receive an updated first subset of computer executable instructions from the computing system and updating the first subset of the computer executable instructions to the updated first subset of computer executable instructions, wherein the hardware processor is further configured to process signals through the updated first subset of computer executable instructions.

6. The monitor of claim 1, further comprising an accelerometer configured to gather motion data, wherein the computing system is configured to match motion data with the detected signals to infer the likelihood of the occurrence.

7. The monitor of claim 1, wherein the monitor is a cardiac monitor.

8. The monitor of claim 1, wherein the hardware processor is configured to select the neural network from a plurality of neural networks based on a characteristic.

9. The monitor of claim 8, wherein the characteristic comprises at least one of: a characteristic of the monitor, a network characteristic between the monitor and the computing system.

10. The monitor of claim 8, wherein the hardware processor is further configured to compress the output of the first subset of layers of the neural network, wherein to transmit the output of the first subset to the computing system comprises transmitting the compressed output, wherein the computing system is configured to decompress the transmitted data; and wherein processing the output through the second subset of layers comprises processing the decompressed data.

11. The monitor of claim 8, wherein the hardware processor is further configured to quantize the output of the first subset of layers of the neural network, wherein to transmit the output of the first subset to the computing system comprises transmitting the output.

12. The monitor of claim 8, wherein the characteristic comprises available processing power of the monitor.

13. The monitor method of claim 8, wherein the characteristic comprises available memory of the monitor.

14. The monitor of claim 8, wherein the characteristic comprises network availability between the monitor and the computing system.

15. The monitor of claim 8, wherein the characteristic comprises a type of the characteristic of the user.

16. The monitor of claim 15, wherein the type of the characteristic of the user includes an occurrence of cardiac arrhythmia.

17. The monitor of claim 1, wherein the arrhythmia comprises at least one of: ventricular tachycardia, supraventricular tachycardia, ectopy, ventricular fibrillation, or extended pauses.

18. The monitor of claim 1, wherein to infer a likelihood of an occurrence of cardiac arrhythmia comprises processing the output of the first subset through the second subset, wherein the first subset processed at least 24 hours of continuously detected, stored cardiac rhythm signals.

19. The monitor of claim 1, wherein the housing comprises a patient trigger configured to depress and initiate recordation of an instance in time of a perceived cardiac event.

* * * * *

UNITED STATES PATENT AND TRADEMARK OFFICE
CERTIFICATE OF CORRECTION

PATENT NO. : 11,083,371 B1  
APPLICATION NO. : 17/174145  
DATED : August 10, 2021  
INVENTOR(S) : Szabados et al.

Page 1 of 2

It is certified that error appears in the above-identified patent and that said Letters Patent is hereby corrected as shown below:

On the Title Page

On Page 5, Column 2, Item (56), Line 54, under U.S. Patent Documents, delete "Mazer" and insert --Mazar--.

On Page 6, Column 1, Item (56), Line 61, under U.S. Patent Documents, delete "Mager" and insert --Mazar--.

On Page 6, Column 2, Item (56), Line 5, under U.S. Patent Documents, delete "Benet" and insert --Banet--.

On Page 6, Column 2, Item (56), Line 10, under Foreign Patent Documents, delete "000" and insert --0001--.

On Page 6, Column 2, Item (56), Line 11, under Foreign Patent Documents, delete "000" and insert --0001--.

On Page 6, Column 2, Item (56), Line 11, under Foreign Patent Documents, below "EM 003611714-000 1/2017" insert --EM 003611714-0002 1/2017 EM 003611714-0003 1/2017 EM 003611714-0004 1/2017 EM 003611714-0005 1/2017--.

On Page 6, Column 2, Item (56), Line 28, under Foreign Patent Documents, delete "000" and insert --0001--.

On Page 7, Column 2, Item (56), Line 6, under Other Publications, delete "Proceddings" and insert --Proceedings--.

On Page 7, Column 2, Item (56), Line 12, under Other Publications, delete "Partch" and insert --Patch--.

Signed and Sealed this  
Twenty-sixth Day of October, 2021

Drew Hirshfeld  
*Performing the Functions and Duties of the*  
*Under Secretary of Commerce for Intellectual Property and*  
*Director of the United States Patent and Trademark Office*

CERTIFICATE OF CORRECTION (continued)
U.S. Pat. No. 11,083,371 B1

On Page 7, Column 2, Item (56), Line 17, under Other Publications, delete "Eurospace;" and insert --Europace;--.

In the Drawings

On Sheet 28 of 41, FIG. 20, Line 2, delete "Perdiction" and insert --Prediction--.

In the Specification

In Column 13, Line 55, delete "both" and insert --both.--.

In Column 18, Line 11, delete "impedence," and insert --impedance,--.

In Column 20, Line 52, delete "(such" and insert --such--.

In Column 22, Line 10, delete "Nw" and insert --$N_w$--.

In Column 31, Line 34, delete "-2-33" and insert --~2-33--.

In Column 36, Line 63, delete "issues)" and insert --issues).--.

In the Claims

In Column 46, Claim 13, Line 66, delete "monitor method" and insert --monitor--.